US010525072B2

(12) United States Patent
Sommadossi et al.

(10) Patent No.: US 10,525,072 B2
(45) Date of Patent: *Jan. 7, 2020

(54) 2'-BRANCHED NUCLEOSIDES AND FLAVIVIRIDAE MUTATION

(71) Applicants: Idenix Pharmaceuticals LLC, Cambridge, MA (US); Universita Degli Studi Di Cagliari, Cagliari (IT)

(72) Inventors: Jean-Pierre Sommadossi, Boston, MA (US); Paolo La Colla, Capoterra (IT); David N. Standring, Milton, MA (US); Vadim Bichko, San Diego, CA (US); Lin Qu, Webster, TX (US)

(73) Assignees: Idenix Pharmaceuticals LLC, Cambridge, MA (US); Universita Degli Studi Di Cagliari, Cagliari (IT)

( * ) Notice: Subject to any disclaimer, the term of this patent is extended or adjusted under 35 U.S.C. 154(b) by 551 days.

This patent is subject to a terminal disclaimer.

(21) Appl. No.: 14/972,009

(22) Filed: Dec. 16, 2015

(65) Prior Publication Data

US 2016/0166597 A1   Jun. 16, 2016

Related U.S. Application Data

(63) Continuation of application No. 14/183,438, filed on Feb. 18, 2014, now abandoned, which is a (Continued)

(51) Int. Cl.
*C12Q 1/70* (2006.01)
*A61K 31/7072* (2006.01)
(Continued)

(52) U.S. Cl.
CPC ...... *A61K 31/7072* (2013.01); *A61K 31/7052* (2013.01); *A61K 38/21* (2013.01);
(Continued)

(58) Field of Classification Search
None
See application file for complete search history.

(56) References Cited

U.S. PATENT DOCUMENTS 3,116,282 A   12/1963  Hunter
3,480,613 A   11/1969  Walton
(Continued)

FOREIGN PATENT DOCUMENTS

CA   2252144   4/2000
DE   1919307   1/1971
(Continued)

OTHER PUBLICATIONS

U.S. Appl. No. 10/845,976, filed May 14, 2004, Storer, et al.
(Continued)

*Primary Examiner* — M Franco G Salvoza
(74) *Attorney, Agent, or Firm* — Jones Day

(57) ABSTRACT

The present invention discloses a method for the treatment of Flaviviridae infection that includes the administration of a 2'-branched nucleoside, or a pharmaceutically acceptable prodrug and/or salt thereof, to a human in need of therapy in combination or alternation with a drug that directly or indirectly induces a mutation in the viral genome at a location other than a mutation of a nucleotide that results in a change from serine to a different amino acid in the highly conserved consensus sequence, XRXSGXXXT (SEQ ID NO: 63), of domain B of the RNA polymerase region, or is associated with such a mutation. The invention also includes a method to detect a mutant strain of Flaviviridae and a method for its treatment.

12 Claims, 11 Drawing Sheets

Specification includes a Sequence Listing.

Related U.S. Application Data continuation of application No. 12/914,914, filed on Oct. 28, 2010, now Pat. No. 8,674,085, which is a continuation of application No. 10/715,729, filed on Nov. 17, 2003, now Pat. No. 7,824,851.

(60) Provisional application No. 60/042,675, filed on Nov. 15, 2002.

(51) Int. Cl.

| | |
|---|---|
| A61K 31/7052 | (2006.01) |
| A61K 38/21 | (2006.01) |
| A61K 45/06 | (2006.01) |
| C07H 19/06 | (2006.01) |
| C07H 19/16 | (2006.01) |
| C07K 14/005 | (2006.01) |
| C12Q 1/04 | (2006.01) |
| C12Q 1/18 | (2006.01) |

(52) U.S. Cl.
CPC .......... *A61K 38/212* (2013.01); *A61K 38/215* (2013.01); *A61K 38/217* (2013.01); *A61K 45/06* (2013.01); *C07H 19/06* (2013.01); *C07H 19/16* (2013.01); *C07K 14/005* (2013.01); *C12Q 1/04* (2013.01); *C12Q 1/18* (2013.01); *C12Q 1/701* (2013.01); *C12Q 1/707* (2013.01); *C12N 2770/24022* (2013.01); *C12N 2770/24122* (2013.01); *C12N 2770/24222* (2013.01); *C12Q 2600/156* (2013.01); *C12Q 2600/158* (2013.01); *G01N 2333/186* (2013.01)

(56) References Cited

U.S. PATENT DOCUMENTS

| | | | |
|---|---|---|---|
| 3,798,209 A | 3/1974 | Witkowski et al. | |
| 3,891,623 A | 6/1975 | Vorbruggen et al. | |
| 4,022,889 A | 5/1977 | Bannister et al. | |
| 4,058,602 A | 11/1977 | Beisler et al. | |
| RE29,835 E | 11/1978 | Witkowski et al. | |
| 4,209,613 A | 6/1980 | Vorbruggen et al. | |
| 4,239,753 A | 12/1980 | Skulnick et al. | |
| 4,294,766 A | 10/1981 | Schmidt et al. | |
| 4,522,811 A | 6/1985 | Eppstein et al. | |
| 4,605,659 A | 8/1986 | Verheyden et al. | |
| 4,689,404 A | 8/1987 | Kawada et al. | |
| 4,754,026 A | 6/1988 | Kawada et al. | |
| 4,814,477 A | 3/1989 | Wijnberg et al. | |
| 4,880,784 A | 11/1989 | Robins et al. | |
| 4,952,740 A | 8/1990 | Juge et al. | |
| 4,957,924 A | 9/1990 | Beauchamp | |
| 5,034,394 A | 7/1991 | Daluge | |
| 5,122,517 A | 6/1992 | Vince et al. | |
| 5,149,794 A | 9/1992 | Yatvin et al. | |
| 5,157,027 A | 10/1992 | Biller et al. | |
| 5,194,654 A | 3/1993 | Hostetler et al. | |
| 5,200,514 A | 4/1993 | Chu | |
| 5,223,263 A | 6/1993 | Hostetler et al. | |
| 5,246,924 A | 9/1993 | Fox et al. | |
| 5,256,641 A | 10/1993 | Yatvin et al. | |
| 5,256,797 A | 10/1993 | Chou et al. | |
| 5,322,955 A | 6/1994 | Matsumoto et al. | |
| 5,371,210 A | 12/1994 | Chou et al. | |
| 5,372,808 A | 12/1994 | Blatt et al. | |
| 5,391,769 A | 2/1995 | Matsumoto et al. | |
| 5,401,861 A | 3/1995 | Chou et al. | |
| 5,411,947 A | 5/1995 | Hostetler et al. | |
| 5,463,092 A | 10/1995 | Hostetler et al. | |
| 5,539,116 A | 7/1996 | Liotta et al. | |
| 5,543,389 A | 8/1996 | Yatvin et al. | |
| 5,543,390 A | 8/1996 | Yatvin et al. | |
| 5,543,391 A | 8/1996 | Yatvin et al. | |
| 5,554,728 A | 9/1996 | Basava et al. | |
| 5,565,438 A | 10/1996 | Chu et al. | |
| 5,567,688 A | 10/1996 | Chu et al. | |
| 5,587,362 A | 12/1996 | Chu et al. | |
| 5,606,048 A | 2/1997 | Chou et al. | |
| 5,676,942 A | 10/1997 | Testa et al. | |
| 5,696,277 A | 12/1997 | Hostetler et al. | |
| 5,738,845 A | 4/1998 | Imakawa | |
| 5,744,600 A | 4/1998 | Mansuri et al. | |
| 5,750,676 A | 5/1998 | Vorbruggen et al. | |
| 5,763,418 A | 6/1998 | Matsuda et al. | |
| 5,780,617 A | 7/1998 | Van den Bosch et al. | |
| 5,789,608 A | 8/1998 | Glazier | |
| 5,821,357 A | 10/1998 | Chou et al. | |
| 5,830,455 A | 11/1998 | Valtuena et al. | |
| 5,849,696 A | 12/1998 | Chretien et al. | |
| 5,908,621 A | 6/1999 | Glue et al. | |
| 5,928,636 A | 7/1999 | Alber et al. | |
| 5,942,223 A | 8/1999 | Bazer et al. | |
| 5,977,061 A | 11/1999 | Holy et al. | |
| 5,977,325 A | 11/1999 | McCarthy et al. | |
| 5,980,884 A | 11/1999 | Blatt et al. | |
| 6,002,029 A | 12/1999 | Hostetler et al. | |
| 6,063,628 A | 5/2000 | Loeb et al. | |
| 6,140,310 A | 10/2000 | Glazier | |
| 6,153,594 A | 11/2000 | Borretzen et al. | |
| 6,156,501 A | 12/2000 | McGall et al. | |
| 6,172,046 B1 | 1/2001 | Albrecht | |
| 6,174,868 B1 | 1/2001 | Anderson et al. | |
| 6,248,878 B1 | 6/2001 | Matulic-Adamic et al. | |
| 6,252,060 B1 | 6/2001 | Hostetler | |
| 6,271,212 B1 | 8/2001 | Chu et al. | |
| 6,277,830 B1 | 8/2001 | Ganguly et al. | |
| 6,284,458 B1 | 9/2001 | Anderson et al. | |
| 6,312,662 B1 | 11/2001 | Erion et al. | |
| 6,340,690 B1 | 1/2002 | Bachand et al. | |
| 6,348,587 B1 | 2/2002 | Schinazi et al. | |
| 6,369,040 B1 | 4/2002 | Acevedo et al. | |
| 6,391,542 B1 | 5/2002 | Anderson et al. | |
| 6,395,716 B1 | 5/2002 | Gosselin et al. | |
| 6,423,489 B1 | 7/2002 | Anderson et al. | |
| 6,433,159 B1 | 8/2002 | Anderson | |
| 6,436,437 B1 | 8/2002 | Yatvin et al. | |
| 6,444,652 B1 | 9/2002 | Gosselin et al. | |
| 6,448,392 B1 | 9/2002 | Hostetler et al. | |
| 6,455,508 B1 | 9/2002 | Ramasamy et al. | |
| 6,455,513 B1 | 9/2002 | McGuigan et al. | |
| 6,458,772 B1 | 10/2002 | Zhou et al. | |
| 6,458,773 B1 | 10/2002 | Gosselin et al. | |
| 6,472,373 B1 | 10/2002 | Albrecht | |
| 6,495,677 B1 | 12/2002 | Ramasamy et al. | |
| 6,566,344 B1 | 5/2003 | Gosselin et al. | |
| 6,566,365 B1 | 5/2003 | Storer | |
| 6,569,837 B1 | 5/2003 | Gosselin et al. | |
| 6,573,247 B1 | 6/2003 | McGuigan et al. | |
| 6,573,248 B2 | 6/2003 | Ramasamy et al. | |
| 6,596,700 B2 | 7/2003 | Sommadossi et al. | |
| 6,599,887 B2 | 7/2003 | Hostetler et al. | |
| 6,605,614 B2 | 8/2003 | Bachand et al. | |
| 6,608,191 B1 | 8/2003 | Anderson et al. | |
| 6,638,919 B2 | 10/2003 | McGuigan et al. | |
| 6,642,206 B2 | 11/2003 | Ramasamy et al. | |
| 6,660,721 B2 | 12/2003 | Devos et al. | |
| 6,748,161 B2 | 6/2004 | Ko et al. | |
| 6,752,981 B1 | 6/2004 | Erion et al. | |
| 6,777,395 B2 | 8/2004 | Bhat et al. | |
| 6,784,161 B2 | 8/2004 | Ismaili et al. | |
| 6,784,166 B2 | 8/2004 | Devos et al. | |
| 6,787,526 B1 | 9/2004 | Bryant et al. | |
| 6,812,219 B2 | 11/2004 | LaColla et al. | |
| 6,815,542 B2 | 11/2004 | Hong et al. | |
| 6,831,069 B2 | 12/2004 | Tam et al. | |
| 6,833,361 B2 | 12/2004 | Hong et al. | |
| 6,846,810 B2 | 1/2005 | Martin et al. | |
| 6,875,751 B2 | 4/2005 | Imbach et al. | |
| 6,908,924 B2 | 6/2005 | Watanabe et al. | |
| 6,911,424 B2 | 6/2005 | Schinazi et al. | |
| 6,914,054 B2 | 7/2005 | Sommadossi et al. | |
| 6,927,291 B2 | 8/2005 | Jin et al. | |

(56) References Cited

U.S. PATENT DOCUMENTS

| | | |
|---|---|---|
| 6,946,115 B2 | 9/2005 | Erion et al. |
| 6,946,450 B2 | 9/2005 | Gosselin et al. |
| 6,949,522 B2 | 9/2005 | Otto et al. |
| 6,965,033 B2 | 11/2005 | Jiang et al. |
| 6,965,066 B1 | 11/2005 | Jiang et al. |
| 7,018,989 B2 | 3/2006 | McGuigan et al. |
| 7,019,135 B2 | 3/2006 | McGuigan et al. |
| 7,056,895 B2 | 6/2006 | Ramasamy et al. |
| 7,094,770 B2 | 8/2006 | Watanabe et al. |
| 7,101,861 B2 | 9/2006 | Sommadossi et al. |
| 7,105,493 B2 | 9/2006 | Sommadossi et al. |
| 7,105,499 B2 * | 9/2006 | Carroll ............... A61K 31/7076 514/42 |
| 7,125,855 B2 | 10/2006 | Bhat et al. |
| 7,138,376 B2 | 11/2006 | Gosselin et al. |
| 7,144,868 B2 | 12/2006 | Roberts et al. |
| 7,148,206 B2 | 12/2006 | Sommadossi et al. |
| 7,151,089 B2 | 12/2006 | Roberts et al. |
| 7,157,434 B2 | 1/2007 | Keicher et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,285,658 B2 | 10/2007 | Cook et al. |
| 7,300,924 B2 | 11/2007 | Boojamra et al. |
| 7,307,065 B2 | 12/2007 | Schinazi et al. |
| 7,323,449 B2 | 1/2008 | Olsen et al. |
| 7,323,453 B2 | 1/2008 | Olsen et al. |
| 7,339,054 B2 | 3/2008 | Xu et al. |
| 7,365,057 B2 | 4/2008 | LaColla et al. |
| 7,384,924 B2 | 6/2008 | LaColla et al. |
| 7,432,248 B2 * | 10/2008 | Roberts .................. C07H 19/00 514/43 |
| 7,452,901 B2 | 11/2008 | Boojamra et al. |
| 7,456,155 B2 | 11/2008 | Sommadossi et al. |
| 7,534,767 B2 | 5/2009 | Butora et al. |
| 7,547,704 B2 | 6/2009 | LaColla et al. |
| 7,582,618 B2 | 9/2009 | Sommadossi et al. |
| 7,598,230 B2 | 10/2009 | Cook et al. |
| 7,598,373 B2 | 10/2009 | Storer et al. |
| 7,608,597 B2 | 10/2009 | Sommadossi et al. |
| 7,608,600 B2 | 10/2009 | Storer et al. |
| 7,625,875 B2 | 12/2009 | Gosselin et al. |
| 7,632,821 B2 | 12/2009 | Butora et al. |
| 7,635,689 B2 | 12/2009 | LaColla et al. |
| 7,645,747 B2 | 1/2010 | Boojamra et al. |
| 7,662,798 B2 | 2/2010 | LaColla et al. |
| 7,754,699 B2 | 7/2010 | Chun et al. |
| 7,772,208 B2 | 8/2010 | Schinazi et al. |
| 7,781,576 B2 | 8/2010 | Mayes et al. |
| 7,807,653 B2 | 10/2010 | Cook et al. |
| 7,820,631 B2 | 10/2010 | McGuigan et al. |
| 7,824,851 B2 | 11/2010 | Sommadossi et al. |
| 7,842,672 B2 | 11/2010 | Boojamra et al. |
| 7,871,991 B2 | 1/2011 | Boojamra et al. |
| 7,879,815 B2 | 2/2011 | MacCoss et al. |
| 7,902,202 B2 | 3/2011 | Sommadossi et al. |
| 7,951,787 B2 | 5/2011 | McGuigan |
| 7,951,789 B2 | 5/2011 | Sommadossi et al. |
| 7,964,580 B2 | 6/2011 | Sofia et al. |
| 7,973,013 B2 | 7/2011 | Cho et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,022,083 B2 | 9/2011 | Boojamra et al. |
| 8,119,779 B2 | 2/2012 | McGuigan et al. |
| 8,148,349 B2 | 4/2012 | Meppen et al. |
| 8,168,583 B2 | 5/2012 | Schinazi et al. |
| 8,173,621 B2 | 5/2012 | Du et al. |
| 8,183,216 B2 | 5/2012 | Di Francesco et al. |
| 8,299,038 B2 | 10/2012 | Sommadossi et al. |
| 8,318,701 B2 | 11/2012 | Boojamra et al. |
| 8,324,179 B2 | 12/2012 | Chen et al. |
| 8,329,926 B2 | 12/2012 | Boojamra et al. |
| 8,334,270 B2 | 12/2012 | Sofia et al. |
| 8,415,308 B2 | 4/2013 | Cho et al. |
| 8,455,451 B2 | 6/2013 | Cho et al. |
| 8,481,713 B2 | 7/2013 | Wang et al. |
| 8,507,460 B2 | 8/2013 | Surleraux et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,569,478 B2 | 10/2013 | Du et al. |
| 8,575,119 B2 | 11/2013 | Wang et al. |
| 8,580,268 B2 | 11/2013 | Debelak et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,637,475 B1 | 1/2014 | Storer et al. |
| 8,642,756 B2 | 2/2014 | Ross et al. |
| 8,658,616 B2 | 2/2014 | McGuigan et al. |
| 8,680,071 B2 | 3/2014 | Surleraux et al. |
| 8,691,788 B2 | 4/2014 | Sommadossi et al. |
| 8,716,262 B2 | 5/2014 | Sofia et al. |
| 8,716,263 B2 | 5/2014 | Chun et al. |
| 8,735,372 B2 | 5/2014 | Du et al. |
| 8,759,510 B2 | 6/2014 | Du et al. |
| 8,765,710 B2 | 7/2014 | Sofia et al. |
| 8,816,074 B2 | 8/2014 | Chu et al. |
| 8,841,275 B2 | 9/2014 | Du et al. |
| 8,859,756 B2 | 10/2014 | Ross et al. |
| 8,877,733 B2 | 11/2014 | Cho et al. |
| 8,889,159 B2 | 11/2014 | Cleary et al. |
| 8,906,880 B2 | 12/2014 | Du et al. |
| 8,946,244 B2 | 2/2015 | Chu et al. |
| 8,951,985 B2 | 2/2015 | Surleraux et al. |
| 2002/0019363 A1 | 2/2002 | Ismaili et al. |
| 2002/0035085 A1 | 3/2002 | Somadossi et al. |
| 2002/0052345 A1 | 5/2002 | Erion et al. |
| 2002/0055473 A1 | 5/2002 | Ganguly et al. |
| 2002/0055483 A1 | 5/2002 | Watanable et al. |
| 2002/0095033 A1 | 7/2002 | Ramasamy et al. |
| 2002/0099072 A1 | 7/2002 | Bachand et al. |
| 2002/0127203 A1 | 9/2002 | Albrecht |
| 2002/0147160 A1 | 10/2002 | Bhat et al. |
| 2002/0156030 A1 | 10/2002 | Ramasamy et al. |
| 2002/0173490 A1 | 11/2002 | Jiang et al. |
| 2002/0198171 A1 | 12/2002 | Schinazi et al. |
| 2003/0008841 A1 | 1/2003 | Devos et al. |
| 2003/0028013 A1 | 2/2003 | Wang et al. |
| 2003/0039630 A1 | 2/2003 | Albrecht |
| 2003/0050229 A1 | 3/2003 | Sommadossi et al. |
| 2003/0053986 A1 | 3/2003 | Zahm |
| 2003/0055013 A1 | 3/2003 | Brass |
| 2003/0060400 A1 | 3/2003 | Lacolla et al. |
| 2003/0083306 A1 | 5/2003 | Imbach et al. |
| 2003/0083307 A1 | 5/2003 | Devos et al. |
| 2003/0087873 A1 | 5/2003 | Stuyver et al. |
| 2003/0124512 A1 | 7/2003 | Styuver |
| 2003/0220290 A1 | 11/2003 | Gosselin et al. |
| 2003/0225028 A1 | 12/2003 | Gosselin et al. |
| 2003/0225029 A1 | 12/2003 | Stuyver |
| 2003/0225037 A1 | 12/2003 | Storer et al. |
| 2003/0236216 A1 | 12/2003 | Devos et al. |
| 2004/0002476 A1 | 1/2004 | Stuyver et al. |
| 2004/0002596 A1 | 1/2004 | Hong et al. |
| 2004/0006002 A1 | 1/2004 | Sommadossi et al. |
| 2004/0014108 A1 | 1/2004 | Eldrup et al. |
| 2004/0023921 A1 | 2/2004 | Hong et al. |
| 2004/0059104 A1 | 3/2004 | Cook et al. |
| 2004/0063622 A1 | 4/2004 | Sommadossi et al. |
| 2004/0063658 A1 | 4/2004 | Roberts et al. |
| 2004/0067901 A1 | 4/2004 | Bhat et al. |
| 2004/0072788 A1 | 4/2004 | Bhat et al. |
| 2004/0077587 A1 | 4/2004 | Sommadossi et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0110718 A1 | 6/2004 | Devos et al. |
| 2004/0121980 A1 | 6/2004 | Martin et al. |
| 2004/0147464 A1 | 7/2004 | Roberts et al. |

(56) References Cited

U.S. PATENT DOCUMENTS

| | | |
|---|---|---|
| 2004/0229839 A1 | 11/2004 | Babu et al. |
| 2004/0229840 A1 | 11/2004 | Bhat et al. |
| 2004/0248844 A1 | 12/2004 | Ismaili et al. |
| 2004/0259934 A1 | 12/2004 | Olsen et al. |
| 2004/0266722 A1 | 12/2004 | Devos et al. |
| 2004/0266723 A1 | 12/2004 | Otto et al. |
| 2004/0266996 A1 | 12/2004 | Rabi |
| 2005/0009737 A1 | 1/2005 | Clark et al. |
| 2005/0020825 A1 | 1/2005 | Storer et al. |
| 2005/0031588 A1 | 2/2005 | Sommadossi et al. |
| 2005/0038240 A1 | 2/2005 | Connolly et al. |
| 2005/0090463 A1 | 4/2005 | Roberts et al. |
| 2005/0101550 A1 | 5/2005 | Roberts et al. |
| 2005/0107312 A1 | 5/2005 | Keicher et al. |
| 2005/0113330 A1 | 5/2005 | Imbach et al. |
| 2005/0119200 A1 | 6/2005 | Roberts et al. |
| 2005/0124532 A1 | 6/2005 | Sommadossi et al. |
| 2005/0137141 A1 | 6/2005 | Hilfinger et al. |
| 2005/0137161 A1 | 6/2005 | Sommadossi et al. |
| 2005/0215511 A1 | 9/2005 | Roberts et al. |
| 2006/0040944 A1 | 2/2006 | Gosselin et al. |
| 2006/0040890 A1 | 3/2006 | Martin et al. |
| 2006/0111311 A1 | 5/2006 | Keicher et al. |
| 2006/0166865 A1 | 7/2006 | Sommadossi et al. |
| 2006/0194835 A1 | 8/2006 | Dugourd et al. |
| 2006/0199783 A1 | 9/2006 | Wang et al. |
| 2006/0234962 A1 | 10/2006 | Olsen et al. |
| 2006/0241064 A1 | 10/2006 | Roberts et al. |
| 2006/0264389 A1 | 11/2006 | Bhat et al. |
| 2007/0004669 A1 | 1/2007 | Carroll et al. |
| 2007/0015905 A1 | 1/2007 | LaColla et al. |
| 2007/0027065 A1 | 2/2007 | LaColla et al. |
| 2007/0027104 A1 | 2/2007 | LaColla et al. |
| 2007/0032449 A1 | 2/2007 | LaColla et al. |
| 2007/0037735 A1 | 2/2007 | Gosselin et al. |
| 2007/0042990 A1 | 2/2007 | Gosselin et al. |
| 2007/0060503 A1 | 3/2007 | Gosselin et al. |
| 2007/0060504 A1 | 3/2007 | Gosselin et al. |
| 2007/0060505 A1 | 3/2007 | Gosselin et al. |
| 2007/0060541 A1 | 3/2007 | Gosselin et al. |
| 2007/0203334 A1 | 8/2007 | Mayes et al. |
| 2007/0265222 A1 | 11/2007 | MacCoss et al. |
| 2008/0070861 A1 | 3/2008 | Clark |
| 2008/0139802 A1 | 6/2008 | Axt et al. |
| 2008/0253995 A1 | 10/2008 | Clark |
| 2008/0261913 A1 | 10/2008 | Sommadossi et al. |
| 2008/0280842 A1 | 11/2008 | MacCoss et al. |
| 2009/0004135 A1 | 1/2009 | Clark |
| 2009/0036666 A1 | 2/2009 | Clark |
| 2009/0048189 A1 | 2/2009 | Keicher et al. |
| 2009/0118223 A1 | 5/2009 | Erion et al. |
| 2009/0176732 A1 | 7/2009 | Beigelman et al. |
| 2009/0318380 A1 | 12/2009 | Sofia et al. |
| 2010/0003217 A1 | 1/2010 | Cretton-Scott et al. |
| 2010/0279969 A1 | 11/2010 | Schinazi et al. |
| 2010/0279974 A1 | 11/2010 | Pierra et al. |
| 2010/0316594 A1 | 12/2010 | Sommadossi et al. |
| 2011/0269707 A1 | 11/2011 | Stuyver et al. |
| 2011/0306541 A1 | 12/2011 | Delaney, IV et al. |
| 2011/0306573 A1 | 12/2011 | Avolio et al. |
| 2012/0010164 A1 | 1/2012 | Summa et al. |
| 2012/0107274 A1 | 5/2012 | Clarke et al. |
| 2012/0245335 A1 | 9/2012 | Clark |
| 2012/0251487 A1 | 10/2012 | Surleraux |
| 2013/0017171 A1 | 1/2013 | Sommadossi et al. |
| 2013/0064794 A1 | 3/2013 | Surleraux et al. |
| 2013/0149283 A1 | 6/2013 | Sommadossi et al. |
| 2013/0273005 A1 | 10/2013 | Delaney et al. |
| 2013/0281686 A1 | 10/2013 | Cho et al. |
| 2013/0315862 A1 | 11/2013 | Sommadossi et al. |
| 2013/0315866 A1 | 11/2013 | Parsy et al. |
| 2013/0315867 A1 | 11/2013 | Parsy et al. |
| 2013/0315868 A1 | 11/2013 | Mayes et al. |
| 2013/0330297 A1 | 12/2013 | Storer et al. |
| 2014/0038916 A1 | 2/2014 | Chang et al. |
| 2014/0086873 A1 | 3/2014 | Mayes et al. |
| 2014/0099283 A1 | 4/2014 | Gosselin et al. |
| 2014/0112886 A1 | 4/2014 | Moussa et al. |
| 2014/0112887 A1 | 4/2014 | Mayes et al. |
| 2014/0113880 A1 | 4/2014 | Storer et al. |
| 2014/0128339 A1 | 5/2014 | Girijavallabhan et al. |
| 2014/0140951 A1 | 5/2014 | Moussa et al. |
| 2014/0140952 A1 | 5/2014 | Moussa et al. |
| 2014/0140955 A1 | 5/2014 | McGuigan et al. |
| 2014/0154211 A1 | 6/2014 | Girijavallabhan et al. |
| 2014/0161770 A1 | 6/2014 | Girijavallabhan et al. |
| 2014/0178338 A1 | 6/2014 | Mayes et al. |
| 2014/0206640 A1 | 7/2014 | Girijavallabhan et al. |
| 2014/0212382 A1 | 7/2014 | Schinazi et al. |
| 2014/0248241 A1 | 9/2014 | Stewart et al. |
| 2014/0248242 A1 | 9/2014 | Dousson et al. |
| 2014/0271547 A1 | 9/2014 | Dukhan et al. |
| 2014/0294769 A1 | 10/2014 | Mayes et al. |
| 2014/0364446 A1 | 12/2014 | Dukhan et al. |
| 2015/0037282 A1 | 2/2015 | Mayes et al. |

FOREIGN PATENT DOCUMENTS

| | | |
|---|---|---|
| DE | 2122991 | 11/1972 |
| DE | 2508312 | 9/1976 |
| DE | 140254 | 2/1980 |
| DE | 3512781 | 10/1985 |
| DE | 4224737 | 2/1994 |
| DE | 102005012681 | 9/2006 |
| EP | 0288847 | 4/1988 |
| EP | 0180276 | 12/1988 |
| EP | 0352248 | 1/1990 |
| EP | 0494119 | 1/1992 |
| EP | 0526655 | 2/1993 |
| EP | 0553358 | 8/1993 |
| EP | 0587364 | 3/1994 |
| EP | 0742287 | 11/1996 |
| EP | 0747389 | 12/1996 |
| EP | 0350287 | 9/2000 |
| EP | 0650371 | 11/2000 |
| FR | 1521076 | 4/1968 |
| FR | 1581628 | 9/1969 |
| FR | 2662165 | 11/1991 |
| GB | 924246 | 4/1963 |
| GB | 984877 | 3/1965 |
| GB | 1187824 | 5/1966 |
| GB | 1163102 | 9/1969 |
| GB | 1163103 | 9/1969 |
| GB | 1209654 | 10/1970 |
| GB | 1542442 | 3/1979 |
| JP | 71021872 | 3/1968 |
| JP | 48048495 | 9/1971 |
| JP | 61212592 | 9/1986 |
| JP | 61263995 | 11/1986 |
| JP | 61263996 | 11/1986 |
| JP | 63215694 | 9/1988 |
| JP | 02091022 | 3/1990 |
| JP | 06135988 | 5/1994 |
| JP | 06211890 | 8/1994 |
| JP | 06228186 | 8/1994 |
| JP | 06293645 | 10/1994 |
| JP | 09059292 | 3/1997 |
| WO | WO 89/002733 | 4/1989 |
| WO | WO 90/000555 | 1/1990 |
| WO | WO 91/016920 | 11/1991 |
| WO | WO 91/018914 | 12/1991 |
| WO | WO 91/019721 | 12/1991 |
| WO | WO 92/015308 | 9/1992 |
| WO | WO 92/018517 | 10/1992 |
| WO | WO 93/000910 | 1/1993 |
| WO | WO 93/017651 | 9/1993 |
| WO | WO 94/001117 | 1/1994 |
| WO | WO 94/026273 | 11/1994 |
| WO | WO 96/015132 | 5/1996 |
| WO | WO 98/016184 | 4/1998 |
| WO | WO 99/043691 | 2/1999 |
| WO | WO 99/015194 | 4/1999 |
| WO | WO 99/023104 | 5/1999 |
| WO | WO 99/045016 | 9/1999 |

(56) References Cited

FOREIGN PATENT DOCUMENTS

| | | |
|---|---|---|
| WO | WO 99/052514 | 10/1999 |
| WO | WO 99/059621 | 11/1999 |
| WO | WO 99/064016 | 12/1999 |
| WO | WO 00/009531 | 2/2000 |
| WO | WO 00/024355 | 5/2000 |
| WO | WO 00/025799 | 5/2000 |
| WO | WO 00/037110 | 6/2000 |
| WO | WO 00/052015 | 9/2000 |
| WO | WO 01/018013 | 3/2001 |
| WO | WO 01/032153 | 5/2001 |
| WO | WO 01/047935 | 7/2001 |
| WO | WO 01/049700 | 7/2001 |
| WO | WO 01/060315 | 8/2001 |
| WO | WO 01/068663 | 9/2001 |
| WO | WO 01/079246 | 10/2001 |
| WO | WO 01/081359 | 11/2001 |
| WO | WO 01/090121 | 11/2001 |
| WO | WO 01/091737 | 12/2001 |
| WO | WO 01/092282 | 12/2001 |
| WO | WO 01/096353 | 12/2001 |
| WO | WO 02/003997 | 1/2002 |
| WO | WO 02/018404 | 3/2002 |
| WO | WO 02/032414 | 4/2002 |
| WO | WO 02/032920 | 4/2002 |
| WO | WO 02/048165 | 6/2002 |
| WO | WO 02/057287 | 7/2002 |
| WO | WO 02/057425 | 7/2002 |
| WO | WO 02/070533 | 9/2002 |
| WO | WO 02/094289 | 11/2002 |
| WO | WO 02/100415 | 12/2002 |
| WO | WO 03/024461 | 3/2003 |
| WO | WO 03/026589 | 4/2003 |
| WO | WO 03/026675 | 4/2003 |
| WO | WO 03/039523 | 5/2003 |
| WO | WO 03/051899 | 6/2003 |
| WO | WO 03/081899 | 6/2003 |
| WO | WO 03/061385 | 7/2003 |
| WO | WO 03/061576 | 7/2003 |
| WO | WO 03/062255 | 7/2003 |
| WO | WO 03/062256 | 7/2003 |
| WO | WO 03/062257 | 7/2003 |
| WO | WO 03/063771 | 8/2003 |
| WO | WO 03/068162 | 8/2003 |
| WO | WO 03/068164 | 8/2003 |
| WO | WO 03/068244 | 8/2003 |
| WO | WO 03/072757 | 9/2003 |
| WO | WO 03/093290 | 11/2003 |
| WO | WO 03/099840 | 12/2003 |
| WO | WO 03/100017 | 12/2003 |
| WO | WO 03/105770 | 12/2003 |
| WO | WO 03/106577 | 12/2003 |
| WO | WO 04/000858 | 12/2003 |
| WO | WO 04/002422 | 1/2004 |
| WO | WO 04/002999 | 1/2004 |
| WO | WO 04/003138 | 1/2004 |
| WO | WO 04/007512 | 1/2004 |
| WO | WO 04/009020 | 1/2004 |
| WO | WO 04/023921 | 3/2004 |
| WO | WO 04/028481 | 4/2004 |
| WO | WO 04/041203 | 5/2004 |
| WO | WO 04/043977 | 5/2004 |
| WO | WO 04/043978 | 5/2004 |
| WO | WO 04/044132 | 5/2004 |
| WO | WO 04/046159 | 6/2004 |
| WO | WO 04/046331 | 6/2004 |
| WO | WO 04/052899 | 6/2004 |
| WO | WO 04/058792 | 7/2004 |
| WO | WO 04/065398 | 8/2004 |
| WO | WO 04/072090 | 8/2004 |
| WO | WO 04/080466 | 9/2004 |
| WO | WO 04/084796 | 10/2004 |
| WO | WO 04/096149 | 11/2004 |
| WO | WO 04/106356 | 12/2004 |
| WO | WO 05/003147 | 1/2005 |
| WO | WO 05/012327 | 2/2005 |
| WO | WO 05/020884 | 3/2005 |
| WO | WO 05/020885 | 3/2005 |
| WO | WO 05/021568 | 3/2005 |
| WO | WO 05/030258 | 4/2005 |
| WO | WO 05/042556 | 5/2005 |
| WO | WO 05/123087 | 12/2005 |
| WO | WO 06/002231 | 1/2006 |
| WO | WO 06/012078 | 2/2006 |
| WO | WO 06/012440 | 2/2006 |
| WO | WO 06/016930 | 2/2006 |
| WO | WO 06/037028 | 4/2006 |
| WO | WO 06/037227 | 4/2006 |
| WO | WO 06/063717 | 6/2006 |
| WO | WO 06/065335 | 6/2006 |
| WO | WO 06/097323 | 9/2006 |
| WO | WO 06/100087 | 9/2006 |
| WO | WO 06/121820 | 11/2006 |
| WO | WO 06/130532 | 12/2006 |
| WO | WO 07/011777 | 1/2007 |
| WO | WO 07/025304 | 1/2007 |
| WO | WO 01/032153 | 10/2008 |
| WO | WO 14/059901 | 4/2014 |
| WO | WO 14/059902 | 4/2014 |
| WO | WO 14/204831 | 12/2014 |

OTHER PUBLICATIONS

U.S. Appl. No. 11/005,443, filed Dec. 6, 2004, Gosselin, et al.
Advisory Action dated Aug. 8, 2007 from U.S. Appl. No. 11/005,443.
Advisory Action dated Dec. 9, 2010 from U.S. Appl. No. 11/527,124.
Afdhal, et al., Enhanced antiviral efficacy for valopicitabine pluc PEG-interferon in hepatitis C patients with HCV genotype-1 infection. Journal of Hepatology 2005, vol. 42, Supplement 2, p. 39-40.
Alt, M., et al., Core specific antisense phosphorothioate oligodeoxynucleotides as potent and specific inhibitors ofhepatitis C viral translation, Archives o/Virology, 142:589-599 (1997).
Alt, M., et al., Specific inhibition of hepatitis C viral gene expression by antisense phosphorothioate oligodeoxynucleotides, Hepatology, 22:707-717 (1995).
Altmann et ai, the synthesis of 1'-methyl carbocyclic thymidine and its effect on nucleic acid duplex stability, Synlett, Thieme Verlag, Stuttgart, De, 10:853-855 (1994).
Altmann, et al., The Effects of 2'- and 3'-Alkyl Substituents on Oligonucleotide Hybridization and Stability, Biorganic & Medicinal Chemistry Letter. 1994. 4. No. 16. 1969-74.
Altmann, et al., The Effects of 2'- and 3'-Alkyl Substituents on.
Arens, "Clinically relevant sequence-based genotyping of HBV, HCV, CMV, and HIV," Journal of Clinical Virology, 22:11-29 (2001).
Awano, et al., "Nucleosides and Nucleotides, Part 144 Synthesis and Antiviral Activity of 5-Substituted (2's)-2'-Deoxy-2'—C-Methylycytidines and -Urdines," Archiv Der Pharmazie, VCH Verlagsgesellschaft Mbh, Weinheim, DE, vol. 329, Feb. 1, 1996, (Feb. 1, 1996), pp. 66-72.
Baginski, S. G, et al., Mechanism of action of a pestivirus antiviral compound, PNAS USA, 97(14):7981-7986 (2000).
Battaglia, A.M. et al., Combination Therapy with Interferon and Ribavirin in the Treatment of Chronic Hepatitis C Infection", Ann. Pharmacother, 34:487-494 (2000)."
Beigelman et al., Functionally complete analogs of nucleosides. The use of D-glucose for the synthesis of 2-C-methyl-D-ribose derivatives and related nucleosides. Biorrganicheskaya Khimiya. 1986, vol. 12(10), pp. 1359-1365.
Beigelman et al., "New synthesis of 2'-C-methylnucleosides starting from D-glucose and D-ribose" Carbohydrate Res., 1987.166,.219-232.
Beigelman, L.N., et ai, A general method for synthesis of3'-C-alkylnucleosides, Nucleic Acids Symp. Ser., 9:115-118 (1981).
Beigelman, L.N., et ai, Epimerization during the acetolysis of 3-O-acetyl-5-O-benzoyl-1, 2-O-isopropylidene-3-C-methyl-α-D-ribofuranose. Synthesis of 3'-C-methylnucleosides with the β-D-ribo-and α-D-arabino configurations, Carbohydrate Research, 181:77-88 (1988).

(56) References Cited

OTHER PUBLICATIONS

Berenguer, M. et al., "Hepatitis C virus in the transplant setting," Antivir. Ther., 3 (Suppl 3):125-136 (1998).
Berenguer, M., et ai, Hepatitis Band C viruses: Molecular identification and targeted antiviral therapies, Proceedings ofthe Association ofAmerican Physicians, 110(2), 98-112 (1998).
Berman, E, et al., Synergistic cytotoxic effect of azidothymidine and recombinant interferon alpha on nonnal human bone marrow progenitor cells, Blood, 74(4): 1281-1286 (1989).
Bhat et al. (Oral Session V, Hepatitis C Virus, Flaviviridae, 2003 (Oral Session V, Hepatitis C Virus, Flaviviridae; 16th International Conference on Antiviral Research (Apr. 27, 2003, Savannah, Ga.); p. A75).
Bhopale, Girish Mahadeorao, et al., "Emerging drugs for chronic hepatitis C," Hepatology Research (2005), 32(3), 146-153.
Bianco A., et al. "Synthesis of a New Carbocyclic Nucleoside Analog", Tetrahedron Letters, 38(36):6433-6436, 1997.
Billich, et al., "Nucleoside Phosphotransferase from Malt Sprouts." Biol. Chem. Hoppe-Seyler, vol. 367, pp. 267-278, Apr. 1986.
Bio, et al., "Practical Synthesis of a Potent Hepatitis C Virus RNA Replication Inhibitor." Journal of Organic Chemistry (2004), 69(19), 6257-6266.
Bloch a., et al., "The Role of the 5'-Hydroxyl Group of Adenosine in Determining Substrate Specificity for Adenosine Deaminase," J. Med. Chem., 10(5):908-12 (Sep. 1967).
Browne, MJ., et al., "2', 3 '-didehydro-3 '-deoxythymidine (d4T) in patients with AIDS or AIDS-Related Complex: A Phase I trial," J. Infect. Dis., 167(1):21-29 (1993).
Bryant M.L., et al., "Antiviral L-Nucleosides Specific for Hepatitis B Virus Infection," Antimicrobial Agents and Chemotherapy, 45(1):229-235 (Jan. 2001).
Cappelacci ,et al. "Synthesis, Biological Evaluation, and Molecular Modeling of Ribose-Modified Adenosine Analogues as Adenosine Receptor Agonists." Journal of Medicinal Chemistry (2005), 48(5), 1550-1562.
Cappelacci, et al. "Ribose-modified nucleosides as ligands for adenosine receptors: Synthesis, conformational analysis, and biological evaluation of 1'—C-methyl denosine analogues," J. Med. Chem., vol. 45, 2002, pp. 1196-1202.
Carroll S.S., et al "Inhibition of hepatitis C virus RNA replication by 2'-modified nucleoside analogs," J. Biol. Chem., 278(14): 11979-11984 (2003).
Carroll, S.S., "Nucleoside analog inhibitors of hepatitis C virus replication," Infectious Disorders: Drug Targets (2006), 6(1), 17-29.
Cavelier, F., et al., "Studies of Selective Boc Removal in the Presence of Silyl Ethers," Tetrahedron Letters, 37: 5131-5134 (1996).
Chand, Pooran; et al., "Synthesis of (2S,3S,4R,5R)-2-(4- amino-5H-pyrrolo[3,2-d]pyrimidin-7-yl-5-(hydroxymethyl)-3-methylpyrrolidine-3,4-diol, an analog of potent HCV inhibitor." Collection Symposium Series (2005), 7(Chemistry of Nucleic Acid Components), 329-332.
Chen et al., Heterocycles, vol. 28, No. 2, 1989, pp. 593-601.
Chiacchio, et al., "Stereoselective synthesis of 2'-amino-2',3'dideoxynucleosides by nitron 1,3-dipolar cycloaddition: A new efficient entry toward d4T and its 2-methyl analougue," J. Org. Chem., vol. 64, 1999, pp. 28-36.
Chiaramonte, et al., "Inhibition of CMP-Sialic Acid Transport into Golgi Vesicles by Nucleoside Monophates." Biochemistry 2001, 40, 14260-14267.
Clark, et al., "Design, Synthesis, and Antiviral Activity of 2'-Deoxy-2'-fluoro-2'-C-methylcytidine, a Potent Inhibitor of Hepatitis C Virus Replication." Journal of Medicinal Chemistry (2005), 48(17), 5504-5508.
Clark, et al., Synthesis and antiviral activity . . . , Bioorganic & Medicinal Chemistry Letters, 16, 2006, 1712-1715.
Coelmont, Late, "Ribavirin antagonizes the in vitro anti-hepatitis C virus activity of 2'-C-methycytidine, the active component of valopicitabine," Antimicrobial Agents and Chemotherapy (2006), 50(10), 3444-3446.

Colacino, 1. M., Review article: "Mechanisms for the anti-hepatitis B virus activity and mitochondrial toxicity offialurdine (FIAU), " Antiviral Res., 29(2-3): 125-39 (1996).
Contreras, A.M. et al., "Viral RNA mutations are region specific and increased by ribavirin in a full-length hepatitis C virus replication system," J. Virol., 2002, 76(17): 8505-8517.
Cook, G.S., "Improving the treatment of hepatitis C infection in the UK," Expert Opinion on Pharmacotherapy, (2007) vol. 8, No. 2, pp. 183-191.
Cornberg, M., et al., "Present and future therapy for hepatitis C virus," Expert review of Anti-Infective Therapy, (2006) vol. 4, No. 5, pp. 781-793.
Cretton-Scott, E., et al., "Pharmacokinetics of B-L-2'-Deoxyctidine Prodrugs in Monkeys," Antiviral res., 50:A44 (2001).
Cui, L., et al., Cellular and molecular events leading to mitochondrial toxicity of 1-(2-deoxy-2-fluoro-1-I3-D-arabinofuranosyl)-5-iodouracil in human liver cells, J. Clin. Invest., 95:555-563.
Czernecki, S., et al, Synthesis of various 3'-branched 2', 3'-unsaturated pyrimidine nucleosides as potential anti-HIV agents J. Org. Chem., 57:7325-7328 (1992).
Czernecki, S., et al., "Synthesis of 2'-deoxy-2'-spirocyclopropyl cytidine as potential inhibitor of ribonucleotide diphosphate reductase," Can. J. Chem., vol. 71, 1993, pp. 413-416.
Dalpiaz, et al., "Temperature dependence of the affinity enhancement of selective adenosine A1 receptor agonism: a thermodynamic analysis." European Journal of Pharmacology (2002), 448(2-3), 123-131.
Daniels et al., "Tautomerism of Uracil and Thymine in Aqueous Solution: Spectroscopic Evidence", Proc. Nat. Acad. Sci. USA, vol. 69, No. 9, pp. 2488-2491, 1972.
Davis, G.L., "Current therapy for chronic Hepatitis C," Gastroenterology 118:S104-S114 (2000).
Davis, G.L., "New Therapies: Oral Inhibitors and Immune Modulators," Clinics in Liver Disease, (2006) vol. 10, No. 4, pp. 867-880.
Davisson, V.J., et al., "Synthesis of Nucleotide 5'-Diphosphates from 5'-O-Tosyl Nucleosides," J. Org. Chem., 52(9):1794-1801 (1987).
De Francesco, R., et al., Approaching a new era for hepatitis C virus therapy: Inhibitors of the NS3-4A serine protease and the NS5B RNA-dependent RNA polymerase, Antiviral Research, 58:1-16 (2003).
De Lombaert, S., et al., N-Phosphonomethyl dipeptides and their phosphonate prodrugs a new generation of neutral endopeptidase (NEP, EC 3.4.24.11) inhibitors, J. Med. Chem., 37:498-511 (1994).
Ding, et al., "Synthesis of 2'-b-C-methyl toyocamycin and sangivamycin analogs as potential HCV inhibitors." Bioorganic & Medicinal Chemistry Letters (2005), 15(3), 725-727.
Ding, et al., "Synthesis of 9-(2-b-C-methyl-b-D-ribofuranosyl)-6-substituted purine derivatives as inhibitors of HCV RNA replication." Bioorganic & Medicinal Chemistry Letters (2005), 15(3), 709-713.
Dornsife, R. E. et al., In Vitro Potency of Inhibition by Antiviral Drugs of Hematopoietic Progenitor Colony Formation Correlates with Exposure at Hemotoxic Levels in Human Immunodeficiency Virus-Positive Humans" Antirnicrob. Agents Chemother. 40(2):514-519 (1996)".
Dutartre, H., et al., "General catalytic deficiency of hepatitis C virus RNA polymerase with an S282T mutation and mutually exclusive resistance towards 2'-modified nucleotide analogues," Antimicrobial Agents and Chemotherapy, (2006) vol. 50, No. 12, pp. 4161-4169.
Dymock, B.W., et al., Review: Novel approaches to the treatment of hepatitis C virus infection Antiviral Chemistry & Chemotherapy, 11(2):79-96 (2000).
Eldrup et al. (Oral Session V, Hepatitis C Virus, Flaviviridae; 16th International Conference on Antiviral Research (Apr. 27, 2003, Savannah, Ga.).
Eldrup et al., "Structure-Activity Relationship of Heterobase-Modified 2'-C-Methyl Ribonucleosides as Inhibitors of Hepatitis C Virus RNA Replication." Department of Medicinal Chemistry, Isis Pharmaceuticals, Carlsbad, CA, USA. Journal of Medicinal Chemistry (2004), 47(21), 5284-5297.

(56) References Cited

OTHER PUBLICATIONS

Eldrup, et al., "Structure-Activity Relationship of Purine Ribonucleosides for Inhibition of Hepatitis C Virus RNA-Dependent RNA Polymerase.", Department of Medicinal Chemistry, Isis Pharmaceuticals, Carlsbad, CA, USA. Journal of Medicinal Chemistry (2004), 47(9), 2283-2295.

Faivre-Buet, V., et al, Synthesis of 1'-deoxypsicofuranosyl-deoxynucleosides as potential anti-HIV agents Nucleosides & Nucleotides, 11(7): 1411-1424 (1992).

Farkas, J., et al., "Nucleic acid components and their analogues. LXXIX. Synthesis of methyl 1-deoxy-D-psicofuranosides substituted at C(1) with halo atoms or a mercapto group," Collect. Czech.Chern. Commun., 31:1535-1543 (1996).

Farkas, J., et al., Nucleic acid components and their analogues. XCIV. Synthesis of 6-amino-9-(1-deoxy-I3-D-psicofuranosyl) purine, Collect. Czech. Chem. Comrnun. 32:2663-2667 (1967).

Farquhar et al., "Biologically reversible phosphate-protective groups," J. Phurm. Sci., 1983, 72(3): 324.

Farquhar, D., et al., "Synthesis and biological evaluation of 9-[5'-(2-oxo-1,3,2-oxazaphosphorinan-2-yl)-I3-D-arabinosyl]adenine and 9-[5'-(2-oxo-1,3,2-dioxazaphosphorinan-2-yl)-I3-D-arabinosyl]adenine: Potential neutral precursors of 9-[I3-D-arabinofuranosyl]adenine 5'-monophosphate," J. Med. Chem., 28:1358-1361 (1985).

Farquhar, D., et al., "Synthesis and biological evaluation of neutral derivatives of 3-fluoro-2'-deoxyuridine 5'-phosphate," J. Med. Chem. ,26: 1153-1158 (1983).

Feast, A.A.J., et al., "Studies on the D-Glucosaccharinic Acids," Acta Chemica Scandinavica 19(5):1127-1134 (1965).

Fedorov, 1.1., et al, "31-C-Branched 2'-deoxy-5-methyluridines: Synthesis, enzyme inhibition, and antiviral properties," J. Med. Chem., 35(24):4567-4575 (1992).

Ferrari R, et al., "Characterization of soluble hepatitis C virus RNA-dependent RNA polymerase expressed in *Escherichia coli*," Journal a/Virology, 73(2),1649-1654 (1999).

Fischl, M.A., et al., "Zalcitabine compared with zidovudine in patients with advanced HIV-1 infection who received previous zidovudine therapy," Ann. Intern. Med., 18(10):762-769 ( 1993).

Fox, J. J., et al., "Thiolation of nucleosides. II. Synthesis of 5-methyl-2'-deoxycytidine and related pyrimidine nucleosides," J. Am. Chem. Soc., 81: 178-187 (Jan. 5, 1959).

Francesco, et al. Antiviral Research 58 (2003) 1-16.

Franchetti, et al., "Antitumor Activity of C-Methyl-b-D-ribofuranosyladenine Nucleoside Ribonucleotide Reductase Inhibitors." Journal of Medicinal Chemistry (2005), 48(15), 4983-4989.

Franchetti, P., et al., "2'-C-Methyl analogues of selective adenosine receptor agonists: synthesis and binding studies," J. Med. Chern., 41(10):1708-1715 (1998).

Freed, J.J., et al., "Evidence for acyloxymethyl esters of pyrimidine 5'-deoxyribonucleotides as extracellular sources of ative 5'-deoxyribonucleotides in cultured cells," Biochemical Phannacology 38:3193-3198 (1989).

Fujimori, et al., "A Convenient and Stereoselective Synthesis of 2'-Deoxy-[beta]-L-nucleosides," Nucleosides & Nucleotides, 11(2-4), 341-349 (1992); only CAPLUS abstract supplied.

Furukawa, Y., et al "A novel method for synthesis of purine nucleosides using Friedel-Crafts catalysts," Chem. Pharm. Bull., 16(6):1076-1080 (Jun. 1968).

Galderisi, V., eta!., "Antisense oligonucleoties as therapeutic agents," Journal of Cellular Physiology, 181 (2):251-257 (Nov. 1999).

Gallo, et al., "2'-C-Methyluridine Phosphoramidite: A New Building Block for the Preparation of RNA Analogues Carrying the 2'-hydroxyl Group." Tetrahedron, 57 (2001), 5707-5713.

Gerotto, et al., Effect of retreatment with interferon alone or interferon plus ribavirin on hepatitis C virus quasispecies diversification in nonresponder pateinets with chronic hepatitis C. Journal of Virology, Sep. 1999, vol. 73, No. 9, p. 7241-7247.

Giradet, et al., "Synthesis and Cytotoxicity of 4-Amino-5-oxopyrido[2,3-d]pyrimidine Nucleosides." Journal of Medicinal Chemistry (2000), 43(20), 3704-3713.

Gretch, D.R., "Use and interpretation of HCV diagonostic tests in the clinical setting." Clinics in Live Disease, Nov. 1997, vol. 1, No. 3, pp. 547-557.

Grouiller et al., "Structural studies on a psicofuranosyl nucleoside, a potential antiviral agent." J. Pharm. Belg., 47(4), 381-3 (1992).

Grouiller, A., et al., "Novel p-to luenesulfonylation and thionocathonylation of unprotected thymine nucleosides," Synlett, 1993,221-222 (Mar. 1993).

Grunnagel, et al., "Preparation of D-Tagatose." Justus Liebigs Annalen der Chemie (1969), 721: 234-5.

Gunic, E., et al., "Synthesis and cytotoxicity of 4'-C-and 5'-C-substituted Toyocamycins," Bioorg. Med. Chem., 9:163-170 (2001).

Haraguchi, K, et al., "Stereoselective synthesis of 1'-C-branched uracil nucleosides from uridine," Nucleosides & Nucleotides, 14(3-5):417-420 (1995).

Haraguchi, K, et al., "Preparation and reactions of 2'- and 3'-vinyl bromides of uracil nucleosides: Versatile synthons for anti-HIV agents," Tetrahedron Letters, 32(28):3391-3394 (1991).

Harry-O'Kuru, RE., et al., "2'-C-Alkylribonucleosides: Design, synthesis, and conformation," Nucleosides & Nucleotides, 16(7-9):1457-1460 (1997).

Harry-O'Kurv, Re., et al., "A short, flexible route toward 2'-C-branched ribonucleosides", J.Org. Chern., 62:1754-1759 (1997). (Scheme 11).

Hassan, et al., "Nucleosides and Nucleotides 151: Conversion of (Z)-2'-(Cyanomethylene)-2'-Deoxyuridines into their (E)-Isomers via Addition of Thiophenol to the Cyanomethylene Moiety Followed by Oxidative Syn-elimination Reactions." J. Org. Chem., vol. 61, 1996, pp. 6261-6267.

Hassan, et al., "Nucleosides and Nucleotides 156: Chelation-Controlled and Nonchelation-Controlled Diastereofacial Selective Thiophernol Addition Reactions at the 2'-Position of 2'-[(Alkoxycarbonyl)methaylene]-2'-deoxyuridines: Conversion of (Z0-2'[(Alkoxycarbonyl)methylene]-2'-Deoxyuridines into their (E)-Isomers" J. Org. Chem., vol. 62, 1997, pp. 11-17.

Hattori, H. et al., "Nucleosides and Nucleotides 158" *Journal of Medicinal Chemistry, American Chemical Society*, vol. 39, 1996, pp. 5005-5001.

Hattori, H., et al, "Nucleosides and nucleotides. 175. Structural requirements of the sugar moiety for the antitumor activities of new nucleoside antimetabolites, 1-(3-C-ethynyl-b-D-ribopentofuranosyl) cytosine and -uracil," J. Med. Chem., 41 :2892-2902 (1998).

Hayakawa, et al., "Reaction of organometallic reagents with 2'- and 3'-ketouridine derivatives: synthesis of uracil nucleosides branched at the 2'- and 3'-positions." Chemical & Pharmaceutical Bulletin (1987), 35(6), 2605-8.

Hoard, D.E., et al., "Conversion of Mono- and Oligodeoxyribonucleotides to 5'-Triphosphates," J. Am Chem. Soc., 87(8):1785-1788 (Apr. 20, 1965).

Hodge, et al., "Amadori Rearrangement Products." Methods in Carbohydrate Chemistry (1963), 2: 99-107.

Holy, A., "Nucleic Acid Components and Their Analogs. CLIII. Preparation of 2'-deoxy-L-Ribonucleosides fo the Pyrimidine Series," Collect. Czech Chem. Commun., 37(12): 4072-4087 (1972).

Hossain, et al., "Synthesis of 2'- and 3'-Spiro-isoxazolidine Derivatives of Thymidine & Their Conversions to 2',3'-dideoxy-2', 3'-didehydro-3'-C-substituted nucleosides by Radical Promoted Fragmentation," Tetrahedron vol. 49, No. 44, pp. 10133-10156, (1993).

Hostetler, KY., et al., "Greatly enhanced inhibition of Human Immunodeficiency Virus Type I replication in CEM and HT4-6C cells by 3'-deoxythymidine diphosphate dimyristoylglycerol, a lipid prodrug of 3'-deoxythymidine," Antirnicrob. Agents Chernother., 36:2025-2029 (Sep. 1992).

Hostetler, KY., et al., "Synthesis and antiretroviral activity of phospholipids analogs of azidothymidine and other antiviral nucleosides," J. BiD!. Chern., 265:6112-6115 (1990).

Hrebabecky, H., et al. "Synthesis of 7- and 9 13-D-psicofuranosylguanine and their 1'-deoxy derivatives," Collect. Czech. Chern. Commun., 39:2115-2123 (1974).

Hrebabecky, H., et al., "Nucleic acid components and their analogues. CXLIX. Synthesis of pyrimidine nucleosides derived from 1-deoxy-D-psicose," Collect. Czech. Chern. Commun., 37:2059-2065 (1972).

(56) References Cited

OTHER PUBLICATIONS

Hu, et al., Viral, host and interferon-related factors modulating the effect of interferon therapy for hepaptitis C virus infection. Journal of Viral Hepatitis, 2001, vol. 8, p. 1-18.
Hunston, RN., et al., "Synthesis and biological properties of some cyclic phosphotriesters drived from 2'-deoxy-5-fluorouridine," J. Med. Chem. 27:440-444 (1984).
Iglesias, et al., "Complete and Regioselective Deacetylation of Peracetylated Uridines Using a Lipase." Biotechnology Letters 22: 361-365, 2000.
Iimori, et al., "2'-C-, 3'-C-, and 5'-C-Methylsangivamycins: conformational lock with the methyl group." Tetrahedron Letters (1991), 32(49), 7273-6.
Iimori, et al., "A study on conformationally restricted sangivamycins and their inhibitory abilities of protein kinases " Nucleic Acids Symposium Series (1992), 27(Nineteenth Symposium on Nucleic Acids Chemistry, 1992), 169-70.
Iino, T., et al., "Nucleosides and nucleotides. 139. Stereoselective synthesis of (2'S)-2'-C-alkyl-2'-deoxyuridines," Nucleosides and Nucleotides, 15(1-3):169-181 (1996).
Ikegashira, K., et al., "Discovery of conformationally constrained tetracylic compounds as potent hepatitis C virus NS5B RNA polymerase inhibitors," Journal of Medicinal Chemistry, (Nov. 30, 2006) vol. 449, No. 24, pp. 6950-6953.
Imai, K., et al., "Studies on Phosphorylation. IV. Selective Phosphorylation of the Primary Hydroxyl Group in Nucleosides." J. Org. Chem., 34(6): 1547-1550 (Jun. 1969).
Itoh, Y., et al, "Divergent and stereocontrolled approach to the synthesis of uracil nucleosides branched at the anomeric position," 1. Org. Chern., 60(3):656-662 (1995).
Johnson, C.R., el al, "3'-C-Trifluoromethyl ribonucleosides," Nucleosides & Nucleotides, 14(1&2):185-194 (1995).
Jones, G. H.; Moffatt, J. G., Methods in Carbohydrate Chemistry; Whisler, R. L. and Moffatt, 1. L. Eds; Academic Press: New York, 1972; 315-322.
Jones, G. n., et al., "4 '-substituted nucleosides. 5. Hydroxymethylation of nucleoside 5'-aldehydes," J. Org. Chem.~44:1309-1317 (1979).
Kakefuda, et al., "Nucleosides and nucleotides. 120. Stereoselective radical deoxygenation of tert-alcohols in the sugar moiety of nucleosides: synthesis of 2',3'-dideoxy-2'-C-methyl- and -2'-C-ethynyl-b-D-threo-pentofuranosyl pyrimidines and adenine as potential antiviral and antitumor agents." Tetrahedron (1993), 49(38), 8513-28.
Kamaike, K., et al., "An efficient method for the synthesis of [4-15N]cytidine, 2'-deoxy[4-15N]cytidine, ]6-15N]adenosine, and 2'-deoxy[6-15N]adenosine derivatives," Nuclesodies and Nucleotides, 15(1-3): 749-769 (1996).
Kaneko, M., et al., "A convenient synthesis of cytosine nucleosides," Chem. Pharm. Bull., 20:1050-1053 (1972).
Kawana, M., et al., "The deoxygenation oftosylated adenosine derivatives with Grignard reagents," Nucleic Acids Symp. Ser., 17:37-40 (1986).
Kempe, T., et al., "Selective 2'-Benzoylation at the Cis 2', 3'-diols of Protected Ribonucleosides. New Solid Phase Synthesis of RNA and DNA-RNA Mixtures," Nucleic Acids Res., 10(21):6695-6714 (Nov. 11, 1982).
Kerr, S.G., et al., "N-(Dialkylamino)Methylene Derivatives of 2'-Deoxycytidine and Arabinocytidine: Physicochemical Studies for Potential Prodrug Applications," J. Pharm. Sci., 83(4): 582-586 (Apr. 1994).
Khamnei, S., "Neighboring group catalysis in the design of nucleotide prodrugs," 1. Med. Chern., 39:4109-4115 (1996).
Kim, et al., "A Novel Nucleoside Prodrug-Activating Enzyme: Substrate Specificity of Biphenyl Hydrolase-like Protein," Molecular Pharmaceutics (2004), 1(2), 117-127.
Klumpp, et al., "The Novel Nucleoside Analog R1479 (4'-Azidocytidine) is a Potent Inhibitor of NS5B-dpendent RNA Synthesis and Hepatits C Virus Replication in Cell Culture." the Journal of Biological Chemistry, vol. 281, No. 7, pp. 3793-3799, Feb. 17, 2006.

Kohn, et al., "A new method for the synthesis of furanose derivatives of aldohexoses," *J Am. Chem. Soc.*, 1965, 87(23): 5475-80.
Kotra, L., et al., "Structure-Activity Relationships of 2'-Deoxy-2',2'-difluoro-L-erythro-pentofuranosyl Nucleosdes." J. Med. Chem. 1997, 40, 3635-3644.
Kucera, L. S., et al., "Novel membrane-interactive ether lipid analogs that inhibit infectious HIV-1 production and induce defective virus formation, " AIDS Res. Hum. Retro Viruses, 6:491-501 (1990).
Kuhn, R., et al., "Uber eine molekulare Umlagerung von N-Glucosiden." Jahrg. 69, 1936, p. 1745-1754.
Kurtzberg J., et al., "Differential toxicity of carbovir and AZT to human bone marrow hematopoietic progenitor cells in vitro," Exp. Hematal., 18(10): 1094-1096 (1990).
Lai, V.C.H., et al., "Mutational analysis of bovine viral diarrhea virus RNA-dependent RNA polymerase," 1. Viral., 73(12):10129-10136 (Dec. 1999).
Landowski, "Nucleoside ester prodrug substrate specificity of liver carboxylesterase," Journal of Pharmacology and Experimental Therapeutics (2006), 316(2), 572-580.
Lavaire, S., et al., "3'-Deoxy-3'-C-trifluoromethyl nucleosides: Synthesis and antiviral evaluation," Nucleosides & Nucleotides, 17(12):2267-2280 (1998).
Le Pogam, et al., "In Vitro Selected Conl Subgenomic Replicons Resistant to 2'-C-Methyl-Cytidine or to R1479 Show Lack of Cross Resistance." Virology 351 (2006), 349-359.
Le Pogam, et al., "Selection and Characterization of Replicon Variants Dually Resistant to Thumb- and Palm-Binding Non-nucleoside Polymeras Inhibitors of the Hepatitis C Virus." Journal of Virology, vol. 80, No. 12, Jun. 2006, p. 6146-6154.
Leonard, N. J., et al., "5-Amino-5-deoxyribose derivatives. Synthesis and use in the preparation of "reversed" nucleosides" J. Helerocycl. Chem., 3:485-489 (Dec. 1966).
Lerza, R, et al., "In vitro synergistic inhibition ofhuman bone marrow hemopoietic progenitor growth by a 3'-azido-3'-deoxy-thymidine, 2',3'-dideoxycytidine combination," Exp. Hematal., 25(3):252-255 (1997).
Lewis W, et al., "Zidovudine induces molecular, biochemical, and ultrastructural changes in rat skeletal muscle mitochondria," J. Clin. Invest., 89(4):1354-1360 (1992).
Lewis, L. D., et al., "Ultrastructural changes associated with reduced mitochondrial DNA and impaired mitochondrial function in the presence of 2'3'-dideoxycytidine," Antimicrob. Agents Chemother., 36(9):2061-2065 (1992).
Lewis, W., et al., "Fialuridine an dits metabolites inhibit DNA polymerase y at sites of multiple adjacent analog incorporation, decrease mtDNA abundance, and cause mitochondrial structural defects in cultured hepatoblasts," Proceedings of the National Academy ofSciences, USA, 93(8): 3592-7 (1996).
Leyssen, P. et al., "Perspectives for the treatment of infections with Flaviviridae," Clinical Microbiology Reviews (Washington, D.C.), 13(1):67-82 (Jan. 2000). ;'..;•-/k 96,,, J.
Li, et al., "2'—C-Branched ribonucleosides. 2. Synthesis of 2'—C-beta-trifluormethyl pyrimidine ribonucleosides," Org. Lett., vol. 3, 2001, pp. 1025-1028.
Lin, T.S., et al., "Synthesis of Several Pyrimidine L-Nucleoside Analogues as Potential Antiviral Agents," Tethrahedron Letters, 51(4): 1055-1068 (1995).
Lohmann V., et al., "Biochemical and kinetic analyses ofNS5B Rna-dependent Rna polymerase of the Hepatitis C virus," Virology, 249, 108-118 (1998).
Lohmann, V., et al., "Replication of subgenomic hepatitis C virus RNAs in a hepatoma cell line," Science, 285(5424):110-113 (Jul. 2, 1999).
Lopez Aparicio, F.J., et al., "Synthesis of Saccarinic Acid Derivatives," Carbohydrate Res., 129:99 (1984).
Lopez-Herrera, F.J., et al., "A New Synthesis of 2-C Methyl-D-Ribono-1, 4-Lactone and the C-(/C-13 Fragment of Methynolide," J. Carbohydrate Chemistry, 13(5): 767-775 (1994).
Luh, T.-Y., et al., "A convenient method for the selective esterification of amino-alcohols," Synthetic Communications, 8(5):327-333 (1978).

(56) References Cited

OTHER PUBLICATIONS

Maga, Giovanni, et al., Lack of stereospecificity of suid pseudorabies virus thymidine kinase, Biochem. J., 294(2): 381-385 (1993).
Mahmoudian, M., et al., "A Versatile Procedure for the Generation of Nucleoside 5'-Carboxylic Acids Using Nucleoside Oxidase," Tetrahedron, Elsevier Science Publishers Amsterday, NL, vol. 54, No. 28, 8171-8182 Jul. 9, 1998.
Mansour, T.S., et al., "Editorial," Anti-Ineffective Agents in Medicinal Chemistry, (2007) vol. 6, No. 1, pp. 1.
Markland W., et al., "Broad-spectrum antiviral activity of the IMP dehydrogenase inhibitor VX-497: a comparison with ribavirin and demonstration of antiviral additivity with alpha interferon," Antimicrobial Agents and Chemotherapy, Apr. 2000, vol. 44, No. 4, pp. 859-866.
Martin, J.A., et al., "Synthesis and antiviral activity of monofluoro and difluoro analogues of pyrimidine dexoyribonucleosides against human immunodeficiency virus (HIV-1)", J. Med. Chem., 33(8):2137-2145 (1990).
Martin, X., et al., "Intramolecular hydrogen bonding in primary hydroxyl of thymine 1-(I-deoxy-β-D-psicofuranosyl) nucleoside," Tetrahedron, 50(22):6689-6694 (1994).
Matsuda, A., et al., "Alkyl addition reaction ofpyrimidine 2'-ketonucleosides: Synthesis of 2'-branched-chain sugar pyrimidine nucleosides (Nucleosides and Nucleotides. LXXXI)," Chem. Pharm. Bull., 36(3):945-953 (1988).
Matsuda, A., et al., "Nucleosides and Nucleotides. 104. Radical and palladium-catalyzed deoxygenation of the allylic alcohol systems in the sugar moiety ofpyrimidine nucleosides," Nucleosides & Nucleotides, 11(2/4):197-226 (1992).
Matsuda, A., et al., "Nucleosides and Nucleotides. 94. Radical deoxygenation of tert-alcohols in 1-(2-C-alkylpentofuranosyl)pyrimidines: Synthesis of (2'5)-2'-deoxy-2'-C-methylcytidine, an antileukemic nucleoside," J. Med. Chem., 34:234-239 (1991).
Matsuda, A., et al., "Radical deoxygenation oftert-alcohols in 2'-branched-chain sugar pyrimidine nucleosides: Synthesis and antileukemic activity of 2'-deoxy-2 '(S)-methylcytidine," Chem. Pharm. Bull., 35(9):3967-3970 (1987).
McCormick, J., et al., "Structure and total synthesis ofHF-7, a neuroactive glyconucleoside disulfate from he funnel-web spide HoZoZena curta," J. Am. Chem. Soc., 121(24),5661-5665 (1999).
McFarlin, et al., J. Am. Chem. Soc. 1958, 80, 5372-76.
McKenzie, R, et al., "Hepatic failure and lactic acidosis due to fialuridine (HAU), an investigational nucleoside analogue fOT chronic hepatitis B", N. Engl. J. Med., 333(17):1099-1105 (1995).
Medina, D. J., et al., "Comparison of mitochondrial morphology, mitochondrial DNA content, and cell viability in cultured cells treated with three anti-Human Immunodeficiency Virus dideoxynucleosides," Antimicrob. Agents Chemother., 38(8):1824-8 (1994).
Meier, c., et al., "Cyclic saligenyl phosphotriesters of 2',3'-dideoxy-2',3'-didehydrothymidine (d4T)—A new pro-nucleic approach." Bioorganic & Med. Chem. Letters 7(2):99-104 (1997).
Meyer, R.B., Jr., et al., "2'-O-Acyl-6-thioinosine cyclic 3',5'-phosphates as prodrugs of thioinosinic acid," J. Med. Chem. 22: 811-815 (1979).
Mikhailov, S.N., et al., "Substrate properties ofC'-methylnucleoside and C'-methyl-2'-deoxynucleoside 5'-triphosphates in RNA and DNA synthesis reactions catalysed by RNA and DNA polymerases," Nucleosides & Nucleotides, 10(1-3):339-343 (1991).
Mikhailov, S.N., et al., "Synthesis and properties on'C-methylnucleosides and their phosphoric esters," Carbohydrate Research, 124:75-96 (1983).
Mikhailov, S.N., et al, "Hydrolysis of 2'- and 3'-C-methyluridine 2', 3'-cyclic monophosphates and interconversion and dephosphorylation of the resulting 2'- and 3'-monophosphates: Comparison with the reactions of uridine monophosphates," J. Org. Chem., 57 (15):4122-4126 (1992).
Miles, et al., "Circular Dichroism of Nucleoside Derivatives. IX. Vicinal Effects on the Circular Dichrosim of Pyrimidine Nucleosides." J. Am. Chem. Soc. 92(13): 3872-3881 (1970).
Moiseyev, et al., "Determination of the nucleotide conformation in the productive enzyme-substrate complexes of RNA-depolymerases." FEBS Letters (1997), 404(2,3), 169-172.
Moore, et al., "Synthesis of Nucleotide Analogues That Potently and Selectively Inhibit Human DNA Primase." Biochemistry (2002), 41(47), 14066-14075.
Murai, et al., "A synthesis and an x-ray analysis of 2'-C-,3'-C- and 5'-C-methylsangivamycins," Heterocycles (1992), 33(1), 391-404.
Neidlein, R, et aZ., "Mild preparationof 1-benzyloxyiminoalkylphosphonic dichlorides: Application to the synthesis of cyclic phosphoric diesters and cyclic monoester amides," Heterocycles 35:1185-1203 (1993).
Nishiguchi, S., et al., "Methods to Detect Substitutions in the Interferon-Sensitivity-Determining Region of Hepatitis C virus 1b for Prediction of Response to Interferon Therapy," Hepatology. Jan. 2001, vol. 33, No. 1, pp. 241-247.
Nishimura, T. et al. "Studies on Sythetic Nuclesides. Trimethylsilyl Derivatives of Pyrmidine and Purines," Chemical & Pharmaceutical Bulletin (1964), vol. 12, pp. 352-356.
Notice of Allowance dated Apr. 7, 2009 from U.S. Appl. No. 10/608,907.
Notice of Allowance dated Apr. 7, 2009 from U.S. Appl. No. 10/609,298.
Notice of Allowance dated Aug. 22, 2007 from U.S. Appl. No. 11/005,447.
Notice of Allowance dated Aug. 22, 2007 from U.S. Appl. No. 11/005,467.
Notice of Allowance dated Aug. 22, 2007 from U.S. Appl. No. 11/005,470.
Notice of Allowance dated Aug. 8, 2006 from U.S. Appl. No. 11/005,473.
Notice of Allowance dated Dec. 27, 2005 from U.S. Appl. No. 10/602,693.
Notice of Allowance dated Dec. 27, 2005 from U.S. Appl. No. 10/602,694.
Notice of Allowance dated Dec. 28, 2005 from U.S. Appl. No. 10/602,692.
Notice of Allowance dated Feb. 12, 2007 from U.S. Appl. No. 11/005,447.
Notice of Allowance dated Feb. 19, 2004 from U.S. Appl. No. 09/864,078.
Notice of Allowance dated Jan. 27, 2010 from U.S. Appl. No. 10/715,729.
Notice of Allowance dated Jan. 8, 2008 from U.S. Appl. No. 11/005,441.
Notice of Allowance dated Jun. 11, 2009 from U.S. Appl. No. 11/516,928.
Notice of Allowance dated Jun. 15, 2009 from U.S. Appl. No. 10/602,691.
Notice of Allowance dated Jun. 22, 2007 from U.S. Appl. No. 11/005,441.
Notice of Allowance dated Jun. 23, 2004 from U.S. Appl. No. 09/863,816.
Notice of Allowance dated Jun. 24, 2010 from U.S. Appl. No. 10/715,729.
Notice of Allowance dated Mar. 30, 2009 from U.S. Appl. No. 11/005,445.
Notice of Allowance dated Mar. 7, 2007 from U.S. Appl. No. 11/005,470.
Notice of Allowance dated Mar. 9, 2006 from U.S. Appl. No. 10/602,136.
Notice of Allowance dated May 17, 2005 from U.S. Appl. No. 10/602,135.
Notice of Allowance dated Oct. 11, 2006 from U.S. Appl. No. 11/005,447.
Notice of Allowance dated Oct. 12, 2006 from U.S. Appl. No. 11/005,470.
Notice of Allowance dated Oct. 13, 2005 from U.S. Appl. No. 10/602,976.

(56) References Cited

OTHER PUBLICATIONS

Notice of Allowance dated Sep. 17, 2009 from U.S. Appl. No. 11/005,445.
Notice of Allowance dated Sep. 24, 2009 from U.S. Appl. No. 11/644,304.
Novak, J.J.K. & Sorm, F., "Nucleic Acid Components and Their Analogues. CXX. 2-C-Methyl-D-Ribose and Its Derivatives," Collection Czechoslay. Chem. Commun., 34:857-866 (1969).
Novak, J.J.K.; "Chiroptical Properties of 2-Methyl-1,4-Lactones; Revised Absolute Configuration of 2-Deoxy-2-C-Methyl-Eiythro-D-Pentono-1, 4-Lactones," Collection Czechoslay. Chem. Commun., 39:869-882 (1974).
Nutt, R.F., et al., "Branched-chain sugar nucleosides. III. 3'-C-methyladenine", J.Org. Chem., 33:1789-1795 (1968).
Office Action dated Jan. 28, 2008 from U.S. Appl. No. 10/608,907.
Office Action dated May 31, 2007 from U.S. Appl. No. 10/608,907.
Office Action dated Aug. 15, 2006 from U.S. Appl. No. 10/608,907.
Office Action dated Apr. 5, 2005 from U.S. Appl. No. 10/602,135.
Office Action dated Apr. 5, 2005 from U.S. Appl. No. 10/602,692.
Office Action dated Apr. 6, 2005 from U.S. Appl. No. 10/602,693.
Office Action dated Apr. 6, 2005 from U.S. Appl. No. 10/602,694.
Office Action dated Aug. 16, 2007 from U.S. Appl. No. 10/715,729.
Office Action dated Aug. 18, 2006 from U.S. Appl. No. 11/005,467.
Office Action dated Aug. 2, 2006 from U.S. Appl. No. 10/609,298.
Office Action dated Aug. 20, 2007 from U.S. Appl. No. 11/005,446.
Office Action dated Aug. 21, 2006 from U.S. Appl. No. 11/005,441.
Office Action dated Aug. 22, 2007 from U.S. Appl. No. 10/602,691.
Office Action dated Aug. 27, 2003 from U.S. Appl. No. 09/864,078.
Office Action dated Aug. 7, 2006 from U.S. Appl. No. 11/005,442.
Office Action dated Dec. 10, 2008 from U.S. Appl. No. 10/602,142.
Office Action dated Dec. 23, 2008 from U.S. Appl. No. 10/715,729.
Office Action dated Dec. 29, 2006 from U.S. Appl. No. 10/602,691.
Office Action dated Dec. 5, 2006 from U.S. Appl. No. 11/005,440.
Office Action dated Dec. 5, 2006 from U.S. Appl. No. 11/005,444.
Office Action dated Dec. 5, 2006 from U.S. Appl. No. 11/005,446.
Office Action dated Dec. 5, 2006 from U.S. Appl. No. 11/005,472.
Office Action dated Feb. 26, 2008 from U.S. Appl. No. 10/602,142.
Office Action dated Feb. 26, 2008 from U.S. Appl. No. 10/602,691.
Office Action dated Feb. 26, 2008 from U.S. Appl. No. 11/005,445.
Office Action dated Feb. 28, 2008 from U.S. Appl. No. 11/005,471.
Office Action dated Jan. 5, 2011 from U.S. Appl. No. 12/504,601.
Office Action dated Jul. 10, 2008 from U.S. Appl. No. 10/609,298.
Office Action dated Jul. 17, 2008 from U.S. Appl. No. 11/005,445.
Office Action dated Jul. 18, 2007 from U.S. Appl. No. 11/005,469.
Office Action dated Jul. 18, 2007 from U.S. Appl. No. 11/005,471.
Office Action dated Jul. 21, 2010 from U.S. Appl. No. 11/527,124.
Office Action dated Jul. 28, 2006 from U.S. Appl. No. 10/602,142.
Office Action dated Jul. 7, 2009 from U.S. Appl. No. 10/715,729.
Office Action dated Jun. 13, 2007 from U.S. Appl. No. 11/005,440.
Office Action dated Jun. 13, 2007 from U.S. Appl. No. 11/005,444.
Office Action dated Jun. 13, 2007 from U.S. Appl. No. 11/005,466.
Office Action dated Jun. 13, 2007 from U.S. Appl. No. 11/005,472.
Office Action dated Jun. 14, 2007 from U.S. Appl. No. 11/005,468.
Office Action dated Mar. 12, 2007 from U.S. Appl. No. 11/005,443.
Office Action dated Mar. 17, 2008 from U.S. Appl. No. 11/005,446.
Office Action dated Mar. 24, 2008 from U.S. Appl. No. 11/005,469.
Office Action dated Mar. 29, 2007 from U.S. Appl. No. 10/602,142.
Office Action dated May 16, 2007 from U.S. Appl. No. 11/005,442.
Office Action dated May 19, 2005 from U.S. Appl. No. 10/602,976.
Office Action dated May 30, 2006 from U.S. Appl. No. 10/602,691.
Office Action dated May 30, 2008 from U.S. Appl. No. 10/715,729.
Office Action dated Nov. 15, 2005 from U.S. Appl. No. 10/602,142.
Office Action dated Nov. 20, 2006 from U.S. Appl. No. 11/005,466.
Office Action dated Nov. 24, 2009 from U.S. Appl. No. 11/527,124.
Office Action dated Nov. 25, 2005 from U.S. Appl. No. 11/005,473.
Office Action dated Nov. 26, 2008 from U.S. Appl. No. 10/608,907.
Office Action dated Nov. 28, 2007 from U.S. Appl. No. 11/005,442.
Office Action dated Nov. 7, 2005 from U.S. Appl. No. 10/602,691.
Office Action dated Oct. 1, 2003 from U.S. Appl. No. 09/863,816.
Office Action dated Oct. 12, 2005 from U.S. Appl. No. 11/005,444.
Office Action dated Oct. 12, 2005 from U.S. Appl. No. 11/005,466.
Office Action dated Oct. 12, 2005 from U.S. Appl. No. 11/005,472.
Office Action dated Oct. 16, 2007 from U.S. Appl. No. 11/005,440.
Office Action dated Oct. 2, 2007 from U.S. Appl. No. 11/005,468.
Office Action dated Oct. 2, 2009 from U.S. Appl. No. 11/516,928.
Office Action dated Oct. 5, 2005 from U.S. Appl. No. 11/005,440.
Office Action dated Oct. 5, 2005 from U.S. Appl. No. 11/005,443.
Office Action dated Oct. 5, 2005 from U.S. Appl. No. 11/005,446.
Office Action dated Oct. 5, 2006 from U.S. Appl. No. 11/005,469.
Office Action dated Oct. 6, 2006 from U.S. Appl. No. 11/005,445.
Office Action dated Oct. 6, 2008 from U.S. Appl. No. 11/005,444.
Office Action dated Oct. 7, 2008 from U.S. Appl. No. 10/602,691.
Office Action dated Oct. 7, 2008 from U.S. Appl. No. 11/005,445.
Office Action dated Oct. 9, 2007 from U.S. Appl. No. 11/005,444.
Office Action dated Oct. 9, 2007 from U.S. Appl. No. 11/005,466.
Office Action dated Oct. 9, 2007 from U.S. Appl. No. 11/005,472.
Office Action dated Sep. 10, 2004 from U.S. Appl. No. 10/602,976.
Office Action dated Sep. 20, 2007 from U.S. Appl. No. 10/602,142.
Office Action dated Sep. 26, 2006 from U.S. Appl. No. 11/005,468.
Office Action dated Sep. 5, 2008 from U.S. Appl. No. 11/005,443.
Oivanen, M., et aZ, "Additional evidence for the exceptional mechanism of the acid-catalyzed hydrolysis of 4-oxopyrimidine nucleosides: Hydrolysis of 1-(I-alkoxyalkyl)uracils, seconucleosides, 3'-C-alkyl nucleosides and nucleoside 3',5'-cyclic monophosphates," J. Chem. Soc. Perkin Trans. 2, 1994:309-314 (1994).
Olsen et al. (Oral Session V, Hepatitis C Virus, Flaviviridae; 16th International Conference on Antiviral Research (Apr. 27, 2003, Savannah, Ga.) p. A76).
Ong, S.P., et al, "Synthesis of 3'-C-methyladenosine and 3'-C-methyluridine diphosphates and their interaction with the ribonucleoside diphosphate reductase from Corynebacterium nephridii," Biochemistry, 31(45):11210-11215 (1992).
Oral Session V, Hepatitis C Virus, Flaviviridae; 16UJ International Conference on Antiviral Research (Apr. 27, 2003, Savannah, Ga.) p. A75-77.
Pagliaro, L., et al., "[Hepatology: Old, recent and (maybe) future stories. A narrative review]. Epatologia: Ieri, Oggi E (Forse) Domani," Recenti Progressi in Medicina, (2006) vol. 97, No. 12, pp. 741-750.
Pan-Zhou, X-R, et al., "Differential effects of antiretroviral nucleoside analogs on mitochondrial function in HepG2 cells," Antimicrob. Agents Chemother., 44:496-503 (2000).
Piantadosi, C., et al., "Synthesis and evaluation of novel ether lipid nucleoside conjugates for anti-HIV-1 activity," 1. Med. Chem. 34:1408-1414 (1991).
Pierra, C., et al., "Comparative Studies of Selected Potential Prodrugs of B-L-dC, A Potent and Selective Anti-HBV Agent," Antiviral Res., 50:A79 (2001), Abstract No. 138.
Pierra, C., et al., "NM 283, and efficient prodrug of the potent anti-HCV agent 2'-C-methylcytidine," Nucleosides, Nucleotides and Nucleic Acids (2005), 24(5-7), 767-770.
Pierra, C., et al., "Synthesis and Pharmacokinetics of Valopicitabine (NM283), and Efficient Prodrug of the Potent Anti-HCV Agent 2'-C-Methylcytidine," Journal of Medicinal Chemistry (2006), 49(22), 6614-6620.
Reist, et al., "Potential anticancer agents. LXXVII. Synthesis of nucleosides of purine-6-thiol(6-mercaptopurine) containing "fraudulent" sugars." Journal of Organic Chemistry (1962), 27 3279-83.
Richman, D.D., et al., "The toxicity of azidothyrnidine (AZT) in the treatment of patients with AIDS and AIDS-Related Complex," N Engl. 1. Med., 317(4):192-197 (1987).
Robins, et al., "Purine Nucleosides. XXIX. The Synthesis of 2'-Deoxy-L-adenosine and 2'-Deoxy-L-guanosine and Their [alpha] Anomers," Journal of Organic Chemistry, 35(3), 636-639 (Mar. 1970).
Rong, et al., "The Synthesis and Conformation of 2'-and 3'-Hypermodified Tricyclic Nucleosides and Their Use in the Synthesis of Novel 2'- or 3'-Isomeric 4(7)-Substituted Isoxazolidine-nucleosides," Tetrahedron vol. 50, No. 16, pp. 4921-4936. (1994).
Roque-Afonso, AM, et al., "Performance of TRUGENE hepatitis C virus5' noncoding genotyping kit, a new CLIP sequencing-based assay for hepatitis C virus genotype determination," Journal of Viral Hepatitis. Sep. 2002, vol. 9, Issue 5, pp. 385-389.

(56) References Cited

OTHER PUBLICATIONS

Rosenthal, A., et al., Branched-chain sugar nucleosides. Synthesis of 3'-C-ethyl (and 3'-Cbutyl) uridine Carbohydrate Research, 79:235-242 (1980).

Sakthivel, et al. "Electrophilic fluorination of 5-(cyanomethyl)imidazole-4-carboxylate nucleosides: Facile entry to 3-fluoro-3- deazaguanosine analogues." Synlett (2005), (10), 1586-1590.

Sakthivel, et al., "Direct SNAr amination of fluorinated imidazo[4,5-c]pyridine nucleosides: efficient syntheses of 3-fluoro-3deazaadenosine analogs." Tetrahedron Letters (2005), 46(22), 3883-3887.

Salidino, R., et al., "A new and efficient synthesis of cytidine and adenosine derivatives by dimethyldioxirane oxidation of thiopyrimidine and thiopurine nucleosides," J. chem. Soc., Perkin Trans. I., 21: 3053-3054 (1994).

Samano, V., et al., "Nucleic acid related compounds. 77. 2',3'-Didehydro-2',3'-dideoxy-2'(and 3')-methylnucleosides via [3,3]-sigmatropic rearrangements of 2'(and 3')-methylene-3 '(and 2')-0-thiocathonyl derivatives and radical reduction of a 2'-chloro-3'-methylene analogue," Can. J. Chem., 71: 186-191 (1993).

Samano, V., et al., "Synthesis and radical-induced ring-opening reactions of 2'-deoxyadenosine-2'-spirocyclopropane and its uridine analogue. Mechanistic probe for ribonucleotide reductases," J. Am.Chem. Soc., 114:4007-4008 (1992).

Sandhu, et al., "Evaluation of microdosing strategies for studies in preclinical drug development: Demonstration of linear pharmacokinetics in dogs of a nucleoside analog over a 50-fold dose range." Drug Metabolism and Disposition (2004), 32(11), 1254-1259.

Sato, et al., "C-Nucleoside synthesis. 10. Synthesis of 2'-methylated pyrimidine C-nucleosides." Tetrahedron Letters (1980), 21(20), 1971-4.

Sato, et al., "C-Nucleoside synthesis. 19. Stereocontrolled general synthesis of pyrimidine C-nucleosides having branched-chain sugar moieties." Bulletin of the Chemical Society of Japan (1983), 56(9), 2680-99.

Savochkina, et al., "Substrate properties of c—methylnucleoside triphosphates in RNA syntheses catalyzed by $e.\ coli$ RNA—polymeruse" Molecular Biology, 1989, v. 23, No. 6.

Scheibler, C., "Ueber das Saccharin and die Saccharinsaure," Chemische Berichte, 13:2212-2217 (1880). In German.

Schiff, E.R., "Emerging strategies for pegylated interferon combination therapy," Nature Clinical Practice Gastoenterology and Hepatology, (2007) vol. 4, No. Suppl. 1, pp. S17-S21.

Schmit C., et al., "Synthesis of 2'-Deoxy-2'—Alpha-Monofluoromethyl and Trifluoromethylnucleosides," Synlett, Thieme Verlag, Stuttgart, DE, No. 4, 1994, pp. 241-242.

Schmit, C., et al, "The effects of 2'- and 3'-alkyl substituents on oligonucleotide hybridization and stability," Biorganic & Medicinal Chemistry Letters, 4(16): 1969-1974 (1994).

Serafinowski, P.J., et al., "New method for the preparation of some 2'- and 3'-trifluoromethyl-2',3'-dideoxyuridine derivatives," Tetrahedron (Elsevier Science Publishers), 56(2):333-339 (1999).

Shalaby, et al., "Conformations and Structure Studies of Sugar Lactones in the Solid State. Part 11. The Molecular Structure of a-D-Glucosaccharino-Y-Lactone: 2-C-Mehtyl-D-Ribo-Pentono-1,4-lactone." Carbohydrate Research (1994), 264(2), 191-8.

Sharma, P.K., et al., "Synthesis of 3'-trifluoromethyl nucleosides as potential antiviral agents," Nucleosides, Nucleotides and Nucleic Acids, 19(4):757-774 (2000).

Shi, et al., Synthesis and in vitro Anti-HCV Activity of β-D- and 1-2'-Deoxy-2'-Fluororibonucleosides, Nucleosides, Nucleotides & Nucleic Acids 2005, vol. 23, Nos. 5-7, pp. 875-879.

Shim, Jae H., "Recent patents on nucleoside and nucleotide inhibitors for HCV," Recent Patents on Anti-Infective Drug Discovery (2006), 1(3), 323-331.

Sinko, et al., Carrier-Mediated Intestinal Absorption of Valacyclovir, the L-Valyl Ester Prodrug of Acyclovir. Biopharmaceutics & Drug Disposition 1998, vol. 19, pp. 209-217.

Sinkula et al., "Rationale for design of biologically reversible drug derivatives: prodrugs," *J. Pharm. Sci.*, 1975,64: 181-210.

Smith et al., "Synthesis of new 2'-β-C-methyl related triciribine analogues as anti-HCV agents." Valeant Pharmaceuticals International, Costa Mesa, CA, USA. Bioorganic & Medicinal Chemistry Letters (2004), 14(13), 3517-3520.

Sommadossi J-P, et ai., "Comparison of cytotoxicity of the (−)- and (+)-enantiomer of 2',3'-dideoxy-3'-thiacytidine in normal human bone marrow progenitor cells" Biochemical Pharmacology, 44:1921-1925 (1992).

Sommadossi J-P, et al., "Toxicity of 3'-azido-3'-deoxythymidine and 9-(1,3-dihydroxy-2-propoxymethyl)guanine for normal human hematopoietic progenitor cells in vitro" Antimicrobial Agents and Chemotherapy, 31:452-454 (1987).

Song et al., Amino Acid Ester Prodrugs of the Anticancer Agent Gemcitabine: Synthesis, Bioconversion, Metabolic Bioevasion, and hPEPT1-Medicated Transport, Moleculare Pharmaceutics (2005), 2(2), 157-167.

Sorbera, L.A., et al., "Valopicitabine: anti-hepatitis C virus drug RNA—directed RNA polymerase (NS5B) inhibitor," Drugs of the Future (2006), 31 (4), 320-324.

Sowden, J., "The Saccharinic Acids," Adv. Carbohydrate Chem., 12:43-46 (1957).

Spardari, et al., "L-Thmidine is Phosphorylated by Herpes Simplex Virus Type 1 Thymidine Kinase and Inhibits Viral Growth," Journal of Medicinal Chemistry, 35(22), 4214-4220 (1992).

Standring, D.N., et al., "Antiviral Beta-L-Nucleosides Specific for Hepatitis B Virus Infection," Antiviral Chem. & Chemother., 12 (Suppl. 1): 119-129 (2001).

Starrett, J.E.Jr., et al., "Synthesis, oral bioavailability determination, and in vitro evaluation of prodrugs of the antiviral agents 9-(2-(phosphonomethoxy)ethyl]adenine (PMEA)," 1. Med. Chern. 37:1857-1864 (1994).

Stuyver, et al., "Ribonucleoside Analogue That Block Replication of Bovine Viral Diarrhea and Hepatits C Viruses in Culture." Antimicrobial Agents and Chemotherapy, vol. 47, No. 1, Jan. 2003, p. 244-254.

Sundberg et al., Advanced Organic Chemistry, Part b, 1990, pp. 232 and 236.

Takenuki, et al., "Nucleosides and nucleotides. XLIII. On the stereoselectivity of alkyl addition reaction of pyrimidine 2'-ketonucleosides." Chemical & Pharmaceutical Bulletin (1990), 38(11), 2947-52.

Tang, X.-Q., et al., "2'-C-Branched Ribonucleosides: Synthesis of the Phophoramidite Derivatives of 2'-C-B-Methylcytidine and Their Incorporation into Oligonucleotides," J. Org. Chem., 64(3): 747-754 (1999).

The Merck Index, 12th edition, 1996, p. 275.

Tritsch, D., et al., "3'-I3-ethynyl and 2'-deoxy-3'-I3-ethynyl adenosines: First 3'-I3-branched adenosines substrates of adenosine deaminase," Bioorganic & Medicinal Chemistry Letters, 10:139-141 (2000).

Tronchet, et al. "72. Synthese et desamination enzymatique des C-hydroxymethyl-3'-et C-methyl-3'—beta-D-xylofurannosyl-9-adenin es," Helv. Chim. Acta, vol. 62, 1979, pp. 689-695.

Tunitskaya, V.L., et al., "Substrate properties of C'-methyl UTP derivatives in 1'7 RNA polymerase reactions. Evidence for N-type NTP conformation," FEBS Letters, 400:263-266 (1997).

Tyrsted, G., et al "Inhibition of the synthesis of 5-phosphoribosyl-1-pyrophosphate by 3'-deoxyadenosine and structurally related nucleoside analogs," Biochem. Biophys. Acta., 155(2): 619-622 (Feb. 26, 1968).

United States Patent and Trademark Office, "U.S. Appl. No. 11/527,124 Office Action dated May 26, 2011."

United States Patent and Trademark Office, "U.S. Appl. No. 11/527,124 Office Action dated Feb. 14, 2012."

United States Patent and Trademark Office, "U.S. Appl. No. 11/527,124 Notice of Allowance dated Aug. 14, 2012."

United States Patent and Trademark Office, "U.S. Appl. No. 11/644,304 Office Action dated Sep. 24, 2009."

United States Patent and Trademark Office, "U.S. Appl. No. 11/644,304 Notice of Allowance dated Apr. 12, 2010."

United States Patent and Trademark Office, "U.S. Appl. No. 12/504,601 Office Action dated Aug. 29, 2011."

United States Patent and Trademark Office, "U.S. Appl. No. 12/504,601 Notice of Allowance dated Jun. 21, 2012."

(56) References Cited

OTHER PUBLICATIONS

Usui, H., et at., "Synthesis of 2'-dcoxy-8,2'-ethanoadenosine and 3'-deoxy-8,3'-ethanoadenosine (Nucleosides and Nucleotides. LXIV)," Chem. Pharm. Bull., 34(1):15-23 (1986).

Vassilev, V.B., et al., "Bovine diarrhea virus induced apoptosis correlates with increased intracellular viral RNA accumulation," Virus Res., 69(2), 95-107 (2000).

Velazquez, et al., "Synthesis of [1-[3',5'-bis-O-(tert-butyldimethylsily)-beta-D-arabin-and beta-D-ribofumnsoyl] cytosine]-2'—spiro-5"-(4"-amino-1",2"-oxathiole-2",2"-dioxide). Analogues of the highly specific anti-HIV-1 agent TSAO-T," Tetrahedron, vol. 50, 1994, pp. 11013-11022.

Verri, A., et al., "Lack of enantiospecificity of human 2'-deoxycytidine kinase relevance for the activetion of B-L-deoxyctidine analogs as antineolastic and antiviral agents," Molecular Pharmacology, 51(1): 132-138 (Jan. 1997).

Verrii, a., et al., "Relaxed Enantioselectivity of Human Mitochondrial Thymidine Knase and Chemotherapeutic Uses of L-Nucleoside Analogues," Biochem. J., 328(1): 317-320 (Nov. 15, 1997).

Von Buren, et al., "Branched oligodeoxynucleotides: automated synthesis and triple helical hybridization studies." Tetrahedron (1995), 51(31), 8491-506.

Von Janta-Lipinski, M., et al., "Newly Synthesized L-Enantiomers of 3'-Fluoro-Modified B-2'-Deoxyribonucleoside 5'-Triphosphates Inhibit Hepatitis B DNA Polymerase but not the Five Cellular DNA Polymerases a, B, y, d and E Nor HIV-1 Reverse Transcriptase," J. Medicinal Chemistry, 41(12): 2040-2046 (May 21, 1998).

Wagner, D., et al., "Preparation and Synthetic Utility of Some Organotin Derivatives of Nucleosides," J. Org. Chem., 39(1):24-30 (1974).

Walczak, K., et at., "Synthesis of 1-(3-alkyl-2,3-dideoxy-D-pentofuranosyl)uracils with potential anti-HIV activity," Acta Chemica Scand., 45:930-934 (1991).

Walton et al., "Branched-chain sugar nucleosides. A new type of biologically active nucleoside," J. Am. Chem. Soc., 88(19): 4524-25 (1966).

Walton, E., et at., "Branched-chain sugar nucleosides. V. Synthesis and antiviral properties of several branched-chain sugar nucleotides," J. Med. Chem., 12:306-309 (1969).

Weinberg, R.S., et al., "Effect of antiviral drugs and hematopoietic growth factors on in vitro erythropoiesis," Mt. Sinai J. Med. 1998;65(1):5-13.

Whistler, R. L., and BeMiller, J.N., "[118] 'a'-D-Glucosaccharino-1,4-Lactone," Methods in Carbohydrate Chemistry, 2:484-485 (1963).

Wohnsland, A., et al., "Viral determinants of resistance to treatment in patients with hepatitis C," Clinical Microbiology reviews, (2007) vol. 20, No. 1, pp. 23-38.

Wolf, et al., "New 2'—C-Branched-Chain Sugar Nucleoside Analogs With Potential Antiviral or Antitumor Activity," Synthesis, Georg Thieme Verlag. Stuttgart, DE, No. 8, Aug. 1992 (Aug. 1992), pp. 773-778.

Wolfe, M.S., et al., "A concise synthesis of 2'-C-methylribonucleosides," Tetrahedron Letters, 36(42):7611-7614 (1995).

Wu, et al., Targeting NS5B RNA-dependent RNA polymerase for anti-HCV chemotherapy. Current Drug Targets—Infectious Disorders 2003, vol. 3, p. 207-219.

Wu, J.-c., et al., A new stereospecific synthesis of [3.1.0] bicyclic cyclopropano analog of 2',3'-dideoxyuridine, Tetrahedron, 46(7):2587-2592 (1990).

Yarchoan, R., et al. "Long-term toxicity I activity profile of 2',3'-dideoxyinosine in AIDS or AIDS-related complex," The Lancet, 336(8714):526-529 (1990).

Yoshida Y, et al., "Reversal of azidothymidine-induced bone marrow suppression by 2',3'-dideoxythymidine as studied by hemopoietic clonal culture," AIDS Res. Hum. Retroviruses, 6(7):929-932 (1990).

Zedeck et al., "Inhibition of the steroid induced synthesis of $\Delta$5-3-ketosteroid isomerase in Pseudomonas testosterone by a new purine deoxyribonucleoside analog: 6-chloro-8aza-9-cyclopentylpurinc," Mol. Phys., 3(4):386-95 (1967).

Zemlicka, J., et al. "Aminoacyl Derivatives of Nucleosides, Nucleotides, and polynucleotides. VIII. The Preparation of 2'(3)—O-L-Phenylalanyluridine, -cytidenie,—Adensonine, -inosine,—guanosine and 2'-Deoxy-3' O-L-Phenylalanyladenosine," Collection Czecoslov, Chem. Commun.1969, vol. 43, No. 13, 3755-3767.

Zemlicka, J., et al., "Substrate Specificity of Ribosomal Peptidyltransferase. Peditidyltranferase. Effect of Modifications in the Heterocyclic, Carbohydrate and Amino Acid Moiety of 2'(3)-O-L-Phenyladenosine." Biochemistry. Dec. 2, 1975, vol. 14, No. 24, 5239-5249.

Zhou, et al., Pharmacokinetics and pharmacodynamics of valopicitabine. Journal of Hepatology 2005, vol. 42 (Suppl. 2), p. 229.

Zinchenko, et al., "2', 3' & 5'—uridine methyl derivatives in microbiological transelicozilation." Doklady Akad Nauk v.297(3), pp. 731-734 (1987).

Zinchenko, et al., "Substrate specificity of uridine and purine nucleoside phosporlases in whole cells of *E. Coli*" Bioplymers & a cell, 1988, v. 4, No. 6.

Zinchenko, et al., "Substrate Specificity of Uridine and Purine Nucleoside Phosphorylases of the Whole Cells of *Escherichia Coli*." Nucleic Acids Research, Symposium Series No. 18., 1987, pp. 137-140.

Zon, G., "Cyclophosphamide Analogues," Chapter 4 in Progress in Medicinal Chemistry, vol. 19, G.P. Ellis and G.B. West, Eds., pp. 205-246 (1982).

Kawana et al., The Synthesis of C-Methyl Branched-Chain Deoxy Sugar Nucleosides by the Deoxygenative Methylation of O-Tosylated Adenosines with Grignard Reagents (1988) Bull. Chem. Soc. Jpn. 61:2437-2442.

King et al., Inhibition of the replication of a hepatitis C virus-like RNA template by interferon and 3'-deoxycytidine (2002) Antiviral Chemistry & Chemotherapy 13:363-370.

Siein et al., Phosphorylation of Nucleoside Analog Antiretrovirals: A Review for Clinicians (2001) Pharmacotherapy 21:11-34.

Tong et al., Nucleosides of thioguanine and other 2-amino-6-substituted purines from 2-acetamido-5-chloropurine (1967) J Org Chem. 32:859-62.

\* cited by examiner

| Virus | Amino Acid Sequence of RNA Polymerase (NS5B) Domain B | |
|---|---|---|
| HCV-1b | CRASGVLTTSCGN | SEQ ID NO: 70 |
| HCV-2A | CRASGVLTTSCGN | SEQ ID NO: 71 |
| BVDV | QRGSGQPDTSAGN | SEQ ID NO: 73 |
| CSFV | QRGSGQPDTSAGN | SEQ ID NO: 72 |
| HGV | CRSSGVLTTSASN | SEQ ID NO: 74 |
| GBV-B | CRSSGVYTTSSSN | SEQ ID NO: 75 |
| Kunjin | QRGSGQVVTYALN | SEQ ID NO: 76 |
| Dengue | QRGSGQVGTYGLN | SEQ ID NO: 77 |

2'-BRANCHED NUCLEOSIDES AND FLAVIVIRIDAE MUTATION

CROSS-REFERENCE

This application is a continuation of U.S. application Ser. No. 14/183,438, filed Feb. 18, 2014, which is a continuation of U.S. application Ser. No. 12/914,914, filed Oct. 28, 2010, which is a continuation of U.S. application Ser. No. 10/715,729, filed on Nov. 17, 2003, now issued as U.S. Pat. No. 7,824,851, which claims priority to U.S. Application No. 60/426,675, filed on Nov. 15, 2002, the disclosures of which are hereby incorporated by reference in their entireties.

FIELD OF THE INVENTION

This invention is a method for the treatment of Flaviviridae infection in a host, such as a human, in need of such therapy, that includes the administration of a 2'-branched nucleoside, or a pharmaceutically acceptable salt, ester, or prodrug thereof, in combination and/or alternation with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, and/or one or more drugs that are associated with such a mutation. The invention also includes a method for the treatment of Flaviviridae infection in a host, such as a human, in need of such therapy, that includes the administration of a 2'-branched nucleoside, or a pharmaceutically acceptable salt, ester, or prodrug thereof, in combination and/or alternation with interferon. The invention also includes a method to detect a mutant strain of Flaviviridae and a method for its treatment, and kits and materials for such detection.

BACKGROUND OF THE INVENTION

The Flaviviridae family of viruses comprises at least three distinct genera: pestiviruses, which cause disease in cattle and pigs; flaviviruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the dengue hemorrhagic fever viruses (DHF), yellow fever virus, West Nile virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med.*, 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H.-J., *Advances in Virus Research*, 1996, 47, 53-118; Moennig V., et al, *Adv. Vir. Res.* 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are approximately 6 HCV genotypes and more than 50 subtypes. HCV is a major cause of hepatitis globally. Most HCV infections become persistent and about 75% of cases develop chronic liver disease. Chronic HCV infection can lead to development of cirrhosis, hepatocellular carcinoma and liver failure. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal two-thirds of the ORF and are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al. (1988) Nature 333:22; Bazan and Fletterick (1989) Virology 171: 637-639; Gorbalenya et al. (1989) Nucleic Acid Res. 17.3889-3897). Similarly, the NS5B proteins of pestiviruses and hepaciviruses have the motifs characteristic of RNA-directed RNA polymerases (Koonin, E. V. and Dolja, V. V. (1993) Crit. Rev. Biochem. Molec. Biol. 28:375-430).

Furthermore, the actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett (1991) Virology 184:341-350; Bartenschlager et al. (1993) J. Virol. 67:3835-3844; Eckart et al. (1993) Biochem. Biophys. Res. Comm. 192:399-406; Grakoui et al. (1993) J. Virol. 67:2832-2843; Grakoui et al. (1993) Proc. Natl. Acad. Sci. USA 90:10583-10587; Hijikata et al. (1993) J. Virol. 67:4665-4675; Tome et al. (1993) J. Virol. 67:4017-4026). The NS4A protein, in both cases, acts as a cofactor with the NS3 serine protease (Bartenschlager et al. (1994) J. Virol. 68:5045-5055; Failla et al. (1994) J. Virol. 68: 3753-3760; Lin et al. (1994) 68:8147-8157; Xu et al. (1997) J. Virol. 71:5312-5322). The NS3 protein of both viruses also functions as a helicase (Kim et al. (1995) Biochem. Biophys. Res. Comm. 215: 160-166;

Jin and Peterson (1995) Arch. Biochem. Biophys., 323:47-53; Warrener and Collett (1995) J. Virol. 69:1720-1726). Finally, the NS5B proteins of pestiviruses and hepaciviruses have the predicted RNA-directed RNA polymerases activity (Behrens et al. (1996) EMBO J. 15:12-22; Lchmann et al. (1997) J. Virol. 71:8416-8428; Yuan et al. (1997) Biochem. Biophys. Res. Comm. 232:231-235; Hagedorn, PCT WO 97/12033; Zhong et al. (1998) J. Virol. 72.9365-9369).

Examples of antiviral agents that have been identified as active against the Flaviviridae family of viruses include:

(1) Interferon

Interferons (IFNs) are compounds that have been commercially available for the treatment of chronic hepatitis for nearly a decade. IFNs are glycoproteins produced by immune cells in response to viral infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Gary L. Davis. *Gastroenterology* 118:S104-S114, 2000).

A number of patents disclose HCV treatments using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,908,621 to Glue et al. discloses the use of polyethylene glycol modified interferon for the treatment of HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849, 696.

(2) Ribavirin (Battaglia, A. M. et al., *Ann. Pharmacother,* 2000, 34, 487-494); Berenguer, M. et al. *Antivir. Ther.,* 1998, 3 (Suppl. 3), 125-136).

Ribavirin (1-β-D-ribofuranosyl-1-1,2,4-triazole-3-carboxamide) is a synthetic, non-interferon-inducing, broad spectrum antiviral nucleoside analog. It is sold under the trade names Virazole™ (The Merck Index, 11th edition, Editor: Budavari, S., Merck & Co., Inc., Rahway, N.J., pi304, 1989); Rebetol™ (Schering Plough) and Co-Pegasus (Roche). U.S. Pat. No. 3,798,209 and RE29,835 (ICN Pharmaceuticals) disclose and claim ribavirin. Ribavirin is structurally similar to guanosine, and has in vitro activity against several DNA and RNA viruses including Flaviviridae (Gary L. Davis. *Gastroenterology* 118:S104-S114, 2000). U.S. Pat. No. 4,211,771 (to ICN Pharmaceuticals) discloses the use of ribavirin as an antiviral agent. Ribavirin reduces serum amino transferase levels to normal in 40% of patients, but it does not lower serum levels of HCV-RNA (Gary L. Davis. *Gastroenterology* 118:S104-S114, 2000). Thus, ribavirin alone is not effective in reducing viral RNA levels. Additionally, ribavirin has significant toxicity and is known to induce anemia.

Combination of Interferon and Ribavirin

Schering-Plough sells ribavirin as Rebetol® capsules (200 mg) for administration to patients with HCV. The U.S. FDA has approved Rebetol capsules to treat chronic HCV infection in combination with Schering's alpha interferon-2b products Intron® A and PEG-INTRON™ (pegylated interferon alfa-2b). Rebetol capsules are not approved for monotherapy (i.e., administration independent of Intron® A or PEG-INTRON™ (pegylated interferon alfa-2b)), although Intron A and PEG-INTRON™ (pegylated interferon alfa-2b) are approved for monotherapy (i.e., administration without ribavirin). Hoffman La Roche is selling ribavirin under the name Co-Pegasus in Europe and the United States, also for use in combination with interferon for the treatment of HCV. Other alpha interferon products include Roferon-A (Hoffmann-La Roche), Infergen® (Intermune, formerly Amgen's product), and Wellferon® (Wellcome Foundation) are currently FDA-approved for HCV monotherapy. Interferon products currently in development for HCV include: Roferon-A (interferon alfa-2a) by Roche, PEGASYS® (pegylated interferon alfa-2a) by Roche, INFERGEN® (interferon alfacon-1) by InterMune, OMNIFERON™ (natural interferon) by Viragen, ALBUFERON® (interferon alpha) by Human Genome Sciences, REBIF® (interferon beta-1a) by Ares-Serono, Omega Interferon by BioMedicine, Oral Interferon Alpha by Amarillo Biosciences, and Interferon gamma-1b by InterMune.

The combination of IFN and ribavirin for the treatment of HCV infection has been reported to be effective in the treatment IFN naïve patients (Battaglia, A.M. et al., *Ann. Pharmacother.* 34:487-494, 2000). Combination treatment is effective both before hepatitis develops and when histological disease is present (Berenguer, M. et al. *Antivir. Ther.* 3 (Suppl. 3):125-136, 1998). Currently, the most effective therapy for HCV is combination therapy of pegylated interferon with ribavirin (2002 NIH Consensus Development Conference on the Management of Hepatitis C). However, the side effects of combination therapy can be significant and include hemolysis, flu-like symptoms, anemia, and fatigue (Gary L. Davis. *Gastroenterology* 118:S104-S114, 2000).

(3) Substrate-based NS3 protease inhibitors (for example, Attwood et al., *Antiviral peptide derivatives*, PCT WO 98/22496, 1998; Attwood et al., *Antiviral Chemistry and Chemotherapy* 1999, 10, 259-273; Attwood et al., *Preparation and use of amino acid derivatives as anti-viral agents*, German Patent Pub. DE 19914474; Tung et al. *Inhibitors of serine proteases, particularly hepatitis C virus NS3 protease*, PCT WO 98/17679), including alphaketoamides and hydrazinoureas, and inhibitors that terminate in an electrophile such as a boronic acid or phosphonate (Llinas-Brunet et al., *Hepatitis C inhibitor peptide analogues*, PCT WO 99/07734).

(4) Non-substrate-based inhibitors, for example, 2,4,6-trihydroxy-3-nitro-benzamide derivatives (Sudo K. et al., *Biochemical and Biophysical Research Communications,* 1997, 238, 643-647; Sudo K. et al. *Antiviral Chemistry and Chemotherapy,* 1998, 9, 186), including RD3-4082 and RD3-4078, the former substituted on the amide with a 14 carbon chain and the latter processing a para-phenoxyphenyl group;

(5) Thiazolidine derivatives which show relevant inhibition in a reverse-phase HPLC assay with an NS3/4A fusion protein and NS5A/5B substrate (for example Sudo K. et al., *Antiviral Research,* 1996, 32, 9-18), especially compound RD-1-6250, possessing a fused cinnamoyl moiety substituted with a long alkyl chain, RD4 6205 and RD4 6193;

(6) Thiazolidines and benzanilides (for example Kakiuchi N. et al. *J. EBS Letters* 421, 217-220; and Takeshita N. et al. *Analytical Biochemistry,* 1997, 247, 242-246);

(7) A phenanthrenequinone possessing activity against protease in a SDS-PAGE and autoradiography assay isolated from the fermentation culture broth of *Streptomyces* sp., for example, Sch 68631 (Chu M. et al., *Tetrahedron Letters,* 1996, 37, 7229-7232), and Sch 351633, isolated from the fungus *Penicillium griscofuluum,* which demonstrates activity in a scintillation proximity assay (Chu M. et al., *Bioorganic and Medicinal Chemistry Letters* 9, 1949-1952);

(8) Selective NS3 inhibitors, for example, those based on the macromolecule elgin c, isolated from leech (Qasim M. A. et al., *Biochemistry,* 1997, 36, 1598-1607);

(9) Helicase inhibitors (for example Diana G. D. et al., *Compounds, compositions and methods for treatment of hepatitis C,* U.S. Pat. No. 5,633,358; Diana G. D. et al., *Piperidine derivatives, pharmaceutical compositions thereof and their use in the treatment of hepatitis C,* PCT WO 97/36554);

(10) Polymerase inhibitors for example nucleotide analogues, gliotoxin (Ferrari R. et al. *Journal of Virology,* 1999, 73, 1649-1654), and the natural product cerulenin (Lohmann V. et al., *Virology,* 1998, 249, 108-118);

(11) Antisense phosphorothioate oligodeoxynucleotides (S-ODN) complementary to sequence stretches in the 5' non-coding region (NCR) of the virus (Alt M. et al., *Hepatology,* 1995, 22, 707-717), or nucleotides 326-348 comprising the 3' end of the NCR and nucleotides 371-388 located in the core coding region of the HCV RNA (Alt M. et al., *Archives of Virology,* 1997, 142, 589-599; Galderisi U. et al., *Journal of Cellular Physiology,* 1999, 181, 251-257).

(12) Inhibitors of IRES-dependent translation (Ikeda N et al., *Agent for the prevention and treatment of hepatitis C,* Japanese Patent Pub. JP-08268890; Kai Y. et al. *Prevention and treatment of viral diseases,* Japanese Patent Pub. JP-10101591).

(13) Nuclease-resistant ribozymes (for example Maccjak, D. J. et al., *Hepatology* 1999, 30, abstract 995).

(14) Nucleoside analogs have also been developed for the treatment of Flaviviridae infections.

Idenix Pharmaceuticals, Ltd. discloses branched nucleosides, and their use in the treatment of HCV and flaviviruses and pestiviruses in US Patent Publication No. 2003/0050229 A1 and US Patent Publication No. 2003/0060400 A1, which correspond to International Publication Nos. WO 01/90121 and WO 01/92282. A method for the treatment of hepatitis C infection (and flaviviruses and pestiviruses) in humans and other host animals is disclosed in the Idenix publications that includes administering an effective amount of a biologically active 1', 2', 3' or 4'-branched (β-D or β-L nucleosides or a pharmaceutically acceptable salt or prodrug thereof, administered either alone or in combination, optionally in a pharmaceutically acceptable carrier.

Other patent applications disclosing the use of certain nucleoside analogs to treat hepatitis C virus include: International Patent Publication Nos. WO 01/32153 (PCT/CA00/01316; filed Nov. 3, 2000) and WO 01/60315 (PCT/CA01/00197; filed Feb. 19, 2001) filed by Bio Chem Pharma, Inc. (now Shire Biochem, Inc.); US Patent Publication No. 2002/0147160 and the corresponding International Patent Publication Nos. WO 02/057425 (PCT/US02/01531; filed Jan. 18, 2002) and WO 02/057287 (PCT/US02/03086; filed Jan. 18, 2002) filed by Merck & Co., Inc.; US Patent Publication Nos. 2003/083307 A1 and US 2003/008841 A1, and the corresponding International Patent Publication Nos. WO 02/18404 (PCT/EPO1/09633; published Aug. 21, 2001); WO 02/100415 and WO 02/094289, filed by Hoffman-LaRoche; US Patent Publication No. 2003/028013 A1 and the corresponding International Patent Publication Nos. WO 03/062255 and WO 03/061385 filed by Ribapharm; and WO 01/79246 and WO 02/32920 filed by Pharmasset.

(15) Miscellaneous compounds including 1-amino-alkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

(16) Other compounds currently in clinical development for treatment of hepatitis c virus include: Interleukin-10 by Schering-Plough, IP-501 by Intemeuron, Merimebodib VX-497 by Vertex, AMANTADINE (Symmetrel) by Endo Labs Solvay, HEPTAZYME by RPI, IDN-6556 by Idun Pharma., XTL-002 by XTL., HCV/MF59 by Chiron, CIVA-CIR by NABI, LEVOVIRIN by ICN, VIRAMIDINE by ICN, ZADAXIN (thymosin alfa-1) by Sei Clone, CEPLENE (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc. and JTK 003 by AKROS Pharma.

Drug-resistant variants of viruses can emerge after prolonged treatment with an antiviral agent. Drug resistance most typically occurs by mutation of a gene that encodes for an enzyme used in viral replication, and, for example, in the case of HIV, reverse transcriptase, protease, or DNA polymerase. It has been demonstrated that the efficacy of a drug against viral infection can be prolonged, augmented, or restored by administering the compound in combination or alternation with a second, and perhaps third, antiviral compound that is effective in combating the virus. The pharmacokinetics, biodistribution, or other parameter of the drug can be altered by such combination or alternation therapy. In general, combination therapy is typically preferred over alternation therapy because it induces multiple simultaneous pressures on the virus. One cannot predict, however, what mutations will be induced in the viral genome by a given drug, whether the mutation is permanent or transient, or how an infected cell with or without a mutated viral sequence will respond to therapy with other agents in combination or alternation. This is exacerbated by the fact that there is a paucity of data on the kinetics of drug resistance in long-term cell cultures treated with modern antiviral agents.

It is an object of the present invention to optimize the treatment of HCV infection.

It is a further object to provide the optimal administration of 2'-branched nucleosides, and in particular, 2'-branched pyrimidine nucleosides, for the treatment of Flaviviridae infections.

It is another object of the present invention to provide a method and composition that includes 2'-branched nucleosides for the treatment of patients infected with pestiviruses, flaviviruses, or hepaciviruses that exhibit advantageous or improved pharmacokinetic, biodistribution, metabolic, resistance or other parameters over administration of 2'-branched pyrimidine nucleosides alone.

It is yet another object of the present invention to provide a method and composition for the treatment of patients infected with Flaviviridae in which 2'-branched nucleosides, and in particular, 2'-branched pyrimidine nucleosides are administered in combination and/or alternation with one or more compounds that act synergistically or advantageously with 2'-branched pyrimidine nucleosides against the virus.

It is still another object of the present invention to provide a method and composition for the treatment of patients infected with a drug resistant form of pestiviruses, flaviviruses, or hepaciviruses.

It is also an object of the invention to provide a method and kit to identify a mutant strain of Flaviviridae.

SUMMARY OF THE INVENTION

It has been discovered that prolonged use of a 2'-branched nucleoside, for example a 2'-branched nucleoside depicted below, and in particular, a 2'-branched pyrimidine nucleoside, such as the compound β-D-2'-$CH_3$-riboC, or a 2'-branched purine nucleoside, including the compound β-D-2'-$CH_3$-riboAdenosine or β-D-2'-$CH_3$-ribo-6-N-methyl amino adenosine, is associated with a mutation at a nucleotide that encodes for serine in the highly conserved consensus sequence, XRXSGXXXT (SEQ ID NO: 63), of domain B of the RNA polymerase region (FIG. 11) of Flaviviridae, which results in a change in the amino acid residue serine to a different amino acid, for example, threonine. This domain is found in the NS5B region of the HCV genome, as well as in genomes of other flaviviruses. It is highly conserved among all hepaci-, pesti- and flavivirus genomes (FIG. 11, Lai et al. *J Virol.* 1999, 73, 10129-36).

In one embodiment of the invention, the 2'-branched nucleoside is of the general formula:

or its pharmaceutically acceptable prodrug and/or salt, wherein $R^1$, $R^2$, and $R^3$ are independently H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein $R^1$, $R^2$ or $R^3$ is independently H or phosphate when administered in vivo; and $R^4$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, or —N(acyl)$_2$;

and Base is a purine or pyrimidine as further described herein.

In a second embodiment of the invention, the 2'-branched nucleoside is of the general formula:

(II)

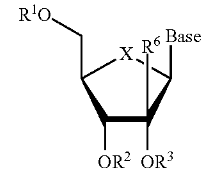

(III)

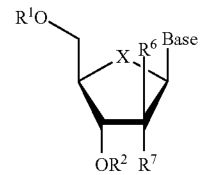

or its pharmaceutically acceptable prodrug and/or salt, wherein

Base is a purine or pyrimidine base as defined herein;

$R^1$, $R^2$ and $R^3$ are independently H, phosphate (including mono-, di- or triphosphate and a stabilized phosphate); straight chained, branched or cyclic alkyl (including lower alkyl); acyl (including lower acyl); CO-alkyl, CO-aryl, CO-alkoxyalkyl, CO-aryloxyalkyl, CO-substituted aryl, sulfonate ester (including alkyl or arylalkyl sulfonyl including methanesulfonyl); benzyl, wherein the phenyl group is optionally substituted with one or more substituents as described in the definition of aryl given herein; alkylsulfonyl, arylsulfonyl, aralkylsulfonyl, lipid (including a phospholipid); amino acid; carbohydrate; peptide; cholesterol; or a pharmaceutically acceptable leaving group that provides a compound wherein $R^1$, $R^2$ or $R^3$ is independently H or phosphate when administered in vivo;

$R^6$ is alkyl (including lower alkyl and halogenated alkyl), $CH_3$, $CF_3$, azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, —N(acyl)$_2$; and $R^7$ is hydrogen, $OR^3$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), fluorine, chlorine, bromine, iodine, $NO_2$, $NH_2$, —NH(lower alkyl), —NH(acyl), —N(lower alkyl)$_2$, —N(acyl)$_2$; and X is O, S, $SO_2$ or $CH_2$.

and Base is a purine or pyrimidine as further described herein.

In a third embodiment the invention, the 2'-branched nucleoside is of the general formula:

(IV)

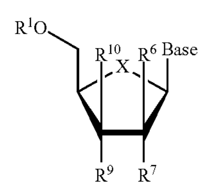

wherein:

Base is a purine or pyrimidine base as defined herein;

$R^6$ is alkyl (including lower alkyl and halogenated alkyl), $CH_3$, $CF_3$, azido, cyano, alkenyl, alkynyl, Br-vinyl, 2-Brethyl, —C(O)O(alkyl), —C(O)O(lower alkyl), —O(acyl), —O(lower acyl), —O(alkyl), —O(lower alkyl), —O(alkenyl), $CF_3$, fluoro, chloro, bromo, iodo, $NO_2$, $NH_2$, —NH(lower alkyl), —NH(acyl), —N(lower alkyl)$_2$, —N(acyl)$_2$;

$R^7$ is $OR^2$, hydroxy, alkyl (including lower alkyl), azido, cyano, alkenyl, alkynyl, Br-vinyl, halo-vinyl, —C(O)O (alkyl), —C(O)O(lower alkyl), —O(acyl), —O(lower acyl), —O(alkyl), —O(lower alkyl), —O(alkenyl), fluorine, chlorine, bromine, iodine, $NO_2$, $NH_2$, —NH(lower alkyl), —NH(acyl), —N(lower alkyl)$_2$, —N(acyl)$_2$;

$R^9$ is hydrogen, $OR^3$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH (acyl), —N(lower alkyl)$_2$, —N(acyl)$_2$;

$R^{10}$ is H, alkyl (including lower alkyl), fluorine, chlorine, bromine or iodine;

$R^1$, $R^2$ and $R^3$ are independently H, phosphate (including mono-, di- or triphosphate and a stabilized phosphate); straight chained, branched or cyclic alkyl (including lower alkyl); acyl (including lower acyl); CO-alkyl, CO-aryl, CO-alkoxyalkyl, CO-aryloxyalkyl, CO-substituted aryl, sulfonate ester (including alkyl or arylalkyl sulfonyl including methanesulfonyl); benzyl, wherein the phenyl group is optionally substituted with one or more substituents as described in the definition of aryl given herein; alkylsulfonyl, arylsulfonyl, aralkylsulfonyl, lipid (including a phospholipid); amino acid; carbohydrate; peptide; cholesterol; or a pharmaceutically acceptable leaving group that provides a compound wherein $R^1$, $R^2$ or $R^3$ is independently H or phosphate when administered in vivo; and X is O, S, $SO_2$ or $CH_2$.

In the case of BVDV infection, 2'-branched nucleosides, and, in particular, 2'-branched pyrimidine nucleosides such as the compound β-D-2'-$CH_3$-riboC induce a mutation from a guanine (G) to cytidine (C) at reside 1214 of the RNA polymerase of BVDV, which results in a change in the amino acid residue serine to threonine at position 405 of the enzyme. This serine residue is located in the conserved consensus sequence (XRXSGXXXT (SEQ ID NO: 63)) of the RNA polymerase domain B (FIGS. 5 and 11), identified by mutational analysis (Lai V. C., Kao C. C., Ferrari E., Park J., Uss A. S., Wright-Minogue J., Hong Z., and J. Y. Lau. "Mutational analysis of bovine viral diarrhea virus RNA-dependent RNA polymerase" *J Virol.* 1999, 73, 10129-36).

In the case of HCV infection, 2'-branched nucleosides, and, in particular, 2'-branched pyrimidine nucleosides such as the compound β-D-2'-$CH_3$-riboC induce a mutation at a nucleotide that encodes for Serine$_{282}$ in the highly conserved consensus sequence, XRXSGXXXT (SEQ ID NO: 63), of domain B of the RNA polymerase region (FIG. 11), which results in a change from serine to a different amino acid, such as threonine.

Furthermore, it has been discovered that 2'-branched nucleosides and interferon act synergistically to inhibit Flaviviridae. In particular 2'-branched pyrimidine nucleosides such as the compound β-D-2'-$CH_3$-riboC or a 2'-branched purine nucleosides such as the compound β-D-2'-$CH_3$-riboA or β-D-2'-$CH_3$-ribo-6-N-methyl amino adenosine, and interferon alpha-2b administered in combination and/or alternation act synergistically to inhibit Flaviviridae. Moreover, it has been discovered that the resistant viral populations, which emerge after 2'-branched nucleoside treatment, for example, β-D-2'-$CH_3$-riboC treatment, show increased sensitivity to subsequent treatment with interferon. Thus, sequential and/or combination therapy of a 2'-branched nucleoside and interferon can substantially reduce Flaviviridae infections.

One aspect of the present invention provides a method to treat a Flaviviridae infection by administering a therapeutically effective amount of a 2'-branched nucleoside, for example, a 2'-branched pyrimidine nucleoside, for example β-D-2'-$CH_3$-riboC, or its pharmaceutically acceptable prodrug and/or salt, to a host, such as a human, in need of such therapy, in combination and/or alternation with one or more drugs that directly or indirectly induce a mutation in a Flaviviridae at a location other than a mutation of a nucleotide that results in a change from serine to a different amino acid in the highly conserved consensus sequence, XRX SGXXXT (SEQ ID NO: 63), of domain B of the RNA polymerase region, and/or one or more drugs that are associated with such a mutation. This highly conserved serine residue corresponds to amino acid position 405 of the RNA polymerase region of the BVDV genome. It also corresponds to amino acid position 282 of the RNA polymerase region of the HCV genome (FIG. 11; Lai et al. *J Virol.*, 1999, 73, 10129-36).

Another aspect of the present invention provides a method to treat and/or to substantially cure a Flaviviridae infection in a host infected with a Flaviviridae that contains a serine to threonine mutation at the conserved serine residue of a Flaviviridae (FIG. 11), for example, amino acid 405 of the RNA polymerase region of BVDV or amino acid 282 of the RNA polymerase of HCV, by administering a therapeutically effective amount of interferon. In a specific embodiment, interferon alpha-2b is administered to treat and/or to substantially cure the infection caused by a mutated Flaviviridae virus.

The invention disclosed herein also minimally includes at least the following embodiments:

(i) A pharmaceutical composition effective for the treatment of a Flaviviridae infection in a host, such as a human, comprising an effective amount of a 2'-branched nucleoside, for example, a 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or its pharmaceutically acceptable prodrug and/or salt, optionally in a pharmaceutically acceptable carrier or diluent, in combination with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, for example, other than nucleotide 1214 (G to C) or 405 Ser to Thr of the RNA polymerase region of BVDV or nucleotide 8443 (G to C) of the HCV genome or 282 Ser to Thr of the RNA polymerase region of HCV (FIG. 11; Lai et al. *J Virol.*, 1999, 73, 10129-36), and/or one or more drugs that are associated with such a mutation.

(ii) A pharmaceutical composition effective for the treatment of a Flaviviridae infection in a host, such as a human, comprising an effective amount of a 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$- riboA or β-D-2'-CH₃-ribo-6-N-methylaminopurine or a prodrug, such as the 3'-valine ester prodrug, or a pharmaceutically acceptable prodrug and/or salt thereof, optionally in a pharmaceutically acceptable carrier or diluent, in combination with interferon. Interferons include: Intron-A (interferon alpha-2b) by Schering, PEG-INTRON™ (pegylated interferon alpha-2b) by Schering, Roferon-A (interferon alfa-2a) by Roche, PEGASYS® (pegylated interferon alfa-2a) by Roche, INFERGEN® (interferon alfacon-1) by InterMune, OMNIFERON™ (natural interferon) by Viragen, ALBUFERON® (interferon alpha) by Human Genome Sciences, REBIF® (interferon beta-1a) by Ares-Serono, Omega Interferon by BioMedicine, Oral Interferon Alpha by Amarillo Biosciences, and Interferon gamma-1b by InterMune.

(iii) A pharmaceutical composition effective for the treatment of a Flaviviridae infection in a host, such as a human, comprising:
an effective amount of a 2', 3' and/or 5'-prodrug of a 2'-branched nucleoside, such as β-D-2'-branched pyrimidine nucleoside, for example β-D-2'-CH₃-riboC or a prodrug, including the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, including the 3'-valine ester prodrug, or a pharmaceutically acceptable salt thereof, or a pharmaceutically acceptable salt thereof, optionally in a pharmaceutically acceptable carrier or diluent;
in combination with one or more drugs that directly or indirectly induce a mutation in a Flaviviridae at a location other than a mutation of a nucleotide that results in a change from serine to a different amino acid in the highly conserved consensus sequence, XRX SGXXXT (SEQ ID NO: 63), of domain B of the RNA polymerase region, and/or one or more drugs that are associated with such a mutation.

(iv) A method for treating a Flaviviridae infection in a host, such as a human, comprising administering an effective amount of a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or its pharmaceutically acceptable prodrug and/or salt to the human, optionally in a pharmaceutically acceptable carrier or diluent, in combination and/or alternation with one or more drugs that directly or indirectly induce a mutation in a Flaviviridae at a location other than a mutation of a nucleotide that results in a change from serine to a different amino acid in the highly conserved consensus sequence, XRX SGXXXT (SEQ ID NO: 63), of domain B of the RNA polymerase region, for example, other than nucleotide 1214 (G to C) or 405 Ser to Thr of the RNA polymerase region of BVDV or nucleotide 8443 (G to C) of the HCV genome or 282 Ser to Thr of the RNA polymerase region of HCV (FIG. 11; Lai et al. *J Virol.*, 1999, 73, 10129-36), and/or one or more drugs that are associated with such a mutation.

(v) A method for treating a Flaviviridae infection in a host, such as a human, comprising administering an effective amount of a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable prodrug and/or salt thereof to the host, optionally in a pharmaceutically acceptable carrier or diluent, in combination and/or alternation with interferon. Interferons include: Intron-A (interferon alpha-2b) by Schering, PEG-INTRON™ (pegylated interferon alpha-2b) by Schering, Roferon-A (interferon alfa-2a) by Roche, PEGASYS® (pegylated interferon alfa-2a) by Roche, INFERGEN® (interferon alfacon-1) by InterMune, OMNIFERON™ (natural interferon) by Viragen, ALBUFERON® (interferon alpha) by Human Genome Sciences, REBIF® (interferon beta-1a) by Ares-Serono, Omega Interferon by BioMedicine, Oral Interferon Alpha by Amarillo Biosciences, and Interferon gamma-1b by InterMune.

(vi) A method for treating a patient infected with a Flaviviridae virus that is resistant to a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable salt thereof, comprising administering an effective amount of interferon, optionally in a pharmaceutically acceptable carrier or diluent, optionally in a manner that substantially eliminates the viral load.

(iv) A method for treating a patient infected with Flaviviridae comprising:
administering an effective amount of a 2', 3' and/or 5'-prodrug of a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable salt thereof, optionally in a pharmaceutically acceptable carrier or diluent;
in combination and/or alternation with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, and/or one or more drugs that are associated with such a mutation.

(v) A method for treating a patient infected with Flaviviridae comprising:
(a) administering to the patient an effective amount of a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable salt thereof; optionally in a pharmaceutically acceptable carrier or diluent;
(b) assaying the blood of the patient to test for seroconversion from wildtype to mutant virus; and
(c) administering an effective amount of interferon; optionally in a pharmaceutically acceptable carrier or diluent.

(vi) A method for assaying a sample suspected of containing a Flaviviridae resistant to a 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof; comprising:

(a) contacting a sample containing a Flaviviridae nucleic acid sequence with a detectable oligonucleotide probe having a sequence complementary a codon that encodes a serine in the highly conserved consensus sequence, XRXSGXXXT (SEQ ID NO: 63), of domain B of the RNA polymerase region of Flaviviridae (FIG. 11);

(b) allowing the probe to hybridize to the sequence; and (c) detecting the hybridization of the probe the sequence.

(vii) A method for assaying a sample suspected of containing a Flaviviridae resistant to a 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof; comprising:

(a) contacting a sample containing a Flaviviridae nucleic acid sequence with a detectable oligonucleotide probe having a sequence complementary to the cytidine at nucleotide 1214 of the RNA polymerase region of BVDV or the cytidine at nucleotide 8443 of HCV;

(b) allowing the probe to hybridize to the sequence; and (c) detecting the hybridization of the probe to cytidine at nucleotide 1214 of the RNA polymerase region of BVDV or at nucleotide 8443 of HCV.

(viii) A method for treating a patient infected with Flaviviridae comprising:

(a) administering an effective amount of a 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof; optionally in a pharmaceutically acceptable carrier or diluent;

(b) obtaining a viral sample from the patient;

(c) determining the replication fitness of the virus;

(d) determining whether the replication fitness of the virus in the sample is less than the replication fitness of the wild-type virus, which indicates resistance to the 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof; and (e) administering an effective amount of interferon to those patients that are resistant to the 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof.

(ix) A method for treating a patient infected with Flaviviridae comprising:

(a) administering an effective amount of a 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof; optionally in a pharmaceutically acceptable carrier or diluent;

(b) obtaining a viral culture sample from the patient;

(c) culturing the sample and comparing the plaque growth between the sample and wild type virus;

(d) determining whether the plaque growth of the sample is smaller than the plaque growth of the wildtype, which indicates resistance to the 2'-branched nucleoside; and (e) administering an effective amount of interferon to those patients that are resistant to the 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof.

(x) A method for diagnosing the presence of a Flaviviridae resistant to a 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof, in a patient comprising:

(a) obtaining a sample suspected of containing a Flaviviridae nucleic acid sequence;

(b) contacting the sample with a detectable oligonucleotide probe having a sequence complementary a codon that encodes a serine in the highly conserved consensus sequence, XRXSGXXXT (SEQ ID NO: 63), of domain B of the RNA polymerase region of Flaviviridae (FIG. 11);

(c) allowing the probe to hybridize to the sequence; and (d) detecting the hybridization of the probe the sequence to determine the presence of a Flaviviridae resistant to the 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof.

(xi) A method for diagnosing of the presence of a Flaviviridae resistant to the 2'-branched nucleoside, such as β-D-2'-branched pyrimidine nucleoside, for example β-D-2'-$CH_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-

2'-CH₃-ribo-6-N-methylaminopurine or a prodrug, such as the 3'-valine ester prodrug, or a pharmaceutically acceptable salt thereof, in a patient comprising:
(a) obtaining a sample suspected of containing a Flaviviridae nucleic acid sequence;
(b) contacting the sample with a detectable oligonucleotide probe having a sequence complementary to the cytidine at nucleotide 1214 of the RNA polymerase region of BVDV or the cytidine at nucleotide 8443 of HCV;
(b) allowing the probe to hybridize to the sequence; and
(c) detecting the hybridization of the probe to cytidine at nucleotide 1214 of the RNA polymerase region of BVDV or at nucleotide 8443 of HCV to determine the presence of a Flaviviridae resistant to the 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable salt thereof.

The disclosed combination and/or alternation regimens are useful in the prevention and treatment of Flaviviridae infections, including BVDV, BDV, CSFV, DHF, yellow fever virus, shock syndrome, Japanese encephalitis virus, and HCV.

In addition, the corresponding amino acid sequences of the Flaviviridae viral markers diagnostic for long term response of Flaviviridae carriers to 2'-branched nucleoside therapy can be determined from the illustrative Flaviviridae nucleotide sequences.

In addition to identifying viral markers for the purposes of identifying Flaviviridae strains that are associated with 2'-branched nucleoside failure, the present invention can be utilized to also identify Flaviviridae strains that respond to 2'-branched nucleoside therapy. In this respect, the absence of viral markers correlated with 2'-branched nucleoside therapy can be used to prescribe a course of treatment that includes 2'-branched nucleoside as a modality for those individuals that carrier Flaviviridae lacking viral markers correlated with 2'-branched nucleoside therapy failure.

In another embodiment, the invention provides an oligonucleotide primer for amplifying an Flaviviridae nucleic acid sequence. In one embodiment, the oligonucleotide is at least 14 nucleotides in length and hybridizes under sequence-specific, stringent hybridization conditions to a nucleotide sequence that contains the marker correlated with therapy failure.

Oligonucleotide sequences used as the hybridizing region of a primer can also be used as the hybridizing region of a probe. Suitability of a primer sequence for use as a probe depends on the hybridization characteristics of the primer. Similarly, an oligonucleotide used as a probe can be used as a primer.

Additionally, the invention provides a method, materials and a kit to detect proteins, peptides or peptide fragments that contain amino acids (as described extensively herein) that are predictive of the long term response of an Flaviviridae carrier to 2'-branched nucleoside therapy, or antibodies to those proteins, peptides or peptide fragments. Host sera or tissue can be tested for either the protein or peptide or the antibody to the protein or peptide, depending on convenience and perhaps concentration of the diagnostic material.

The protein, peptide or peptide fragment can be confirmed by reaction with an antibody, preferably a monoclonal antibody, for example using a Western blot method. Alternatively, the protein or peptide can be isolated and sequenced or otherwise identified by any means known in the art, including by 2D PAGE. In one embodiment, a reactive antibody binds to an Flaviviridae protein or peptide sequence that includes a threonine rather than serine in the highly conserved consensus sequence, XRXSGXXXT (SEQ ID NO: 63), of domain B of the RNA polymerase region, for example at position 405 of the RNA polymerase region of BVDV genome or at position 282 of the RNA polymerase region of the HCV genome.

In another embodiment, the reactive antibody binds specifically to a peptide sequence that includes a threonine rather than serine in the highly conserved consensus sequence, XRXSGXXXT (SEQ ID NO: 63), of domain B of the RNA polymerase region, for example at position 405 of the RNA polymerase region of BVDV genome or at position 282 of the RNA polymerase region of the HCV genome, which represent a specific point mutations in the RNA polymerase region of Flaviviridae that is correlated with therapy failure.

In specific embodiments, an antibody is used that binds to at least one peptide or peptide fragment encoded for by the nucleic acid sequences in sequence ID Nos. 1-31.

In specific embodiments, an antibody is used that binds to at least one peptide or peptide fragment encoded for by the nucleic acid sequences in sequence ID Nos. 32-62.

BRIEF DESCRIPTION OF THE FIGURES

FIG. 1 shows the emergence of β-D-2'-CH₃-riboC-resistant BVDV from untreated BVDV.

FIG. 11 illustrates the alignment of the RNA Polymerase in domain B of various Flaviviridae; bold type with larger font show amino acids that are 100% conserved; underlined serine amino acid residues are ones that may be mutated to threonine after treatment with a 2'-branched nucleoside. [The 100% conserved serine residue is also underlined and represents the amino acid that is mutated to Threonine after treatment with a 2'-branched nucleoside (Ser$_{405}$ of the RNA polymerase region of BVDV; Ser$_{282}$ of the RNA polymerase region of HCV). See Lai et al. *J Virol.* 1999, 73, 10129-36.]

DETAILED DESCRIPTION OF THE INVENTION

It has been discovered that prolonged use of a 2'-branched nucleoside, for example a 2'-branched nucleoside depicted below, and in particular, a 2'-branched pyrimidine nucleoside such as the compound β-D-2'-CH$_3$-riboC, is associated with a mutation at a nucleotide that encodes for serine in the highly conserved consensus sequence, XRXSGXXXT (SEQ ID NO: 63), of domain B of the RNA polymerase region (FIG. 11) of Flaviviridae resulting in a change in the amino acid residue serine to a different amino acid, for example, threonine. This domain is found in the NS5B region of the HCV genome, as well as in genomes of other flaviviruses. It is highly conserved among all hepaci-, pesti- and flavivirus genomes (FIG. 11, Lai et al. *J Virol.* 1999, 73, 10129-36).

Figure 5:
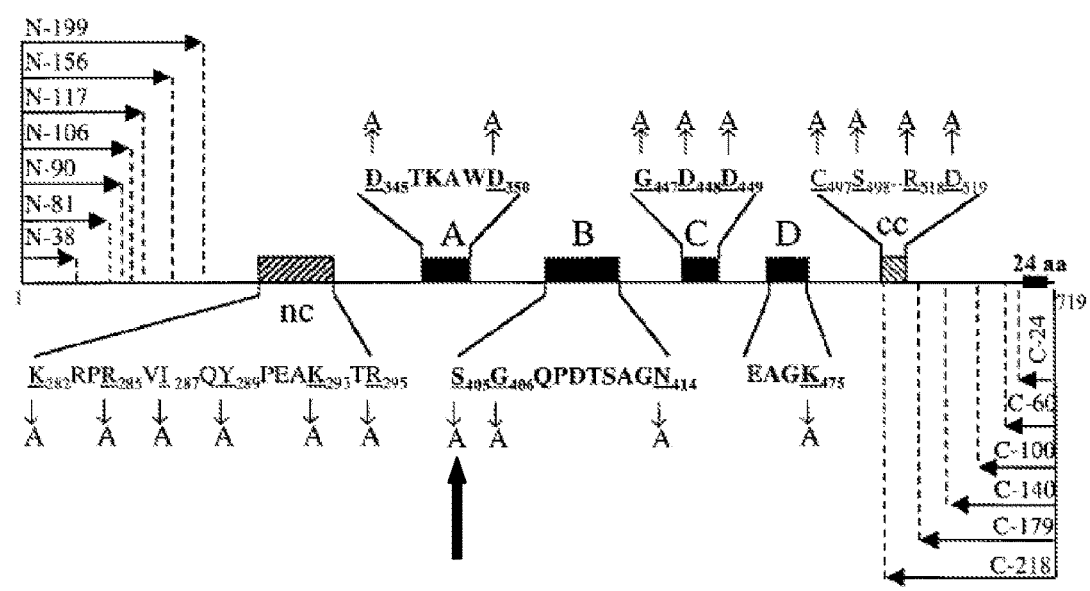
FIG. 5 is a schematic representation of the BVDV NS5B region showing the proposed functional domains, based on the mutational analysis (Vassilev, V. B. and R. O. Donis. (2000) Bovine viral diarrhea virus induced apoptosis correlates with increased intracellular viral RNA accumulation. Virus Res. 69 (2): 95-107). The large arrow indicates the position of the only amino acid change found in the NS5B region of the β-D-2'-CH₃-riboC-resistant BVDV (Ser 405 to Thr 405).

In the case of BVDV infection, 2'-branched nucleosides, and, in particular, 2'-branched pyrimidine nucleosides such as the compound β-D-2'-CH$_3$-riboC induce a mutation from a guanine (G) to cytidine (C) at reside 1214 of the RNA polymerase of BVDV causing a change in the amino acid residue serine to threonine at position 405 of [[of]] the enzyme. This serine residue is located in the conserved consensus sequence (XRXSGXXXT (SEQ ID NO: 63)) of the RNA polymerase domain B (FIGS. 5 and 11), identified by mutational analysis (Lai V. C., Kao C. C., Ferrari E., Park J., Uss A. S., Wright-Minogue J., Hong Z., and J. Y. Lau. "Mutational analysis of bovine viral diarrhea virus RNA-dependent RNA polymerase" *J Virol.* 1999, 73, 10129-36).

In the case of HCV infection, 2'-branched nucleosides, and, in particular, 2'-branched pyrimidine nucleosides such as the compound β-D-2'-CH$_3$-riboC induce a mutation at a nucleotide that encodes for Serine$_{282}$ in the highly conserved consensus sequence, XRXSGXXXT (SEQ ID NO: 63), of domain B of the RNA polymerase region (FIG. 11) resulting in a change from serine to a different amino acid, such as threonine.

Furthermore, it has been discovered that 2'-branched nucleosides and interferon act synergistically to inhibit Flaviviridae. In particular 2'-branched pyrimidine nucleosides such as the compound β-D-2'-CH$_3$-riboC and interferon alpha-2b administered in combination and/or alternation act synergistically to inhibit Flaviviridae. Moreover, it has been discovered that the resistant viral populations, which emerge after 2'-branched nucleoside treatment, for example, β-D-2'-CH$_3$-riboC treatment, show increased sensitivity to subsequent treatment with interferon. Thus, sequential and/or combination therapy of a 2'-branched nucleoside and interferon can substantially reduce Flaviviridae infections.

One aspect of the present invention provides a method to treat a Flaviviridae infection by administering a therapeutically effective amount of a 2'-branched nucleoside, for example, a 2'-branched pyrimidine nucleoside, for example β-D-2'-CH$_3$-riboC, or its pharmaceutically acceptable prodrug and/or salt, to a host, such as a human, in need of such therapy, in combination and/or alternation with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, and/or one or more drugs that are associated with such a mutation. This highly conserved serine residue corresponds to amino acid position 405 of the RNA polymerase region of the BVDV genome. It also corresponds to amino acid position 282 of the RNA polymerase region of the HCV genome (FIG. 11; Lai et al. *J Virol.*, 1999, 73, 10129-36).

Another aspect of the present invention provides a method to treat and/or to substantially cure a Flaviviridae infection in a host infected with a Flaviviridae that contains a serine to threonine mutation at the conserved serine residue of a Flaviviridae (FIG. 11), for example, amino acid 405 of the RNA polymerase region of BVDV or amino acid 282 of the RNA polymerase of HCV, by administering a therapeutically effective amount of interferon. In a specific embodiment, interferon alpha-2b is administered to treat and/or to substantially cure the infection caused by a mutated Flaviviridae virus.

The invention disclosed herein also minimally includes at least the following embodiments:

(i) A pharmaceutical composition effective for the treatment of a Flaviviridae infection in a host, such as a human, comprising an effective amount of a 2'-branched nucleoside, for example, a 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or its pharmaceutically acceptable prodrug and/or salt, optionally in a pharmaceutically acceptable carrier or diluent, in combination with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, for example, other than nucleotide 1214 (G to C) or 405 Ser to Thr of the RNA polymerase region of BVDV or nucleotide 8443 (G to C) of the HCV genome or 282 Ser to Thr of the RNA polymerase region of HCV (FIG. 11; Lai et al. *J Virol.*, 1999, 73, 10129-36), and/or one or more drugs that are associated with such a mutation.

(ii) A pharmaceutical composition effective for the treatment of a Flaviviridae infection in a host, such as a human, comprising an effective amount of a 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable prodrug and/or salt thereof, optionally in a pharmaceutically acceptable carrier or diluent, in combination with interferon. Interferons include: Intron-A (interferon alpha-2b) by Schering, PEG-INTRON™ (pegylated interferon alpha-2b) by Schering, Roferon-A (interferon alfa-2a) by Roche, PEGASYS® (pegylated interferon alfa-2a) by Roche, INFERGEN® (interferon alfacon-1) by InterMune, OMNIFERON™ (natural interferon) by Viragen, ALBUFERON® (interferon alpha) by Human Genome Sciences, REBIF® (interferon beta-1a) by Ares-Serono, Omega Interferon by BioMedicine, Oral Interferon Alpha by Amarillo Biosciences, and Interferon gamma-1b by InterMune.

(iii) A pharmaceutical composition effective for the treatment of a Flaviviridae infection in a host, such as a human, comprising:
an effective amount of a 2', 3' and/or 5'-prodrug of a 2'-branched nucleoside, such as β-D-2'-branched pyrimidine nucleoside, for example β-D-2'-CH₃-riboC or a prodrug, including the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, including the 3'-valine ester prodrug, or a pharmaceutically acceptable salt thereof, or a pharmaceutically acceptable salt thereof, optionally in a pharmaceutically acceptable carrier or diluent;
in combination with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, and/or one or more drugs that are associated with such a mutation.

(iv) A method for treating a Flaviviridae infection in a host, such as a human, comprising administering an effective amount of a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or its pharmaceutically acceptable prodrug and/or salt to the human, optionally in a pharmaceutically acceptable carrier or diluent, in combination and/or alternation with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, for example, other than nucleotide 1214 (G to C) or 405 Ser to Thr of the RNA polymerase region of BVDV or nucleotide 8443 (G to C) of the HCV genome or 282 Ser to Thr of the RNA polymerase region of HCV (FIG. 11; Lai et al. *J Virol.*, 1999, 73, 10129-36), and/or one or more drugs that are associated with such a mutation.

(v) A method for treating a Flaviviridae infection in a host, such as a human, comprising administering an effective amount of a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable prodrug and/or salt thereof to the host, optionally in a pharmaceutically acceptable carrier or diluent, in combination and/or alternation with interferon. Interferons include: Intron-A (interferon alpha-2b) by Schering, PEG-INTRON™ (pegylated interferon alpha-2b) by Schering, Roferon-A (interferon alfa-2a) by Roche, PEGASYS® (pegylated interferon alfa-2a) by Roche, INFERGEN® (interferon alfacon-1) by InterMune, OMNIFERON™ (natural interferon) by Viragen, ALBUFERON® (interferon alpha) by Human Genome Sciences, REBIF® (interferon beta-1a) by Ares-Serono, Omega Interferon by BioMedicine, Oral Interferon Alpha by Amarillo Biosciences, and Interferon gamma-1b by InterMune.

(vi) A method for treating a patient infected with a Flaviviridae virus that is resistant to a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable salt thereof, comprising administering an effective amount of interferon, optionally in a pharmaceutically acceptable carrier or diluent, optionally in a manner that substantially eliminates the viral load.

(iv) A method for treating a patient infected with Flaviviridae comprising:
administering an effective amount of a 2', 3' and/or 5'-prodrug of a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable salt thereof, optionally in a pharmaceutically acceptable carrier or diluent;
in combination and/or alternation with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, and/or one or more drugs that are associated with such a mutation.

(v) A method for treating a patient infected with Flaviviridae comprising:
(a) administering to the patient an effective amount of a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable salt thereof; optionally in a pharmaceutically acceptable carrier or diluent;
(b) assaying the blood of the patient to test for seroconversion from wildtype to mutant virus; and
(c) administering an effective amount of interferon; optionally in a pharmaceutically acceptable carrier or diluent.

(vi) A method for assaying a sample suspected of containing a Flaviviridae resistant to a 2'-branched nucleoside, such as β-D-2'-branched pyrimidine nucleoside, for example β-D-2'-CH₃-riboC or a prodrug, such as the 3'-valine ester prodrug of β-D-2'-CH₃-riboC, or a β-D-2'-branched purine nucleoside, for example β-D-2'-CH₃-riboA or β-D-2'-CH₃-ribo-6-N-methylaminopurine or a prodrug, such as the 3'-valine ester prodrug, or a pharmaceutically acceptable salt thereof; comprising:
  (a) contacting a sample containing a Flaviviridae nucleic acid sequence with a detectable oligonucleotide probe having a sequence complementary a codon that encodes a serine in the highly conserved consensus sequence, XRX<u>S</u>GXXXT (SEQ ID NO: 63), of domain B of the RNA polymerase region of Flaviviridae (FIG. 11);
  (b) allowing the probe to hybridize to the sequence; and
  (c) detecting the hybridization of the probe the sequence.

(vii) A method for assaying a sample suspected of containing a Flaviviridae resistant to a 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof; comprising:
  (a) contacting a sample containing a Flaviviridae nucleic acid sequence with a detectable oligonucleotide probe having a sequence complementary to the cytidine at nucleotide 1214 of the RNA polymerase region of BVDV or the cytidine at nucleotide 8443 of HCV;
  (b) allowing the probe to hybridize to the sequence; and
  (c) detecting the hybridization of the probe to cytidine at nucleotide 1214 of the RNA polymerase region of BVDV or at nucleotide 8443 of HCV.

(viii) A method for treating a patient infected with Flaviviridae comprising:
  (a) administering an effective amount of a 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof; optionally in a pharmaceutically acceptable carrier or diluent;
  (b) obtaining a viral sample from the patient;
  (c) determining the replication fitness of the virus;
  (d) determining whether the replication fitness of the virus in the sample is less than the replication fitness of the wild-type virus, which indicates resistance to the 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof; and
  (e) administering an effective amount of interferon to those patients that are resistant to the 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof.

(ix) A method for treating a patient infected with Flaviviridae comprising:
  (a) administering an effective amount of a 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof; optionally in a pharmaceutically acceptable carrier or diluent;
  (b) obtaining a viral culture sample from the patient;
  (c) culturing the sample and comparing the plaque growth between the sample and wild type virus;
  (d) determining whether the plaque growth of the sample is smaller than the plaque growth of the wildtype, which indicates resistance to the 2'-branched nucleoside; and
  (e) administering an effective amount of interferon to those patients that are resistant to the 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof.

(x) A method for diagnosing the presence of a Flaviviridae resistant to a 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof, in a patient comprising:
  (a) obtaining a sample suspected of containing a Flaviviridae nucleic acid sequence;
  (b) contacting the sample with a detectable oligonucleotide probe having a sequence complementary a codon that encodes a serine in the highly conserved consensus sequence, XRX<u>S</u>GXXXT (SEQ ID NO: 63), of domain B of the RNA polymerase region of Flaviviridae (FIG. 11);
  (b) allowing the probe to hybridize to the sequence; and
  (c) detecting the hybridization of the probe the sequence to determine the presence of a Flaviviridae resistant to the 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof.

(xi) A method for diagnosing of the presence of a Flaviviridae resistant to the 2'-branched nucleoside, such as β-D-2'-branched pyrimidine nucleoside, for example β-D-2'-CH$_3$-riboC or a prodrug, such as the 3'-valine ester prodrug of β-D-2'-CH$_3$-riboC, or a β-D-2'-branched purine nucleoside, for example β-D-2'-CH$_3$-riboA or β-D-2'-CH$_3$-ribo-6-N-methylaminopurine or a prodrug, such as the 3'-valine ester prodrug, or a pharmaceutically acceptable salt thereof, in a patient comprising:
  (a) obtaining a sample suspected of containing a Flaviviridae nucleic acid sequence;

(b) contacting the sample with a detectable oligonucleotide probe having a sequence complementary to the cytidine at nucleotide 1214 of the RNA polymerase region of BVDV or the cytidine at nucleotide 8443 of HCV;

(b) allowing the probe to hybridize to the sequence; and (c) detecting the hybridization of the probe to cytidine at nucleotide 1214 of the RNA polymerase region of BVDV or at nucleotide 8443 of HCV to determine the presence of a Flaviviridae resistant to the 2'-branched nucleoside, such as β-D-2'-branched pyrimidine nucleoside, for example β-D-2'-CH$_3$-riboC or a prodrug, such as the 3'-valine ester prodrug of β-D-2'-$CH_3$-riboC, or a β-D-2'-branched purine nucleoside, for example β-D-2'-$CH_3$-riboA or β-D-2'-$CH_3$-ribo-6-N-methylaminopurine or a prodrug, such as the 3'-valine ester prodrug, or a pharmaceutically acceptable salt thereof.

The disclosed combination and/or alternation regimens are useful in the prevention and treatment of Flaviviridae infections, including BVDV, BDV, CSFV, DHF, yellow fever virus, shock syndrome, Japanese encephalitis virus, and HCV.

In addition, the corresponding amino acid sequences of the Flaviviridae viral markers diagnostic for long term response of Flaviviridae carriers to 2'-branched nucleoside therapy can be determined from the illustrative Flaviviridae nucleotide sequences.

In addition to identifying viral markers for the purposes of identifying Flaviviridae strains that are associated with 2'-branched nucleoside failure, the present invention can be utilized to also identify Flaviviridae strains that respond to 2'-branched nucleoside therapy. In this respect, the absence of viral markers correlated with 2'-branched nucleoside therapy can be used to prescribe a course of treatment that includes 2'-branched nucleoside as a modality for those individuals that carrier Flaviviridae lacking viral markers correlated with 2'-branched nucleoside therapy failure.

In another embodiment, the invention provides an oligonucleotide primer for amplifying an Flaviviridae nucleic acid sequence. In one embodiment, the oligonucleotide is at least 14 nucleotides in length and hybridizes under sequence-specific, stringent hybridization conditions to a nucleotide sequence that contains the marker correlated with therapy failure.

Oligonucleotide sequences used as the hybridizing region of a primer can also be used as the hybridizing region of a probe. Suitability of a primer sequence for use as a probe depends on the hybridization characteristics of the primer. Similarly, an oligonucleotide used as a probe can be used as a primer.

Additionally, the invention provides a method, materials and a kit to detect proteins, peptides or peptide fragments that contain amino acids (as described extensively herein) that are predictive of the long term response of an Flaviviridae carrier to 2'-branched nucleoside therapy, or antibodies to those proteins, peptides or peptide fragments. Host sera or tissue can be tested for either the protein or peptide or the antibody to the protein or peptide, depending on convenience and perhaps concentration of the diagnostic material.

The protein, peptide or peptide fragment can be confirmed by reaction with an antibody, preferably a monoclonal antibody, for example using a Western blot method. Alternatively, the protein or peptide can be isolated and sequenced or otherwise identified by any means known in the art, including by 2D PAGE. In one embodiment, a reactive antibody binds to an Flaviviridae protein or peptide sequence that includes a threonine rather than serine in the highly conserved consensus sequence, XRXSGXXXT (SEQ ID NO: 63), of domain B of the RNA polymerase region, for example at position 405 of the RNA polymerase region of BVDV genome or at position 282 of the RNA polymerase region of the HCV genome.

In another embodiment, the reactive antibody binds specifically to a peptide sequence that includes a threonine rather than serine in the highly conserved consensus sequence, XRXSGXXXT (SEQ ID NO: 63), of domain B of the RNA polymerase region, for example at position 405 of the RNA polymerase region of BVDV genome or at position 282 of the RNA polymerase region of the HCV genome, which represent a specific point mutations in the RNA polymerase region of Flaviviridae that is correlated with therapy failure.

In specific embodiments, an antibody is used that binds to at least one peptide or peptide fragment encoded for by the nucleic acid sequences in sequence ID Nos. 1-31.

In specific embodiments, an antibody is used that binds to at least one peptide or peptide fragment encoded for by the nucleic acid sequences in sequence ID Nos. 32-62.

I. Definitions

As used herein, the term "resistant virus" refers to a virus that exhibits a three, and more typically, five or greater fold increase in $EC_{50}$ compared to naive virus.

The term "amino acid" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration, but can also be in the D-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The abbreviations of amino acids used herein are described in Table 1.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic Acid | Asp | D | GAC | GAU | GAC | GAU | | |
| Glutamic Acid | Glu | E | GAA | GAG | | | | |
| Phenylalanine | Phe | F | UCC | UUU | | | | |
| Clycine | Gly | G | GGA | GCG | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | GUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |

TABLE 1-continued

| Amino Acids | | | Codons | | | | | |
|---|---|---|---|---|---|---|---|---|
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

"Amplification reagents" refer to the various buffers, enzymes, primers, deoxynucleoside triphosphates (both conventional and unconventional), and primers used to perform the selected amplification procedure.

"Amplifying" or "Amplification", which typically refers to an "exponential" increase in target nucleic acid, is being used herein to describe both linear and exponential increases in the numbers of a select target sequence of nucleic acid.

"Bind(s) substantially" refers to complementary hybridization between an oligonucleotide and a target sequence and embraces minor mismatches that can be accommodated by reducing the stringency of the hybridization media to achieve the desired priming for the PCR polymerases or detection of hybridization signal.

"Hybridizing" refers to the binding of two single stranded nucleic acids via complementary base pairing.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

"Nucleotide polymerases" refers to enzymes able to catalyze the synthesis of DNA or RNA from nucleoside triphosphate precursors. In amplification reactions, the polymerases are template-dependent and typically add nucleotides to the 3'-end of the polymer being formed. The polymerase can be thermostable as described in U.S. Pat. Nos. 4,889,818 and 5,079,352.

The term "oligonucleotide" refers to a molecule comprised of two or more deoxyribonucleotides or ribonucleotides, such as primers, probes, nucleic acid fragments to be detected, and nucleic acid controls. The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., *Meth. Enzymol.* 1979, 68:90-99; the phosphodiester method of Brown et al, *Meth. Enzymol.,* 1979, 68:109-151; the diethylphosphoramidite method of Beaucage et al., *Tetrahedron Lett.,* 1981, 22:1859-1862; and the solid support method of U.S. Pat. No. 4,458,066.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from about 14 or about 15 to 25 or 30 nucleotides. Short primer molecules generally require cooler temperatures to form sufficiently stable hybrid complexes with the template. A primer need not reflect the exact sequence of the template but must be sufficiently complementary to hybridize with a template.

The term "primer" can refer to more than one primer, particularly in the case where there is some ambiguity in the information regarding one or both ends of the target region to be amplified. For instance, if a region shows significant levels of polymorphism in a population, mixtures of primers can be prepared that will amplify alternate sequences. A primer can be labeled, if desired, by incorporating a label detectable by spectroscopic, photochemical, biochemical, immunochemical, or chemical means. For example, useful labels include 32P, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

"Probe" refers to an oligonucleotide which binds through complementary base pairing to a subsequence of a target nucleic acid. It will be understood by one of skill in the art that probes will typically substantially bind target sequences lacking complete complementarity with the probe sequence depending upon the stringency of the hybridization conditions. The probes are preferably directly labeled as with isotopes or indirectly labeled such as with biotin to which a streptavidin complex can later bind. By assaying for the presence or absence of the probe, one can detect the presence or absence of the target.

"Subsequence" refers to a sequence of nucleic acids that comprise a part of a longer sequence of nucleic acids.

The term "target region" refers to a region of a nucleic acid to be analyzed and can include a polymorphic region.

The term alkyl, as used herein, unless otherwise specified, refers to a saturated straight, branched, or cyclic, primary, secondary, or tertiary hydrocarbon typically of $C_1$ to $C_{10}$, and specifically includes methyl, $CF_3$, $CCl_3$, $CFCl_2$, $CF_2Cl$, ethyl, $CH_2CF_3$, $CF_2CF_3$, propyl, isopropyl, cyclopropyl, butyl, isobutyl, /-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups, and particularly includes halogenated alkyl groups, and even more particularly fluorinated alkyl groups. Moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term base refers to any purine or pyrimidine base including, but not limited to, guanine, adenine, hypoxanthine, 2,6-diaminopurine, 6-chloropurine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl punne, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-amino-pyrimidine, $N^2$-alkylpurines, $N^2$-alkyl-6-thiopurines, 5-azacytidinyl, 5-aza-uracilyl, triazolopyridinyl, imidazolopyridinyl, pyrrolopyrimidinyl, pyrazolopyrimidinyl, a base of the formula:

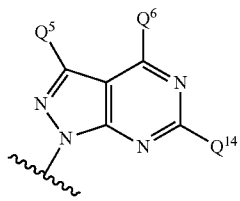

(i)

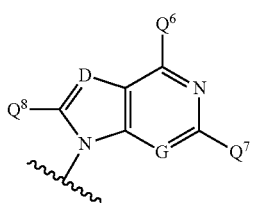

(ii)

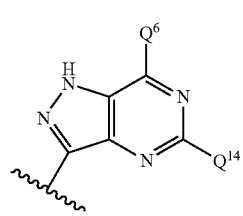

(iii)

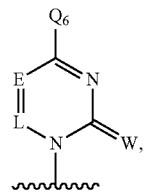

(iv)

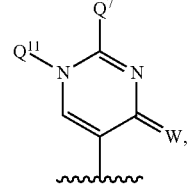

(v)

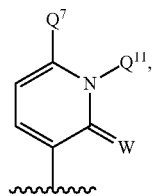

(vi)

wherein:

G and L are each independently CH or N;

D is N, CH, C—CN, C—$NO_2$, C—$C_{1-3}$ alkyl, C—$NHCONH_2$, C—$CONQ^{11}Q^{11}$, C—$CSNQ^{11}Q^{11}$, $CCOOQ^{11}$, C—C(=NH)$NH_2$, C-hydroxy, C—$C_{1-3}$alkoxy, C-amino, C—C $C_{1-4}$alkyl-amino, C-di($C_{1-4}$ alkyl)amino, C-halogen, C-(1,3-oxazol-2-yl), C-(1,3-thiazol-2-yl), or C-(imidazol-2-yl); wherein alkyl is unsubstituted or substituted with one to three groups independently selected from halogen, amino, hydroxy, carboxy, and $C_{1-3}$ alkoxy;

E is N or $CQ^5$;

W is O, S, or NR;

R is H, OH, alkyl;

$Q^6$ is H, OH, SH, $NH_2$, $C_{1-4}$ alkylamino, di($C_{1-4}$ alkyl)amino, $C_{3-6}$ cycloalkylamino, halogen, $C_{1-4}$ alkyl, $C_{1-4}$ alkoxy, or $CF_3$;

$Q^5$ is H, $C_{1-6}$ alkyl, $C_{2-6}$ alkenyl, $C_{2-6}$ alkynyl, $C_{1-4}$ alkylamino, $CF_3$, halogen, N, CN, $NO_2$, $NHCONH_2$, $CONQ^{11}Q^{11}$, $CSNQ^{11}Q^{11}$, $COOQ^{11}$, C(=NH)$NH_2$, hydroxy, $C_{1-3}$alkoxy, amino, $C_{1-4}$ alkylamino, di($C_{1-4}$ alkyl)amino, halogen, 1,3-oxazol-2-yl, 1,3-thiazol-2-yl, or imidazol-2-yl; wherein alkyl is unsubstituted or substituted with one to three groups independently selected from halogen, amino, hydroxy, carboxy, and $C_{1-3}$ alkoxy;

$Q^7$ and $Q^{14}$ are each independently selected from the group consisting of H, $CF_3$, OH, SH, OR, SR $C_{1-4}$ alkyl, amino, $C_{1-4}$ alkylamino, $C_{3-6}$ cycloalkylamino, and di($C_{1-4}$ alkyl) amino;

$Q^{11}$ is independently H or $C_{1-6}$ alkyl;

$Q^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, ($C_{1-4}$ alkyl)$_{0-2}$aminomethyl, $NH_2$, CN, $NO_2$, $C_{1-3}$ alkyl, $NHCONH_2$, $CONQ^{11}Q^{11}$, $CSNQ^{11}Q^{11}$, $COOQ^{11}$, C(=NH)$NH_2$, 1,3-oxazol-2-yl, 1,3-thiazol-2-yl, or imidazol-2-yl, wherein alkyl is unsubstituted or substituted with one to three groups independently selected from halogen, amino, hydroxy, carboxy, and $C_{1-3}$ alkoxy;

a base of the formula:

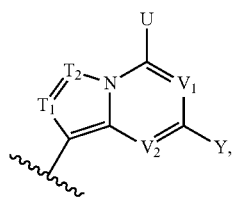
(A)

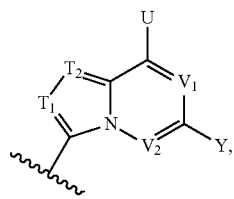
(B)

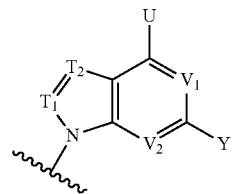
(C)

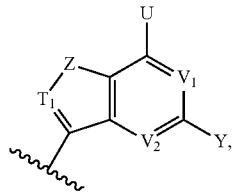
(D)

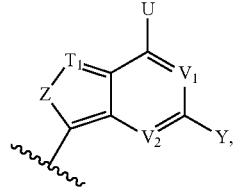
(E)

wherein:
$T_1$ and $T_2$ are independently selected from N, CH, or C-$Q^{16}$, $Q^{16}$, U, and Y are independently selected from is H, OH, substituted or unsubstituted alkyl, substituted or unsubstituted alkenyl, substituted or unsubstituted alkynyl, cycloalkyl, CO-alkyl, CO-aryl, CO-alkoxyalkyl, chloro, bromo, fluoro, iodo, $OR^4$, $NR^4R^5$ or $SR^5$, Br-vinyl, —O-alkyl, —O-alkenyl, —O-alkynyl, —O-aryl, —O—aralkyl, —O-acyl, —O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, CN, $N_3$, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$, $(CH_2)_mCONH_2$, $C_{1-4}$ alkylamino, di($C_{1-4}$ alkyl)amino, $C_{3-6}$ cycloalkylamino, $C_{1-4}$ alkoxy, $C_{1-4}$ alkoxycarbonyl, $C_{1-6}$ alkylthio, $C_{1-6}$ alkylsulfonyl, ($C_{1-4}$ alkyl)$_{0-2}$aminomethyl, or —NHC(=NH)$NH_2$;
$R^4$ and $R^5$ are independently selected from hydrogen, acyl (including lower acyl), or alkyl (including but not limited to methyl, ethyl, propyl and cyclopropyl);
m is 0, 1, 2, 3, 4, 5, 6, 7, 8, 9, or 10;
Z is S, SO, $SO_2$, C=O, or $NQ^{20}$;
$Q^{20}$ is H or alkyl; and
$V^1$ and $V^2$ are independently selected from CH or N;
a base of the formula:

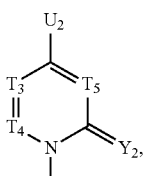
(F)

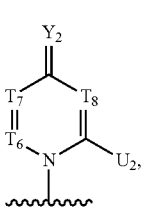
(G)

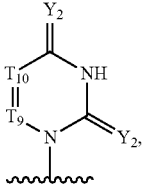
(H)

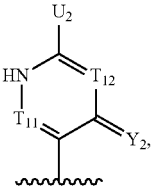
(I)

wherein:
$T_3$ and $T_4$ are independently selected from N or C$Q^{22}$;
$Q^{22}$ is independently selected from H, OH, substituted or unsubstituted alkyl, substituted or unsubstituted alkenyl, substituted or unsubstituted alkynyl, cycloalkyl, CO-alkyl, CO-aryl, CO-alkoxyalkyl, chloro, bromo, fluoro, iodo, $OR^4$, $NR^4R^5$ or $SR^5$, Br-vinyl, —O-alkyl, —O-alkenyl, —O-alkynyl, —O-aryl, —O— aralkyl, —O-acyl, —O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, CN, $N_3$, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$, $(CH_2)_mCONH_2$, $C_{1-4}$ alkylamino, di($C_{1-4}$ alkyl)amino, $C_{3-6}$ cycloalkylamino, $C_{1-4}$ alkoxy, $C_{1-4}$ alkoxycarbonyl, $C_{1-6}$ alkylthio, $C_{1-6}$ alkylsulfonyl, ($C_{1-4}$ alkyl)$_{0-2}$aminomethyl, or —NHC(=NH)$NH_2$;
$T_5$ is NH;
$R^4$ and $R^5$ are independently selected from hydrogen, acyl (including lower acyl), or alkyl (including but not limited to methyl, ethyl, propyl and cyclopropyl);
m is 0, 1, 2, 3, 4, 5, 6, 7, 8, 9, or 10;
$T_6$, $T_7$, $T_8$, $T_9$, $T_{10}$, $T_{11}$, and $T_{12}$ are independently selected from N or CH;
$U_2$ is H, straight chained, branched or cyclic alkyl, CO-alkyl, CO-aryl, CO— alkoxyalkyl, chloro, bromo, fluoro, iodo, $OR^4$, $NR^4R^5$ or $SR^5$;

$Y_2$ is O, S, NH, NR or $CQ^{24}Q^{26}$ where R is H, OH, or alkyl; $Q^{24}$ and $Q^{26}$ are independently selected from H, alkyl, straight chained, branched or cyclic alkyl, CO-alkyl, CO-aryl, CO-alkoxyalkyl, chloro, bromo, fluoro, iodo, $OR^4$, $NR^4R^5$ or $SR^5$.

Further examples of purine bases include, but are not limited to, guanine, adenine, hypoxanthine, 2,6-diaminopurine, 6-chloropurine, and 6-N-methylamino purine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term acyl or O-linked ester refers to a group of the formula C(O)R', wherein R' is an straight, branched, or cyclic alkyl (including lower alkyl), amino acid, aryl including phenyl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoroheptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

As used herein, the term "substantially free of" or "substantially in the absence of" refers to a nucleoside composition that includes at least 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 95% to 98% by weight, and even more preferably 99% to 100% by weight, of the nucleoside, the remainder comprising other chemical species or enantiomers.

The term host, as used herein, refers to an unicellular or multicellular organism in which the virus can replicate, including cell lines and animals, and preferably a human. Alternatively, the host can be carrying a part of the Flaviviridae viral genome, whose replication or function can be altered by the compounds of the present invention. The term host specifically refers to infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

II. -Branched Nucleosides and Prodrugs Thereof

In the broadest embodiment, the present invention provides a method to treat a Flaviviridae infection that is resistant to a 2'-branched nucleoside. In one embodiment, the 2'-branched nucleoside is a purine, or a purine derivative such as a pyrrolo-purine. In a preferred embodiment, the 2'-branched nucleoside is a pyrimidine. Other sub-embodiments include the 2'-alkyl and 2'-methyl-branched pyrimidine nucleosides, including the 2'-branched uracil and 2'-branched cytosine nucleosides. In another embodiment, the 2'-branched nucleoside is a purine. Other sub-embodiments include the 2'-alkyl and 2'-methyl-branched purine nucleosides, including the 2'-branched adenosine nucleosides and the 2'-branched 6-N-methylamino purine nucleosides.

In a specific embodiment, the 2'-branched pyrimidine nucleoside is represented by the compound β-D-2'-$CH_3$-riboC, which is represented by the formula:

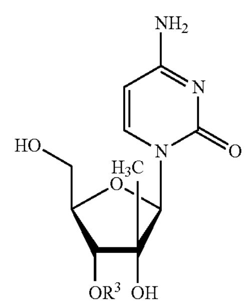

wherein $R^3$ is H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein $R^3$ is H or phosphate when administered in vivo.

In another specific embodiment, the 2'-branched purine nucleoside is represented by the compound β-D-2'-$CH_3$-ribo-6-N-methylaminopurine, which is represented by the formula:

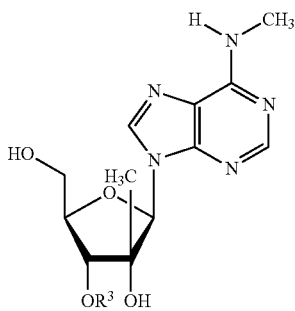

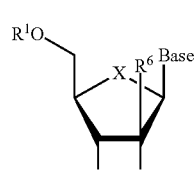

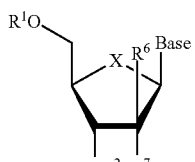

wherein R³ is H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein R³ is H or phosphate when administered in vivo.

In one embodiment of the invention, the 2'-branched nucleoside is of the general formula:

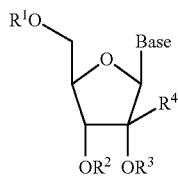

or its pharmaceutically acceptable prodrug and/or salt, wherein

R¹, R², and R³ are independently H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein R¹, R² or R³ is independently H or phosphate when administered in vivo; and R⁴ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO₂, NH₂, —NH(lower alkyl), —NH(acyl), —N(lower alkyl)₂, or —N(acyl)₂;

and Base is a purine or pyrimidine as further described herein.

In another embodiment of the invention, the 2'-branched nucleoside is of the general formula:

or its pharmaceutically acceptable prodrug and/or salt, wherein

Base is a purine or pyrimidine base as defined herein;

R¹, R² and R³ are independently H, phosphate (including mono-, di- or triphosphate and a stabilized phosphate); straight chained, branched or cyclic alkyl (including lower alkyl); acyl (including lower acyl); CO-alkyl, CO-aryl, CO-alkoxyalkyl, CO-aryloxyalkyl, CO-substituted aryl, sulfonate ester (including alkyl or arylalkyl sulfonyl including methanesulfonyl); benzyl, wherein the phenyl group is optionally substituted with one or more substituents as described in the definition of aryl given herein; alkylsulfonyl, arylsulfonyl, aralkylsulfonyl, lipid (including a phospholipid); amino acid; carbohydrate; peptide; cholesterol; or a pharmaceutically acceptable leaving group that provides a compound wherein R¹, R² or R³ is independently H or phosphate when administered in vivo;

R⁶ is alkyl (including lower alkyl and halogenated alkyl), CH₃, CF₃, azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), CF₃, chloro, bromo, fluoro, iodo, NO₂, NH₂, —NH(lower alkyl), —NH(acyl), —N(lower alkyl)₂, —N(acyl)₂; and R⁷ is hydrogen, OR³, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), fluorine, chlorine, bromine, iodine, NO₂, NH₂, —NH(lower alkyl), —NH(acyl), —N(lower alkyl)₂, —N(acyl)₂; and X is O, S, SO₂ or CH₂.

and Base is a purine or pyrimidine as further described herein.

In yet another embodiment the invention, the 2'-branched nucleoside is of the general formula:

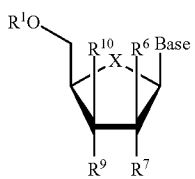

wherein:

Base is a purine or pyrimidine base as defined herein;

R⁶ is alkyl (including lower alkyl and halogenated alkyl), CH₃, CF₃, azido, cyano, alkenyl, alkynyl, Br-vinyl, 2-Brethyl, —C(O)O(alkyl), —C(O)O(lower alkyl), —O(acyl), —O(lower acyl), —O(alkyl), —O(lower alkyl), —O(alkenyl), $CF_3$, fluoro, chloro, bromo, iodo, $NO_2$, $NH_2$, —NH(lower alkyl), —NH(acyl), —N(lower alkyl)$_2$, —N(acyl)$_2$;

$R^7$ is $OR^2$, hydroxy, alkyl (including lower alkyl), azido, cyano, alkenyl, alkynyl, Br-vinyl, halo-vinyl, —C(O)O(alkyl), —C(O)O(lower alkyl), —O(acyl), —O(lower acyl), —O(alkyl), —O(lower alkyl), —O(alkenyl), fluorine, chlorine, bromine, iodine, $NO_2$, $NH_2$, —NH(lower alkyl), —NH(acyl), —N(lower alkyl)$_2$, —N(acyl)$_2$;

$R^9$ is hydrogen, $OR^3$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^{10}$ is H, alkyl (including lower alkyl), fluorine, chlorine, bromine or iodine;

$R^1$, $R^2$ and $R^3$ are independently H, phosphate (including mono-, di- or triphosphate and a stabilized phosphate); straight chained, branched or cyclic alkyl (including lower alkyl); acyl (including lower acyl); CO-alkyl, CO-aryl, CO-alkoxyalkyl, CO-aryloxyalkyl, CO-substituted aryl, sulfonate ester (including alkyl or arylalkyl sulfonyl including methanesulfonyl); benzyl, wherein the phenyl group is optionally substituted with one or more substituents as described in the definition of aryl given herein; alkylsulfonyl, arylsulfonyl, aralkylsulfonyl, lipid (including a phospholipid); amino acid; carbohydrate; peptide; cholesterol; or a pharmaceutically acceptable leaving group that provides a compound wherein $R^1$, $R^2$ or $R^3$ is independently H or phosphate when administered in vivo; and X is O, S, $SO_2$ or $CH_2$.

General Synthesis of 2'-Branched Nucleosides:

1. Glycosylation of the Nucleobase with an Appropriately Modified Sugar

The key starting material for this process can be an appropriately substituted sugar with a 2'-OH and 2'-H, with the appropriate leaving group (LG), for example an acyl group or a chloro, bromo, fluoro or iodo. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$-CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or $R^4$—$SiMe_3$ (wherein $R^4$ is defined below) in TBAF with the ketone with the appropriate non-protic solvent at a suitable temperature, yields the 2'-alkylated sugar. The alkylated sugar can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 1. Alternatively, the deoxyribo-nucleoside can be used. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 1:

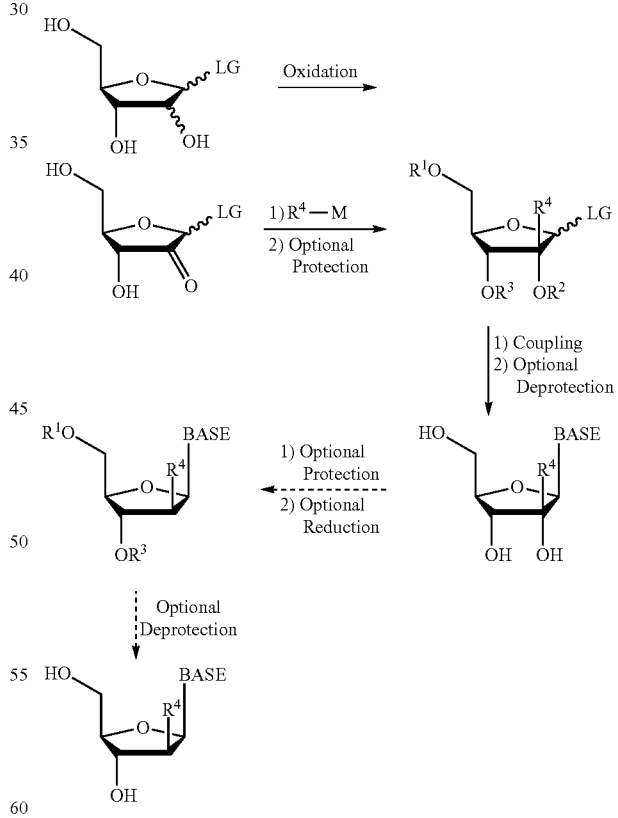

wherein:
LG is a leaving group;
$R^1$, $R^2$, and $R^3$ are independently H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein $R^1$, $R^2$ or $R^3$ is independently H or phosphate when administered in vivo; and $R^4$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, or —N(acyl)$_2$.

2. Modification of a Pre-Formed Nucleoside

The key starting material for this process can be an appropriately substituted nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$-CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 2. Alternatively, deoxyribo-nucleoside can be used. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 2

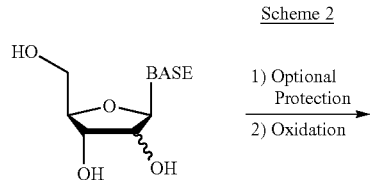

1) Optional Protection
2) Oxidation

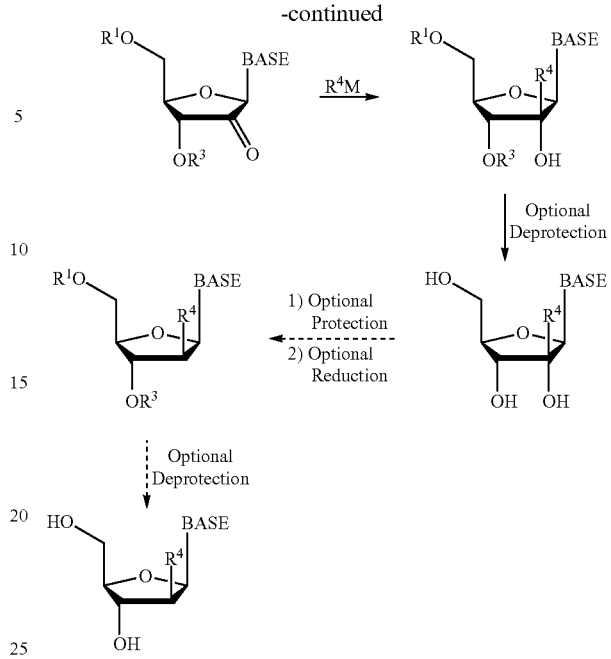

wherein:
$R^1$ and $R^3$ are independently H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein $R^1$ or $R^3$ is independently H or phosphate when administered in vivo; and $R^4$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, or —N(acyl)$_2$.

General Synthesis of 2'-Branched Pyrimidine Nucleoside
1. Glycosylation of the Pyrimidine with an Appropriately Modified Sugar A representative general method for the preparation of 2'-branched pyrimidine nucleoside is outlined in Scheme 3. This scheme illustrates the 2' branched pyrimidine nucleoside in the β-D-ribo configuration. Alternatively, one skilled in the art could modify the general scheme to produce 2'-β-L-pyrimidine nucleoside. The key starting material for this process can be an appropriately substituted sugar with a 2'-OH and 2'-H, with the appropriate leaving group (LG), for example an acyl group or a chloro, bromo, fluoro or iodo. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, MnO$_2$, ruthenium tetroxide, phase transfer catalysts such as chromic acid or permanganate supported on a polymer, Cl$_2$-pyridine, H$_2$O$_2$-ammonium molybdate, NaBrO$_2$-CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or R$^4$—SiMe$_3$ in TBAF with the ketone with the appropriate non-protic solvent at a suitable temperature, yields the 2'-alkylated sugar. The alkylated sugar can be optionally protected with a suitable protecting group, preferably with an acyl or silyl group, by methods well known to those skilled in the art, as taught by Greene et al. *Protective Groups in Organic Synthesis*. John Wiley and Sons, Second Edition, 1991.

The optionally protected sugar can then be coupled to a prymidine base by methods well known to those skilled in the art, as taught by Townsend *Chemistry of Nucleosides and Nucleotides*. Plenum Press, 1994. For example, an acylated sugar can be coupled to a silylated pyrimidine, such as cytidine, with a lewis acid, such as tin tetrachloride, titanium tetrachloride or trimethylsilyltriflate in the appropriate solvent at a suitable temperature. Alternatively, a halo-sugar can be coupled to a silylated pyrimidine, such as a cytidine, with the presence of trimethylsilyltriflate.

wherein R$^1$, R$^2$ or R$^3$ is independently H or phosphate when administered in vivo; and R$^4$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO$_2$, NH$_2$, —NH(lower alkyl), —NH(acyl), —N(lower alkyl)$_2$, or —N(acyl)$_2$.

2. Modification of a Pre-Formed 2'-Branched Pyrimidine Nucleoside

The key starting material for this process can be an appropriately substituted 2'-branched pyrimidine nucleoside with a 2'-OH and 2'-H. The 2'-branched pyrimidine nucleoside can be purchased or can be prepared by any known means including standard coupling techniques. The 2'-branched pyrimidine nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected 2'-branched pyrimidine nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's

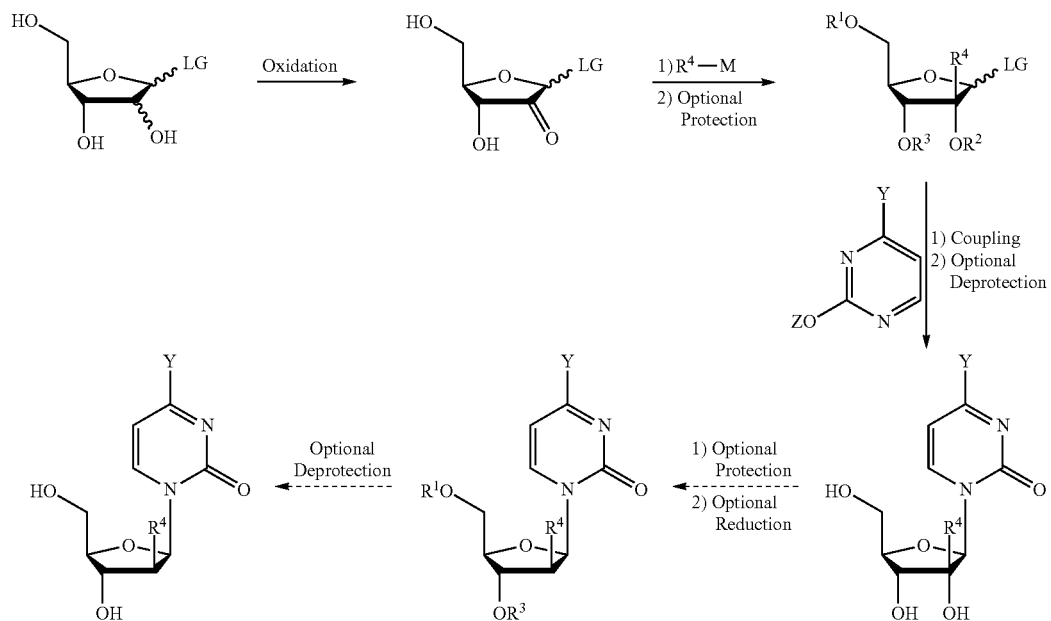

Scheme 3 wherein:

R$^1$, R$^2$, and R$^3$ are independently H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound reagent (pyridinium chlorochromate), pyridinium dichromate, acid dichromate, potassium permanganate, MnO$_2$, ruthenium tetroxide, phase transfer catalysts such as chromic acid or permanganate supported on a polymer, Cl$_2$-pyridine, H$_2$O$_2$-ammonium molybdate, NaBrO$_2$-CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the 2'-branched pyrimidine nucleoside can be deprotected by methods well known to those skilled in the art, as taught by et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 4. Alternatively, deoxyribo-nucleoside can be used. To obtain these nucleosides, the formed ribonucleoside can optionally be protected by methods well known to those skilled in the art, as taught by Greene et al. *Protective Groups in Organic Synthesis*. John Wiley and Sons, Second Edition, 1991, and then the 2'-OH can be reduced with a suitable reducing agent. Optionally, the 2'-hydroxyl can be activated to facilitate reduction; i.e. via the Barton reduction.

below. This scheme illustrates the synthesis of 2'-branched purine nucleoside in the β-D-ribo configuration. Alternative, it is well appreciated to those skilled in the art are able to prepare the β-L-ribo configuration using the appropriate starting material. The starting material is a 3,5-bis protected alkyl furanoside, such as methyl furanoside, of structural formula (i). The C-2 hydroxyl group is then oxidized with a suitable oxidizing agent, such as a chromium trioxide or chromate reagent or Dess-Martin periodinane, or by Swern oxidation, to afford a C-2 ketone of structural formula (ii). Addition of a Grignard reagent, such as an alkyl, alkenyl, or alkynyl magnesium halide (for example, MeMgBr, EtMgBr,

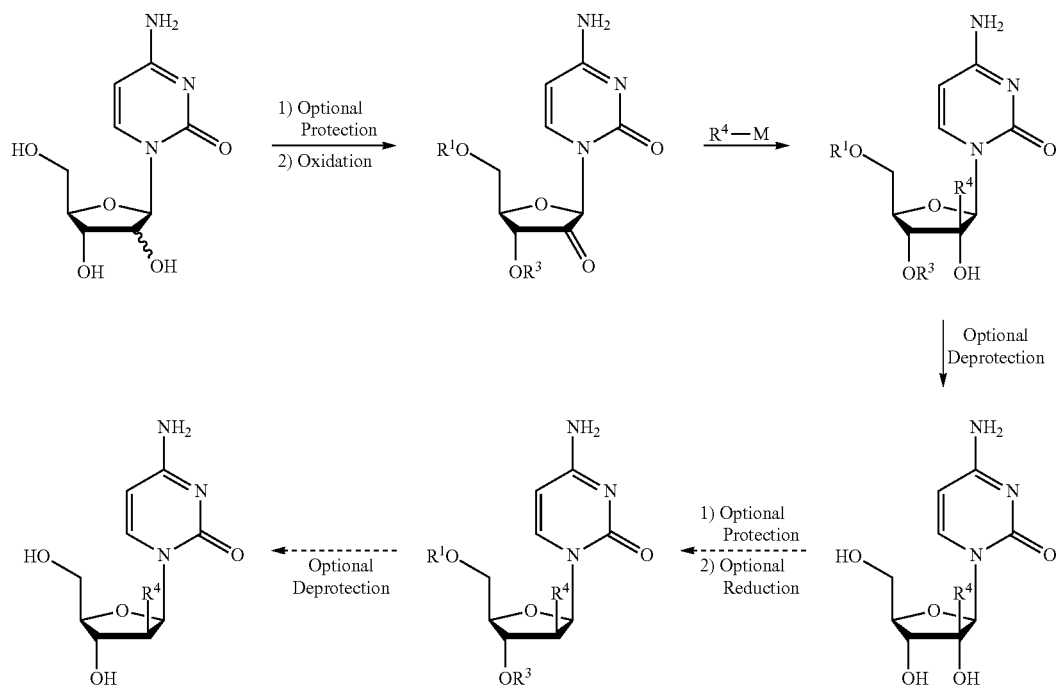

Scheme 4 wherein:

R¹ and R³ are independently H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein R¹ or R³ is independently H or phosphate when administered in vivo; and R⁴ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO₂, NH₂, —NH(lower alkyl), —NH(acyl), —N(lower alkyl)₂, or —N(acyl)₂.

General Synthesis of 2'-Branched Purine Nucleoside

1. Glycosylation of the Pyrimidine with an Appropriately Modified Sugar

A representative general method for the preparation of 2'-branched purine nucleoside is outlined in Scheme 5 vinylMgBr, allylMgBr, and ethynylMgBr) or an alkyl, alkenyl, or alkynyl lithium, such as MeLi, across the carbonyl double bond of (ii) in a suitable organic solvent, such as tetrahydrofuran, diethyl ether, and the like, affords the C-2 tertiary alcohol of structural formula (iii). A good leaving group (such as F, Cl, Br, and I) is next introduced at the C-1 (anomeric) position of the furanose sugar derivative by treatment of the furanoside of formula (iii) with a hydrogen halide in a suitable organic solvent, such as hydrogen bromide in acetic acid, to afford the intermediate furanosyl halide (iv). A C-sulfonate, such as methanesulfonate (MeSO₂O—), trifluoromethanesulfonate (CF₃SO₂O—) or p-toluenesulfonate (—OTs), may also serve as a useful leaving group in the subsequent reaction to generate the glycosidic (nucleosidic) linkage. The nucleosidic linkage is constructed by treatment of the intermediate of structural formula (iv) with the metal salt (such as lithium, sodium, or potassium) of an appropriately substituted 1H-pyrrolo[2,3-d]pyrimidine (v), such as an appropriately substituted 4-halo-1H-pyrrolo[2,3-d]pyrimidine, which can be generated in situ by treatment with an alkali hydride (such as sodium hydride), an alkali hydroxide (such as potassium hydroxide), an alkali carbonate (such as potassium carbonate), or an alkali hexamethyldisilazide (such as NaHMDS)

in a suitable anhydrous organic solvent, such as acetonitrile, tetrahydrofuran, 1-methyl-2-pyrrolidinone, or N,N-dimethyl-formamide (DMF). The displacement reaction can be catalyzed by using a phase-transfer catalyst, such as TDA-1 or triethylbenzylammonium chloride, in a two-phase system (solid-liquid or liquid-liquid). The optional protecting groups in the protected nucleoside of structural formula (vi) are then cleaved following established deprotection methodologies, such as those described in T. W. Greene' and P. G. M. Wuts, "Protective Groups in Organic Synthesis," P ed., John Wiley & Sons, 1999. Optional introduction of an amino group at the 4-position of the pyrrolo[2,3-d]pyrimidine nucleus is effected by treatment of the 4-halo intermediate (vi) with the appropriate amine, such as alcoholic ammonia or liquid ammonia, to generate a primary amine at the C-4 position (—$NH_2$), an alkylamine to generate a secondary amine (—NHR), or a dialkylamine to generate a tertiary amine (—NRR'). A 7H-pyrrolo[2,3-d]pyrimidin-4 (3H)one compound may be derived by hydrolysis of (vi) with aqueous base, such as aqueous sodium hydroxide. Alcoholysis (such as methanolysis) of 1-6 affords a C-4 alkoxide (—OR), whereas treatment with an alkyl mercaptide affords a C-4 alkylthio (—SR) derivative. Subsequent chemical manipulations well-known to practitioners of ordinary skill in the art of organic/medicinal chemistry may be required to attain the desired compounds of the present invention.

wherein:
$P^1$ and $P^2$ are independently a protecting group; alternatively, $P^1$ and $P^2$ can come together to form a cyclic protecting group;
$R^5$ and $R^6$ are independently alkyl group;
M is Li, Na, or K;
$X^1$ and $X^2$ are independently F, Cl, Br, or I;
$R^7$, $R^8$, and $R^9$ are independently hydrogen, hydroxyl, halogen, alkoxy, amino, alkylamino, or alkyl.

Synthesis of B-D-2'-$CH_3$-riboC

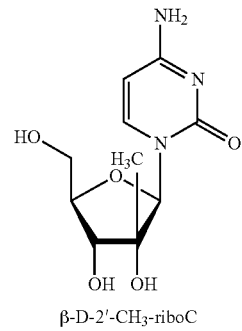

β-D-2'-$CH_3$-riboC

The following syntheses provided are non-limiting steps to achieve the compound β-D-2'-$CH_3$-riboC. One of ordi-

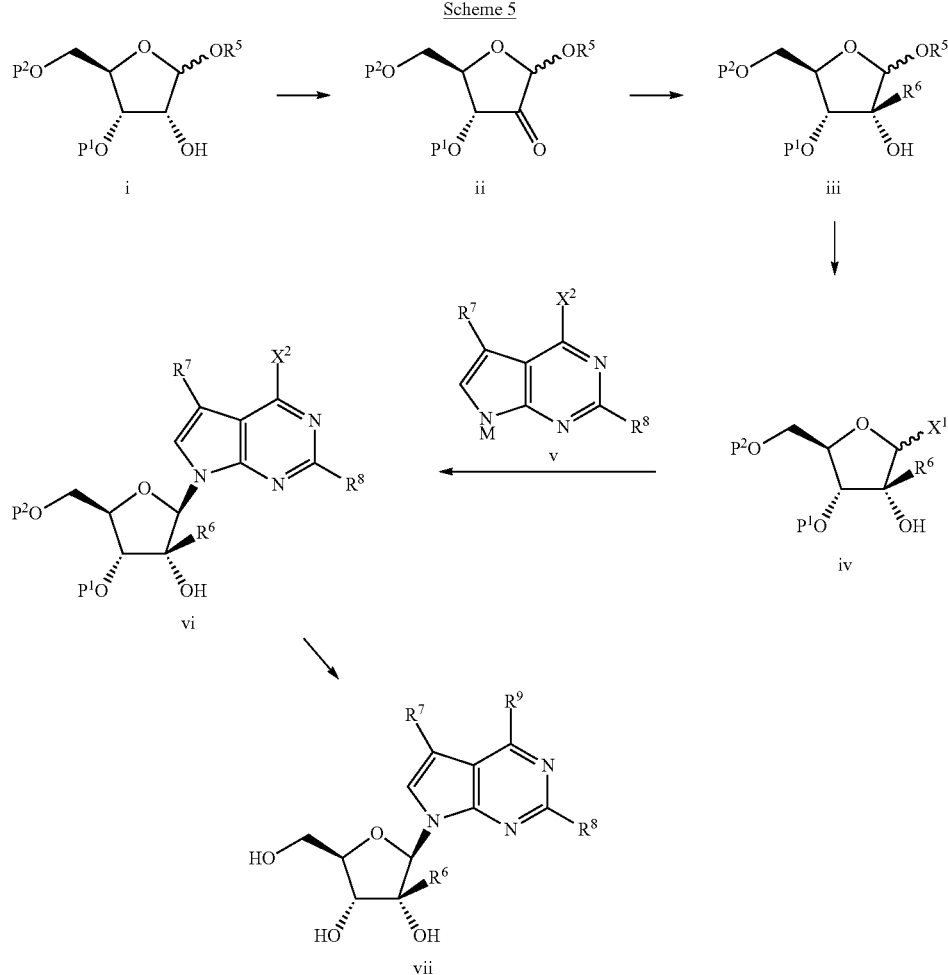

nary skill in the art may modify the synthesis in any known manner to achieve the compound β-D-2'-CH₃-riboC.

1. Glycosylation of the Nucleobase with an Appropriately Modified Sugar

The key starting material for this process can be an appropriately substituted sugar with a 2'-OH and 2'-H, with the appropriate leaving group (LG), for example an acyl group or a chloro, bromo, fluoro or iodo. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, MnO₂, ruthenium tetroxide, phase transfer catalysts such as chromic acid or permanganate supported on a polymer, Cl₂-pyridine, H₂O₂-ammonium molybdate, NaBrO₂-CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or CH₃—SiMe₃ in TBAF with the ketone with the appropriate non-protic solvent at a suitable temperature, yields the 2'-methyl sugar. The methyl sugar can be optionally protected with a suitable protecting group, preferably with an acyl or silyl group, by methods well known to those skilled in the art, as taught by Greene et al. *Protective Groups in Organic Synthesis*. John Wiley and Sons, Second Edition, 1991.

The optionally protected sugar can then be coupled to the BASE by methods well known to those skilled in the art, as taught by Townsend *Chemistry of Nucleosides and Nucleotides*. Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the 2'-methyl-nucleoside can be deprotected by methods well known to those skilled in the art, as taught by Greene et al. *Protective Groups in Organic Synthesis*. John Wiley and Sons, Second Edition, 1991.

The synthesis of a 2'-methyl-nucleoside is shown in Scheme 6.

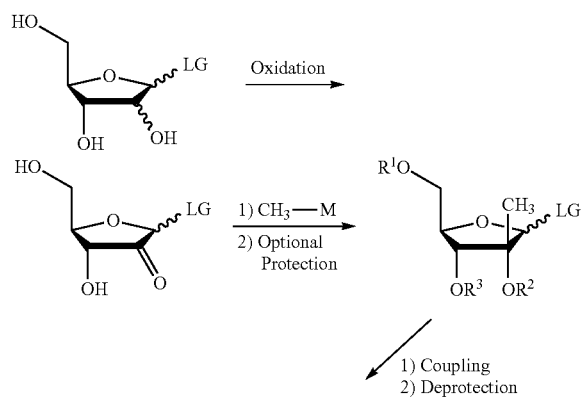

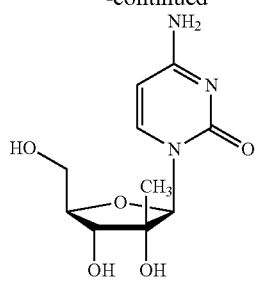

wherein:

LG is a leaving group; and $R^1$ $R^2$, and $R^3$ are independently H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein $R^1$, $R^2$ or $R^3$ is independently H or phosphate when administered in vivo.

2. Modification of a Pre-Formed 2'-Methyl Nucleoside

The key starting material for this process can be an appropriately substituted 2'-methyl-cytidine nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*. John Wiley and Sons, Second Edition, 1991.

The appropriately protected 2'-methyl-cytidine nucleoside can then be oxidized with the appropriate oxidizing agent in a compatible solvent at a suitable temperature to yield the 2'-methyl sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, MnO₂, ruthenium tetroxide, phase transfer catalysts such as chromic acid or permanganate supported on a polymer, Cl₂-pyridine, H₂O₂-ammonium molybdate, NaBrO₂-CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as taught by Greene et al. *Protective Groups in Organic Synthesis*. John Wiley and Sons, Second Edition, 1991.

The synthesis of a 2'-methyl-cytidine nucleoside is shown in Scheme 7.

Scheme 7

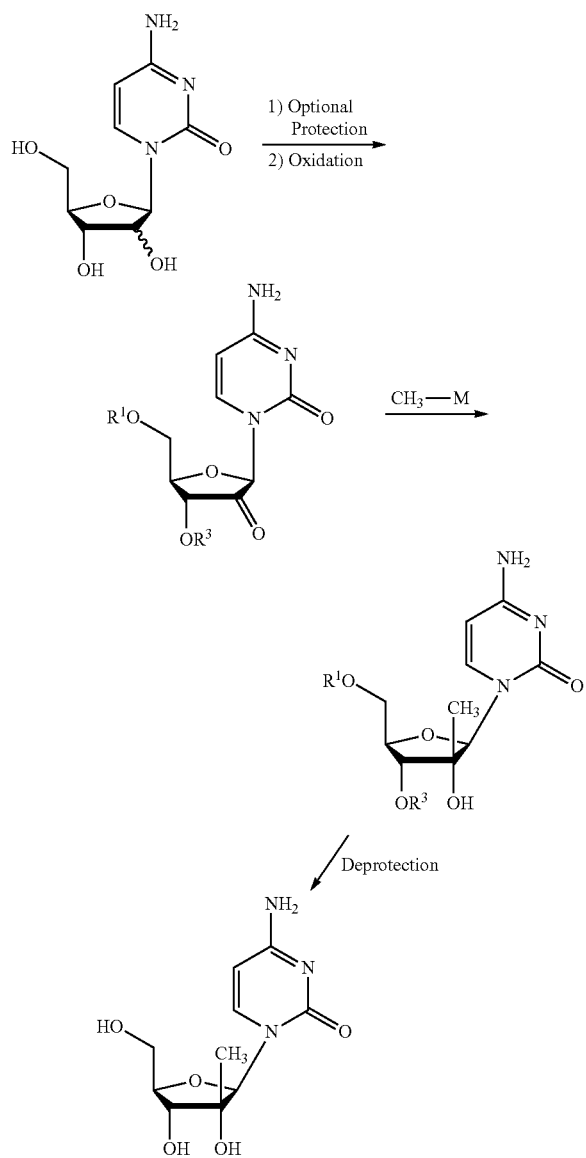

wherein:
$R^1$ and $R^3$ are independently H, phosphate (including mono-, di- or triphosphate and a stabilized phosphate prodrug); acyl (including lower acyl); alkyl (including lower alkyl); sulfonate ester (including alkyl or arylalkyl sulfonyl including methanesulfonyl); benzyl, wherein the phenyl group is optionally substituted with one or more substituents as described in the definition of aryl given herein; lipid (including a phospholipid); amino acid; carbohydrate; peptide; cholesterol; or a pharmaceutically acceptable leaving group that provides a compound wherein $R^1$ or $R^3$ is independently H or phosphate when administered in vivo.

Pharmaceutically Acceptable Prodrugs

The term "pharmaceutically acceptable prodrug and/or salt" is used throughout the specification to describe any pharmaceutically acceptable form (such as an ester, phosphate ester, salt of an ester or a related group) of a nucleoside compound which, upon administration to a patient, provides the parent nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against a Flaviviridae, or are metabolized to a compound that exhibits such activity.

2'-Branched nucleosides, including 2'-branched pyrimidine nucleoside, such as β-D-2'-$CH_3$-riboC, or related compounds administered as acylated or nucleoside prodrugs can be used in combination or alternation therapy.

Any of the nucleosides described herein or other compounds that contain a hydroxyl or amine function can be administered as a nucleoside prodrug to increase the activity, bioavailability, stability or otherwise alter the properties of the nucleoside. A number of nucleoside prodrug ligands are known. In general, alkylation, acylation or other lipophilic modification of the hydroxyl group of the compound or of the mono, di or triphosphate of the nucleoside will increase the stability of the nucleoside. Examples of substituent groups that can replace one or more hydrogens on the phosphate moiety or hydroxyl are alkyl, aryl, steroids, carbohydrates, including sugars, 1,2-diacylglycerol and alcohols. Many are described in R. Jones and N. Bischofberger, *Antiviral Research*, 27 (1995) 1-17. Any of these can be used in combination with the disclosed nucleosides or other compounds to achieve a desire effect The active nucleoside or other hydroxyl containing compound can also be provided as an ether lipid (and particularly a 5'-ether lipid for a nucleoside), as disclosed in the following references: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses*. 6:491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3-deoxythymidine." *Antimicrob. Agents Chemother.* 36:2025.2029; Hostetier, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127. Nonlimiting examples of U.S. patents that disclose suitable lipophilic substituents that can be covalently incorporated into the nucleoside or other hydroxyl or amine containing compound, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

2', 3' and 5'-Prodrugs of 2'-branched β-D nucleosides, or their pharmaceutically acceptable salts or pharmaceutically acceptable formulations containing these compounds can be used to treat Flaviviridae infections. Specifically, the 3'-valine ester prodrug of β-D-2'-CH₃-riboC represented by the formula:

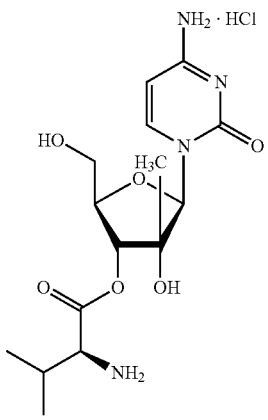

or its pharmaceutically acceptable salt, can be administered to a subject for the treatment of a Flaviviridae infection.

In one embodiment, 2'-branched β-D nucleoside 2'-prodrug includes biologically cleavable moieties at the 2' and/or 5' positions. Preferred moieties are natural or synthetic D or L amino acid esters, including D or L-valyl, though preferably L-amino acid esters, such as L-valyl, and alkyl esters including acetyl. Therefore, this invention specifically includes 2'-D or L-amino acid ester and 2',5'-D or L-diamino acid ester, preferably L-amino acid ester, of 2'-branched β-D or β-L nucleosides with any desired purine or pyrimidine base, wherein the parent drug optionally has an $EC_{50}$ of less than 15 micromolar, and even more preferably less than 10 micromolar; 2'-(alkyl or aryl) ester or 2',5'-di(alkyl or aryl) ester of 2'-branched β-D or β-L nucleosides with any desired purine or pyrimidine base, wherein the parent drug optionally has an $EC_{50}$ of less than 10 or 15 micromolar; and prodrugs of 2',5'-diesters of 2'-branched β-D or β-L nucleosides wherein (i) the 2' ester is a natural or synthetic D or L-amino acid ester, though preferably an L-amino acid ester, and the 5'-ester is an alkyl or aryl ester; (ii) both esters are independently natural or synthetic D or L-amino acid ester, though preferably both are L-amino acid esters; (iii) both esters are independently alkyl or aryl esters; and (iv) the 2' ester is independently an alkyl or aryl ester and the 5'-ester is a natural or synthetic D or L-amino acid ester, though preferably an L-amino acid ester, wherein the parent drug optionally has an $EC_{50}$ of less than 10 or 15 micromolar.

Examples of prodrugs falling within the invention are 2'-D or L-valine ester of β-D-2'-methyl-cytidine; β-D-2',6-dimethyl-cytidine; 2'-L-valine ester of β-D-2',6-dimethyl-thymidine; 2'-L-valine ester of β-D-2',8-dimethyl-adenosine; 2'-L-valine ester of β-D-2',8-dimethyl-guanosine; 2'-L-valine ester of β-D-2',6-dimethyl-5-fluorocytidine; 2'-L-valine ester of β-D-2',6-dimethyl-uridine; 2'-acetyl ester of β-D-2',6-dimethyl-cytidine; 2'-acetyl ester of β-D-2',6-dimethyl-thymidine; 2'-acetyl ester of β-D-2',8-dimethyl-adenosine; 2'-acetyl ester of β-D-2',8-dimethyl-guanosine; 2'-acetyl ester of β-D-2',6-dimethyl-5-fluoro-cytidine; and 2'-esters of β-D-2',6-dimethyl-(cytidine, 5-fluorocytidine, uridine or thymidine) or 2'-esters of β-D-2'-methyl-cytidine or β-D-2',8-dimethyl-(guanosine, adenosine or inosine) wherein (i) the 2' ester is an amino acid ester; or (ii) the 2' ester is an alkyl or aryl ester.

Additional examples of prodrugs falling within the invention are 2',5'-L-divaline ester of β-D-2'-methyl cytidine; β-D-2',6-dimethyl-cytidine (dival-2',6-diMe-L-dC); 2',5'-L-divaline ester of β-D-2',6-dimethyl-thymidine; 2',5'-L-divaline ester of β-D-2',8-dimethyl-adenosine; 2',5'-L-divaline ester of β-D-2',8-dimethyl-guanosine; 2',5'-L-divaline ester of β-D-2',6-dimethyl-5-fluoro-cytidine; 2',5'-L-divaline ester of β-D-2',6-dimethyl-uridine; 2',5'-diacetyl ester of β-D-2',6-dimethyl-cytidine; 2',5'-diacetyl ester of β-D-2',6-dimethyl-thymidine; 2',5'-diacetyl ester of β-D-2',8-dimethyl-adenosine; 2',5'-diacetyl ester of β-D-2',8-dimethyl-guanosine; 2',5'-diacetyl ester of β-D-2',6-dimethyl-5-fluoro-cytidine; and 2',5'-diesters of β-D-2',6-dimethyl-(cytidine, 5-fluoro-cytidine, uridine or thymidine) or 2',5'-diesters of β-D-2'-methyl cytidine or β-D-2',8-dimethyl-(guanosine, adenosine or inosine) wherein (i) the 2' ester is an amino acid ester and the 5'-ester is an alkyl or aryl ester; (ii) both esters are amino acid esters; (iii) both esters are independently alkyl or aryl esters; or (iv) the 2' ester is an alkyl or aryl ester and the 5'-ester is an amino acid ester.

In another embodiment, the 2'-branched β-D nucleoside 3'-prodrug includes biologically cleavable moieties at the 3' and/or 5' positions. Preferred moieties are natural or synthetic β-D or β-L amino acid esters, such as valyl, though preferably L-amino acids, such as L-valyl, and alkyl esters including acetyl. Therefore, this invention specifically includes 3'-L-amino acid ester and 3',5'-L-diamino acid ester of a 2'-branched β-D or β-L nucleosides with any desired purine or pyrimidine base, wherein the parent drug optionally has an $EC_{50}$ of less than 15 micromolar, and even more preferably less than 10 micromolar; 3'-(alkyl or aryl) ester or 3',5'-L-di(alkyl or aryl) ester of 2'-branched β-D or β-L nucleosides with any desired purine or pyrimidine base, wherein the parent drug optionally has an $EC_{50}$ of less than 10 or 15 micromolar; and prodrugs of 3',5'-diesters of 2'-branched β-D or β-L nucleosides wherein (i) the 3' ester is a natural or synthetic D or L amino acid ester and the 5'-ester is an alkyl or aryl ester; (ii) both esters are natural or synthetic D or L-amino acid esters; (iii) both esters are independently alkyl or aryl esters; and (iv) the 3' ester is independently an alkyl or aryl ester and the 5'-ester is a natural or synthetic D or L-amino acid ester, wherein the parent drug optionally has an EC50 of less than 10 or 15 micromolar.

Examples of prodrugs falling within the invention are 3'-L-valine ester of β-D-2'-methyl-cytidine; β-D-2',6-dimethyl-cytidine; 3'-L-valine ester of β-D-2',6-dimethyl-thymidine; 3'-L-valine ester of β-D-2',8-dimethyl-adenosine;

3'-L-valine ester of β-D-2',8-dimethyl-guanosine; 3'-L-valine ester of β-D-2',6-dimethyl-5-fluorocytidine; 3'-L-valine ester of β-D-2',6-dimethyl-uridine; 3'-acetyl ester of β-D-2',6-dimethyl-cytidine; 3'-acetyl ester of β-D-2',6-dimethyl-thymidine; 3'-acetyl ester of β-D-2',8-dimethyl-adenosine; 3'-acetyl ester of β-D-2',8-dimethyl-guanosine; 3'-acetyl ester of β-D-2'-methyl-cytidine; 3'-acetyl ester of β-D-2',6-dimethyl-5-fluoro-cytidine; and 3'-esters of β-D-2',6-dimethyl-(cytidine, 5-fluorocytidine, uridine or thymidine) or 3'-esters of β-D-2',8-dimethyl-(guanosine, adenosine or inosine) wherein (i) the 3' ester is an amino acid ester; or (ii) the 3' ester is an alkyl or aryl ester.

Additional examples of prodrugs falling within the invention are 3',5'-L-divaline ester of β-D-2'-methyl-cytidine; β-D-2',6-dimethyl-cytidine (dival-2',6-diMe-L-dC); 3',5'-L-divaline ester of β-D-2',6-dimethyl-thymidine; 3',5'-L-divaline ester of β-D-2',8-dimethyl-adenosine; 3',5'-L-divaline ester of β-D-2',8-dimethyl-guanosine; 3',5'-L-divaline ester of β-D-2',6-dimethyl-5-fluoro-cytidine; 3',5'-L-divaline ester of β-D-2',6-dimethyl-uridine; 3',5'-diacetyl ester of β-D-2',6-dimethyl-cytidine; 3',5'-diacetyl ester of β-D-2',6-dimethyl-thymidine; 3',5'-diacetyl ester of β-D-2',8-dimethyl-adenosine; 3',5'-diacetyl ester of β-D-2',8-dimethyl-guanosine; 3',5'-diacetyl ester of β-D-2',6-dimethyl-5-fluoro-cytidine; and 3',5'-diesters of β-D-2',6-dimethyl-(cytidine, 5-fluoro-cytidine, or β-D-2'-methyl-cytidine, uridine or thymidine) or 3',5'-diesters of β-D-2',8-dimethyl-(guanosine, adenosine or inosine) wherein (i) the 3' ester is an amino acid ester and the 5'-ester is an alkyl or aryl ester; (ii) both esters are amino acid esters; (iii) both esters are independently alkyl or aryl esters; or (iv) the 3' ester is an alkyl or aryl ester and the 5'-ester is an amino acid ester.

In another embodiment, the prodrug of 2'-branched β-D nucleoside includes biologically cleavable moieties at the 2', 3' and/or 5' positions. Preferred moieties are natural or synthetic D or L amino acid esters, including D or L-valyl, though preferably L-amino acid esters, such as L-valyl, and alkyl esters including acetyl. Therefore, this invention specifically includes 2',3'-L or D-diamino acid ester and 2',3', 5'-L or D-triamino acid ester of 2'-branched β-D or β-L nucleosides, preferably L-amino acid, with any desired purine or pyrimidine base, wherein the parent drug optionally has an $EC_{50}$ of less than 15 micromolar, and even more preferably less than 10 micromolar; 2',3'-di(alkyl or aryl) ester or 2',3',5'-L-tri(alkyl or aryl) ester of 2'-branched β-D or β-L nucleosides with any desired purine or pyrimidine base, wherein the parent drug optionally has an $EC_{50}$ of less than 10 or 15 micromolar; and prodrugs of 2',3'-diesters of 2'-branched β-D or β-L nucleosides wherein (i) the 2' ester is an amino acid ester and the 3'-ester is an alkyl or aryl ester; (ii) both esters are amino acid esters; (iii) both esters are independently alkyl or aryl esters; and (iv) the 2' ester is independently an alkyl or aryl ester and the 3'-ester is an amino acid ester, wherein the parent drug optionally has an $EC_{50}$ of less than 10 or 15 micromolar. Further, 2',3',5'-triesters of 2'-branched β-D or β-L nucleosides wherein (i) all three esters are amino acid esters; (ii) all three esters are independently alkyl or aryl esters; (iii) the 2' ester is an amino acid ester, the 3' ester is an amino acid ester and the 5'-ester is an alkyl or aryl ester; (iv) the 2' ester is an amino acid ester, the 3' ester is an alkyl or aryl ester and the 5'-ester is an alkyl or aryl ester; (v) the 2' ester is an alkyl or aryl ester, the 3' ester is an alkyl or aryl ester and the 5'-ester is an amino acid ester; (vi) the 2' ester is an alkyl or aryl ester, the 3' ester is an amino acid ester and the 5'-ester is an amino acid ester; (vii) the 2' ester is an alkyl or aryl ester, the 3' ester is an amino acid ester and the 5'-ester is an alkyl or aryl ester; and (viii) the 2' ester is an amino acid ester, the 3' ester is an alkyl or aryl ester and the 5'-ester is an amino acid ester; wherein the parent drug optionally has an $EC_{50}$ of less than 10 or 15 micromolar.

Examples of prodrugs falling within the invention include 2',3'-L-divaline ester of β-D-2'-methyl-cytidine; β-D-2',6-dimethyl-cytidine (dival-2',6-diMe-L-dC); 2',3'-L-divaline ester of β-D-2',6-dimethyl-thymidine; 2',3'-L-divaline ester of β-D-2',8-dimethyl-adenosine; 2',3'-L-divaline ester of β-D-2',8-dimethyl-guanosine; 2',3'-L-divaline ester of β-D-2',6-dimethyl-5-fluoro-cytidine; 2',3'-L-divaline ester of β-D-2',6-dimethyl-uridine; 2',3'-diacetyl ester of β-D-2',6-dimethyl-cytidine; 2',3'-diacetyl ester of β-D-2',6-dimethyl-thymidine; 2',3'-diacetyl ester of β-D-2',8-dimethyl-adenosine; 2',3'-diacetyl of β-D-2'-methyl-cytidine; 2',3'-diacetyl ester of β-D-2',8-dimethyl-guanosine; 2',3'-diacetyl ester of β-D-2',6-dimethyl-5-fluoro-cytidine; and 2',3'-diesters of β-D-2',6-dimethyl-(cytidine, 5-fluorocytidine, uridine or thymidine) or 2',3'-diesters of β-D-2',8-dimethyl-(guanosine, adenosine or inosine) wherein (i) the 2' ester is an amino acid ester and the 3'-ester is an alkyl or aryl ester; (ii) both esters are amino acid esters; (iii) both esters are independently alkyl or aryl esters; or (iv) the 2' ester is an alkyl or aryl ester and the 3'-ester is an amino acid ester.

Additional examples of prodrugs falling within the invention include 2',3',5'-L-trivaline ester of β-D-2'-methyl-cytidine; β-D-2',6-dimethyl-cytidine (trival-2',6-diMe-L-dC); 2',3',5'-L-trivaline ester of β-D-2',6-dimethyl-thymidine; 2',3',5'-L-trivaline ester of β-D-2',8-dimethyl-adenosine; 2',3',5'-L-trivaline ester of β-D-2',8-dimethyl-guanosine; 2',3',5'-L-trivaline ester of β-D-2',6-dimethyl-5-fluoro-cytidine; 2',3',5'-L-trivaline ester of β-D-2', 6-dimethyl-uridine; 2',3',5'-triacetyl ester of β-D-2',6-dimethyl-cytidine; 2',3',5'-triacetyl ester of β-D-2',6-dimethyl-thymidine; 2',3',5'-triacetyl ester of β-D-2',8-dimethyl-adenosine; 2',3',5'-triacetyl ester of β-D-2',8-dimethyl-guanosine; 2',3',5'-triacetyl ester of β-D-2',6-dimethyl-5-fluoro-cytidine; and 2',3',5'-triesters of β-D-2',6-dimethyl-(cytidine, 5-fluorocytidine, uridine or thymidine) and 2',3',5'-triesters of β-D-2',8-dimethyl-(guanosine, adenosine or inosine) wherein (i) all three esters are amino acid esters; (ii) all three esters are independently alkyl or aryl esters; (iii) the 2' ester is an amino acid ester, the 3' ester is an amino acid ester and the 5'-ester is an alkyl or aryl ester; (iv) the 2' ester is an amino acid ester, the 3' ester is an alkyl or aryl ester and the 5'-ester is an alkyl or aryl ester; (v) the 2' ester is an alkyl or aryl ester, the 3' ester is an alkyl or aryl ester and the 5'-ester is an amino acid ester; (vi) the 2' ester is an alkyl or aryl ester, the 3' ester is an amino acid ester and the 5'-ester is an amino acid ester; (vii) the 2' ester is an alkyl or aryl ester, the 3' ester is an amino acid ester and the 5'-ester is an alkyl or aryl ester; and (viii) the 2' ester is an amino acid ester, the 3' ester is an alkyl or aryl ester and the 5'-ester is an amino acid ester.

Further examples of prodrugs falling within the invention include prodrugs disclosed in U.S. Pat. Nos. 6,284,748 and 6,312,662. In particular, the prodrugs of the present invention include compounds of the structure

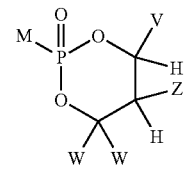

wherein:

V, W and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3-5 atoms to form a cyclic group containing 5-7 atoms, optionally 1 heteroatom, substituted with hydroxy, acyloxy, alkoxycarbonyloxy, or aryloxycarbonyloxy attached to a carbon atom that is three atoms from both O groups attached to the phosphorus; or together V and Z are connected via an additional 3-5 atoms to form a cyclic group, optionally containing 1 heteroatom, that is fused to an aryl group at the beta and gamma position to the O attached to the phosphorus; or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from an O attached to the phosphorus;

together Z and W are connected via an additional 3-5 atoms to form a cyclic group, optionally containing one heteroatom, and V must be aryl, substituted aryl, heteroaryl, or substituted heteroaryl;

together W and W' are connected via an additional 2-5 atoms to form a cyclic group, optionally containing 0-2 heteroatoms, and V must be aryl, substituted aryl, heteroaryl, or heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{12}$, and —(CH$_2$)$_p$-SR$^{12}$;

p is an integer 2 or 3;

R$^2$ is selected from the group consisting of R.sup.3 and —H;

R$^3$ is selected from the group consisting of alkyl, aryl, alicyclic, and aralkyl;

R$^{12}$ is selected from the group consisting of —H, and lower acyl;

M is selected from the group that attached to PO$_3$$^{2-}$, P$_2$O$_6$$^{3-}$ or P$_3$O$_9$$^{4-}$ is a the 2'-branched nucleoside, and is attached to the phosphorus via a carbon, oxygen, sulfur or nitrogen atom.

In one non-limiting example, the prodrug is attached to the nucleoside as in the following compounds

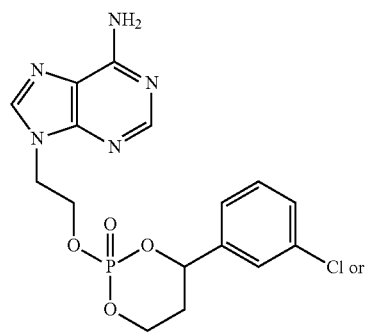

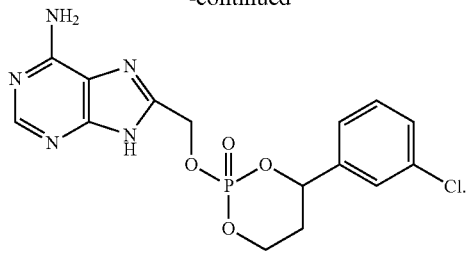

General Synthesis of 2' and/or 3'-Prodrugs

The key starting material for this process is an appropriately substituted 2'-branched β-D nucleosides. The branched nucleoside can be purchased or can be prepared by any known means including the techniques disclosed herein. The branched nucleoside can be optionally protected with a suitable protecting group, preferably with a silyl group, by methods well known to those skilled in the art, as taught by Greene et al. *Protective Groups in Organic Synthesis*, John Wiley and Sons, Second Edition, 1991. The protected branched nucleoside can then be coupled with a suitable acyl doner, such as an acyl chloride and/or an acyl anhydride with the appropriate protic or aprotic solvent at a suitable temperature, to give the 2' and/or 3' prodrug of 2'-branched β-D nucleoside. Alternatively, the protected branched nucleoside can then be coupled with a suitable acyl, such as a carboxylic acid, such as alkanoic acid and/or amino acid residue, optionally with a suitable coupling agent, with the appropriate aprotic solvent at a suitable temperature, to give the 2' and/or 3' prodrug of 2'-branched β-D nucleoside. Possible coupling reagents are any reagents that promote coupling, including but are not limiting to, Mitsunobu reagents (e.g. diisopropyl azodicarboxylate and diethyl azodicarboxylate) with triphenylphosphine or various carbodiimides.

For example, simple amino-alcohols can be esterified using acid chlorides in refluxing acetonitrile-benzene mixture (See Scheme 8 below: *Synthetic Communications*, 1978, 8(5), 327-333; hereby incorporated by reference). Alternatively, esterification can be achieved using an anhydride, as described in *J. Am. Chem. Soc.*, 1999, 121(24), 5661-5664.

Scheme 8

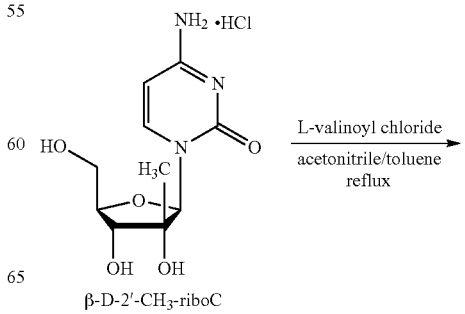

β-D-2'-CH$_3$-riboC

-continued

3'-valine ester of β-D-2'-CH₃-riboC

III. Detection of the β-D-2'-CH₃-riboC Induced Mutation in a Flaviviridae Genome In one embodiment, a method is provided for treating a patient infected with Flaviviridae comprising:
 (i) administering an effective amount of (β-D-2'-CH₃-riboC or a prodrug, such as the 3' valine ester prodrug of β-D-2'-CH₃-riboC, or a pharmaceutically acceptable salt thereof;
 (ii) identifying viral resistance to β-D-2'-CH₃-riboC in the patient;
 (iii) administering an effective amount of one or more drugs that in combination and/or alternation with one or more drugs that directly or indirectly induce a mutation in a Flaviviridae at a location other than a mutation of a nucleotide that results in a change from serine to a different amino acid in the highly conserved consensus sequence, XRXSGXXXT (SEQ ID NO: 63), of domain B of the RNA polymerase region, and/or one or more drugs that are associated with such a mutation.

In another embodiment, a method is provided for treating a patient infected with HCV comprising:
 (i) administering an effective amount of β-D-2'-CH₃-riboC or a prodrug, such as the 3' valine ester prodrug of β-D-2'-CH₃-riboC, or a pharmaceutically acceptable salt thereof;
 (ii) identifying viral resistance to β-D-2'-CH₃-riboC in the patient;
 (iii) administering an effective amount of one or more drugs that directly or indirectly induce a mutation in a Flaviviridae at a location other than a mutation of a nucleotide that results in a change from serine at position 282 to a different amino acid, such as threonine, in the highly conserved consensus sequence, XRXSGXXXT (SEQ ID NO: 63), of domain B of the RNA polymerase region, and/or one or more drugs that is associated with such a mutation.

In one embodiment, a method is provided for treating a host infected with BVDV comprising:
 (i) administering an effective amount of β-D-2'-CH₃-riboC or a prodrug, such as the 3' valine ester prodrug of β-D-2'-CH₃-riboC, or a pharmaceutically acceptable salt thereof;
 (ii) identifying viral resistance to β-D-2'-CH₃-riboC in the host;
 (iii) administering an effective amount of one or more drugs that directly or indirectly induce a mutation in a Flaviviridae at a location other than a mutation of a nucleotide that results in a change from serine at position 405 to a different amino acid, such as threonine, in the highly conserved consensus sequence, XRXSGXXXT (SEQ ID NO: 63), of domain B of the RNA polymerase region, and/or one or more drugs that is associated with such a mutation.

In another embodiment, the invention provides a method for treating a patient infected with Flaviviridae comprising:
 (i) administering an effective amount of β-D-2'-CH₃-riboC or a prodrug, such as the 3' valine ester prodrug of β-D-2'-CH₃-riboC, or a pharmaceutically acceptable salt thereof;
 (ii) identifying viral resistance to β-D-2'-CH₃-riboC in the patient;
 (iii) administering an effective amount of interferon.

In certain embodiments, identification of viral resistance to β-D-2'-CH₃-riboC in the patient can be determined by a phenotypic analysis of viral plaque growth. In another embodiment, identification of viral resistance to β-D-2'-CH₃-riboC in the patient can be determined by the replication fitness of the virus. In a further embodiment, identification of viral resistance to β-D-2'-CH₃-riboC in the patient can be determined by detecting the presence of cytidine at nucleotide 1214 of the RNA polymerase region of BVDV or cytidine at nucleotide 8443 of HCV.

In one embodiment, the present invention includes a method for treating a patient infected with Flaviviridae comprising:
 (i) administering an effective amount of β-D-2'-CH₃-riboC or a prodrug, such as the 3' valine ester prodrug of β-D-2'-CH₃-riboC, or a pharmaceutically acceptable salt thereof;
 (ii) obtaining a viral culture sample from the patient;
 (iii) culturing the sample and comparing the plaque growth between the sample and wild type virus;
 (iv) determining whether the plaque growth of the sample is smaller than the plaque growth of the wildtype, which indicates resistance to β-D-2'-CH₃-riboC;
 (v) administering an effective amount of interferon to those patients that are resistant to β-D-2'-CH₃-riboC.

In another embodiment, the invention provides a method for treating a patient infected with Flaviviridae comprising:
 (i) administering an effective amount of β-D-2'-CH₃-riboC or a prodrug, such as the 3' valine ester prodrug of β-D-2'-CH₃-riboC, or a pharmaceutically acceptable salt thereof;
 (ii) obtaining a viral sample from the patient;
 (iii) determining the replication fitness of the viral;
 (iv) determining whether the replication fitness of the sample is less than the replication fitness of the wildtype virus, which indicates resistance to β-D-2'-CH₃-riboC;
 (v) administering an effective amount of interferon to those patients that are resistant to β-D-2'-CH₃-riboC.

In one embodiment, viral plaque growth and/or viral replication fitness can be quantitated by a viral plaque assay. In other embodiments, other assays, such as the infectious center assay, virus-inducible reporter assay, transformation assay, end point dilution assay, or RT-PCR technology can be used to quantitate viral titers (Flint et al. Principles of Virology (ASM) Chapter 2; Wagner & Hewlett. Basic Virology (Blackwell), Chapters 9 & 10).

A plaque assay can be conducted to quantitate viral plaque growth and/or replication fitness. A dilute solution of the virus can be applied to a culture dish that contains a monolayer of host cells. The cells can be overlayed with a semisolid layer (such as a viscous medium, for example, agar) to prevent virus diffusion from one infected cell to another. After incubation the 'plaques' can be recognized, and the number of infective virus particles in the original suspension estimated. One method to recognize the plaques is through the use of antibody staining methods to detect viral antigens within infected cells in the monolayer. These infected cells can then be visualized using a chromagen or a fluorescent label on the virus-specific antibody. The plaques can be observed for phenotypic analysis and/or counted to determine viral titers. Virus titers can be calculated in focus forming units (FFU)/mL, using the following equation: $T_{FFU/mL}=N \times 5 \times D$; where T is a virus titer in FFU/mL; N is a number of plaques per well; and D is a dilution factor for the corresponding virus sample. (For example, if 12 plaques were found in a well corresponding to $10^{-5}$ dilution of virus sample, than $T=12 \times 5 \times 10^5 = 6 \times 10^6$ FFU/mL) and viral replication fitness, which is the overall replicative ability to produce infected progeny in a defined host environment, can then be determined.

Another aspect of the invention is a method for detecting the presence of the nucleotide 1214 G to C mutation of the RNA polymerase region of BVDV (causing a mutation from Serine to Threonine at amino acid 405). Since it is recognized that $Ser_{405}$, the amino acid position of the BVDV putative functional NS5B domain B, is highly conserved among all hepaci-, pesti- and flavivirus genomes (FIG. 11; Lai et al. *J Virol.*, 1999, 73, 10129-36), the corresponding serine residues of the putative functional NS5B domain B of other Flaviviridaes that are mutated can be detected according to the embodiments of the present invention. For example, $Ser_{405}$ of the RNA polymerase domain of BVDV corresponds to $Ser_{282}$ of the RNA polymerase domain of HCV.

Therefore, the embodiments of the present invention also encompass a G to C mutation of nucleotide 8443 of the HCV genome (which corresponds to nucleotide 1214 of the BVDV RNA polymerase region).

In one embodiment, the invention provides a process for detecting a mutation that indicates β-D-2'-CH$_3$-riboC resistance, which includes contacting a sample containing a Flaviviridae nucleic acid sequence with an oligonucleotide probe having a sequence complementary to a section of the Flaviviridae genome that includes the mutation; and then determining if the oligonucleotide hybridizes to the viral nucleic acid.

In other embodiments, the invention provides a method for treating a patient infected with Flaviviridae comprising:
(i) administering an effective amount of β-D-2'-CH$_3$-riboC or a prodrug, such as the 3' valine ester prodrug of β-D-2'-CH$_3$-riboC, or a pharmaceutically acceptable salt thereof;
(ii) assaying the blood of the patient to test for seroconversion from wildtype to mutant virus;
(iii) administering an effective amount of interferon.

In yet another embodiment, the invention provides a method for assaying a sample suspected of containing a β-D-2'-CH$_3$-riboC-resistant Flaviviridae comprising:
(i) contacting a sample containing a Flaviviridae nucleic acid sequence with a detectable oligonucleotide probe having a sequence complementary to the cytidine at nucleotide 1214 of the RNA polymerase region of BVDV or nucleotide 8443 of the HCV genome;
(ii) allowing the probe to hybridize to the sequence;
(iii) detecting the hybridization of the probe to cytidine at nucleotide 1214 of the RNA polymerase region of BVDV or nucleotide 8443 of the HCV genome.

In a further embodiment, the invention provides a method for assaying a sample suspected of containing a Thr instead of a Ser in the highly conserved consensus sequence, XRX SGXXXT (SEQ ID NO: 63), of domain B of the RNA polymerase region of a Flaviviridae, which indicates that the virus is hypersensitive to interferon treatment, comprising:
(i) contacting a sample suspected of containing a Flaviviridae nucleic acid sequence with a detectable oligonucleotide probe having a sequence complementary a codon that encodes Thr in the position of Ser in the conserved consensus sequence, XRXSGXXXT (SEQ ID NO: 63), of domain B of the RNA polymerase region of a Flaviviridae;
(ii) allowing the probe to hybridize to the sequence;
(iii) detecting the hybridization of the probe to the sequence.

In another embodiment, the invention provides a method for assaying a sample suspected of containing a Thr instead of a Ser at amino acid position 405 or a cytidine at nucleotide 1214 of the RNA polymerase region of BVDV, which indicates that the virus is hypersensitive to interferon treatment, comprising:
(i) contacting a sample suspected of containing a BVDV nucleic acid sequence with a detectable oligonucleotide probe having a sequence complementary to the cytidine at nucleotide 1214 of the RNA polymerase region;
(ii) allowing the probe to hybridize to the sequence;
(iii) detecting the hybridization of the probe to cytidine at nucleotide 1214 of the RNA polymerase region of BVDV.

In another embodiment, the invention provides a method for assaying a sample suspected of containing a Thr instead of a Ser in the highly conserved consensus sequence, XRX SGXXXT (SEQ ID NO: 63), of domain B of the RNA polymerase region at the highly conserved at amino acid position 282 or a cytidine at nucleotide 8433 of the HCV genome, which indicates that the virus is hypersensitive to interferon treatment, comprising:
(i) contacting a sample suspected of containing a HCV nucleic acid sequence with a detectable oligonucleotide probe having a sequence complementary to the cytidine at nucleotide 8443;
(ii) allowing the probe to hybridize to the sequence;
(iii) detecting the hybridization of the probe to cytidine at nucleotide 8443 of the HCV genome.

Oligonucleotide Probes

Oligonucleotide probes are provided that are capable of detecting the presence of a 2'-branched pyrimidine nucleoside-induced mutation of Flaviviridae. The probes are complementary to sequences of viral nucleic acids that include the mutation. These probes can be used in processes and kits. The oligonucleotide probes can detect the nucleotide cytidine at nucleotide 1214 of the RNA polymerase region of BVDV or at nucleotide 8443 of the RNA polymerase region of HCV, or other nucleotides of Flaviviridae that encode the conserved serine of the domain B of RNA polymerase within a Flaviviridae genome (FIG. 11).

The oligonucleotide probes are preferably at least 14 nucleotides in length, and in a preferred embodiment, are at least 15, 20, 25 or 30 nucleotides in length. It is generally not preferred to use a probe that is greater than approximately 25 or 30 nucleotides in length. In one embodiment, the oligonucleotide probe can be designed to identify the guanine to cytidine base change at nucleotide 1214 of the RNA polymerase region of a BVDV. In another embodiment, the oligonucleotide probe can be designed to identify the guanine to cytidine base change at nucleotide 8443 of HCV. The oligonucleotide probe can be designed such that the mutated region is located in the interior section of the hybridized segment, or alternatively can be on either the 3' or 5' end of the hybridized segment. It is preferred that the mutated region be located near the middle of the probe to allow efficient hybridization.

Table 2 below provides illustrative embodiments of BVDV nucleotide sequences that include nucleotide position 1214 of the RNA polymerase region, alternatively referred to as nucleotide position 11,136 (see Genebank accession number AJ133739; Vassilev and Donis (2000) Virus Res 69(2) 95-107). Given these sequences, one of ordinary skill using standard algorithms can construct oligonucleotide probes that are complementary or substantially complementary to the nucleotide sequences below. The rules for complementary pairing are well known: cytidine ("C") always pairs with guanine ("G") and thymine ("T") or uracil ("U") always pairs with adenine ("A"). It is recognized that it is not necessary for the probe to be 100% complementary to the target nucleic acid sequence, as long as the probe sufficiently hybridizes and can recognize the diagnostic nucleotide. A certain degree of base pair mismatch can generally be tolerated.

drug and/or salt, to a human in need of therapy, in combination and/or alternation with one or more drugs that directly or indirectly induce a mutation in a Flaviviridae at a location other than a mutation of a nucleotide that results in a change from serine to a threonine in the highly conserved consensus sequence, XRXSGXXXT (SEQ ID NO: 63), of domain B of the RNA polymerase region, and/or one or more drugs that is associated with such mutation. The codons ACA, ACG or ACU, which also encode Threonine, can be substituted for the codon ACC (in bold) in Table 2 above to detect the presence of a Threonine in domain B of the RNA polymerase region of BVDV.

Another aspect of the present invention provides a method to treat and/or to substantially cure a Flaviviridae infection in a host infected with a Flaviviridae that contains a Serine to Threonine mutation in the highly conserved consensus sequence, XRXSGXXXT (SEQ ID NO: 63), of domain B of the RNA polymerase region by administering a therapeutically effective amount of interferon. Therefore, in other embodiments of the present invention, the codons ACA, ACG or ACU, which also encode Threonine, can be substituted for the codon ACC (in bold) in Table 2 above, for

TABLE 2

Nonlimiting examples of nucleic acid sequences with a single point mutation at nucleotide 1214 (also referred to as position 11,136: see Genebank accession number AJ133739; Vassilev and Donis, *Virus Res* 2000, 69(2), 95-107) of the RNA polymerase region of BVDV

| | AGG | | 405 S | |
|---|---|---|---|---|
| AAGTATATATAAGAAATGGGCAGAGAGGG | ACC | GGCCAGCCAGACACAAGTGCTGGCAACAG. | 405 T | |
| | | | (Seq. ID No. 1) | |
| AAGTATATATAAGAAATGGGCAGAGAGGG | ACC | . | (Seq. ID No. 2) | |
| AGTATATATAAGAAATGGGCAGAGAGGG | ACC | G. | (Seq. ID No. 3) | |
| GTATATATAAGAAATGGGCAGAGAGGG | ACC | GG. | (Seq. ID No. 4) | |
| TATATATAAGAAATGGGCAGAGAGGG | ACC | GGC. | (Seq. ID No. 5) | |
| ATATATAAGAAATGGGCAGAGAGGG | ACC | GGCC. | (Seq. ID No. 6) | |
| TATATAAGAAATGGGCAGAGAGGG | ACC | GGCCA. | (Seq. ID No. 7) | |
| ATATAAGAAATGGGCAGAGAGGG | ACC | GGCCAG. | (Seq. ID No. 8) | |
| TATAAGAAATGGGCAGAGAGGG | ACC | GGCCAGC. | (Seq. ID No. 9) | |
| ATAAGAAATGGGCAGAGAGGG | ACC | GGCCAGCC. | (Seq. ID No. 10) | |
| TAAGAAATGGGCAGAGAGGG | ACC | GGCCAGCCA. | (Seq. ID No. 11) | |
| AAGAAATGGGCAGAGAGGG | ACC | GGCCAGCCAG. | (Seq. ID No. 12) | |
| AGAAATGGGCAGAGAGGG | ACC | GGCCAGCCAGA. | (Seq. ID No. 13) | |
| GAAATGGGCAGAGAGGG | ACC | GGCCAGCCAGAC. | (Seq. ID No. 14) | |
| AAATGGGCAGAGAGGG | ACC | GGCCAGCCAGACA. | (Seq. ID No. 15) | |
| AATGGGCAGAGAGGG | ACC | GGCCAGCCAGACAC. | (Seq. ID No. 16) | |
| ATGGGCAGAGAGGG | ACC | GGCCAGCCAGACACA. | (Seq. ID No. 17) | |
| TGGGCAGAGAGGG | ACC | GGCCAGCCAGACACAA. | (Seq. ID No. 18) | |
| GGGCAGAGAGGG | ACC | GGCCAGCCAGACACAAG. | (Seq. ID No. 19) | |
| GGCAGAGAGGG | ACC | GGCCAGCCAGACACAAGT. | (Seq. ID No. 20) | |
| GCAGAGAGGG | ACC | GGCCAGCCAGACACAAGTG. | (Seq. ID No. 21) | |
| CAGAGAGGG | ACC | GGCCAGCCAGACACAAGTGC. | (Seq. ID No. 22) | |
| AGAGAGGG | ACC | GGCCAGCCAGACACAAGTGCT. | (Seq. ID No. 23) | |
| GAGAGGG | ACC | GGCCAGCCAGACACAAGTGCTG. | (Seq. ID No. 24) | |
| AGAGGG | ACC | GGCCAGCCAGACACAAGTGCTGG. | (Seq. ID No. 25) | |
| GAGGG | ACC | GGCCAGCCAGACACAAGTGCTGGC. | (Seq. ID No. 26) | |
| AGGG | ACC | GGCCAGCCAGACACAAGTGCTGGCA. | (Seq. ID No. 27) | |
| GGG | ACC | GGCCAGCCAGACACAAGTGCTGGCAA. | (Seq. ID No. 28) | |
| GG | ACC | GGCCAGCCAGACACAAGTGCTGGCAAC. | (Seq. ID No. 29) | |
| G | ACC | GGCCAGCCAGACACAAGTGCTGGCAACA. | (Seq. ID No. 30) | |
| | | GGCCAGCCAGACACAAGTGCTGGCAACAG. | (Seq. ID No. 31) | |

Therefore, in one embodiment, the oligonucleotide has 1, 2, 3, 4, 5 or 6 mismatches in complementarity to the Flaviviridae nucleotide sequence.

Other aspects of the present invention provide a method to treat a Flaviviridae infection by administering a therapeutically effective amount of a 2'-branched nucleoside, for example, a 2'-branched pyrimidine nucleoside, for example β-D-2'-CH$_3$-riboC, or its pharmaceutically acceptable pro-example to detect the presence of a Threonine at residue 405 of the RNA polymerase region of BVDV.

Table 3 below provides illustrative embodiments of HCV nucleotide sequences that include nucleotide position 8443 of the HCV genome (Genebank accession number AJ238799; Lohmann et al. (1999) Science 285(5424)110-113). Nucleotide position 8443 of the HCV genome corresponds to nucleotide position 11,136 of the BVDV genome and represents the conserved Serine residue of the RNA polymerase of Flaviviridae (Ser$_{405}$ of the BVDV genome, which corresponds to Ser$_{282}$ of the HCV genome (see FIG. 11)) that is mutated due to treatment with β-D-2'-CH$_3$-riboC. As stated above, given these sequences, one of ordinary skill using standard algorithms can construct oligonucleotide probes that are complementary or substantially complementary to the nucleotide sequences below.

in a host infected with a Flaviviridae that contains a Serine to Threonine mutation in the highly conserved consensus sequence, XRXSGXXXT (SEQ ID NO: 63), of domain B of the RNA polymerase region by administering a therapeutically effective amount of interferon. The codons ACA, ACG or ACU, which also encode Threonine, can be substituted for the codon ACC (in bold) in Table 3, as above, for example

TABLE 3

Nonlimiting examples of nucleic acid sequences encompassing a single point mutation at nucleotide 8443 (Genebank accession number AJ238799; Lohmann et al. (1999) Science 285(5424)110-113) of the RNA polymerase region of HCV.

|   |   |   |   |
|---|---|---|---|
|   | AGG |   | 282 S |
| AGAACTGCGGCTATCGCCGGTGCCGCGCG | ACC | GGTGTACTGACGACCAGCTGCGGTAATAC. | 282 T |
|   |   |   | (Seq. ID No. 32) |
| AGAACTGCGGCTATCGCCGGTGCCGCGCG | ACC | . | (Seq. ID No. 33) |
| GAACTGCGGCTATCGCCGGTGCCGCGCG | ACC | G. | (Seq. ID No. 34) |
| AACTGCGGCTATCGCCGGTGCCGCGCG | ACC | GG. | (Seq. ID No. 35) |
| ACTGCGGCTATCGCCGGTGCCGCGCG | ACC | GGT. | (Seq. ID No. 36) |
| CTGCGGCTATCGCCGGTGCCGCGCG | ACC | GGTG. | (Seq. ID No. 37) |
| TGCGGCTATCGCCGGTGCCGCGCG | ACC | GGTGT. | (Seq. ID No. 38) |
| GCGGCTATCGCCGGTGCCGCGCG | ACC | GGTGTA. | (Seq. ID No. 39) |
| CGGCTATCGCCGGTGCCGCGCG | ACC | GGTGTAC. | (Seq. ID No. 40) |
| GGCTATCGCCGGTGCCGCGCG | ACC | GGTGTACT. | (Seq. ID No. 41) |
| GCTATCGCCGGTGCCGCGCG | ACC | GGTGTACTG. | (Seq. ID No. 42) |
| CTATCGCCGGTGCCGCGCG | ACC | GGTGTACTGA. | (Seq. ID No. 43) |
| TATCGCCGGTGCCGCGCG | ACC | GGTGTACTGAC. | (Seq. ID No. 44) |
| ATCGCCGGTGCCGCGCG | ACC | GGTGTACTGACG. | (Seq. ID No. 45) |
| TCGCCGGTGCCGCGCG | ACC | GGTGTACTGACGA. | (Seq. ID No. 46) |
| CGCCGGTGCCGCGCG | ACC | GGTGTACTGACGAC. | (Seq. ID No. 47) |
| GCCGGTGCCGCGCG | ACC | GGTGTACTGACGACC. | (Seq. ID No. 48) |
| CCGGTGCCGCGCG | ACC | GGTGTACTGACGACCA. | (Seq. ID No. 49) |
| CGGTGCCGCGCG | ACC | GGTGTACTGACGACCAG. | (Seq. ID No. 50) |
| GGTGCCGCGCG | ACC | GGTGTACTGACGACCAGC. | (Seq. ID No. 51) |
| GTGCCGCGCG | ACC | GGTGTACTGACGACCAGCT. | (Seq. ID No. 52) |
| TGCCGCGCG | ACC | GGTGTACTGACGACCAGCTG. | (Seq. ID No. 53) |
| GCCGCGCG | ACC | GGTGTACTGACGACCAGCTGC. | (Seq. ID No. 54) |
| CCGCGCG | ACC | GGTGTACTGACGACCAGCTGCG. | (Seq. ID No. 55) |
| CGCGCG | ACC | GGTGTACTGACGACCAGCTGCGG. | (Seq. ID No. 56) |
| GCGCG | ACC | GGTGTACTGACGACCAGCTGCGGT. | (Seq. ID No. 57) |
| CGCG | ACC | GGTGTACTGACGACCAGCTGCGGTA, | (Seq. ID No. 58) |
| GCG | ACC | GGTGTACTGACGACCAGCTGCGGTAA. | (Seq. ID No. 59) |
| CG | ACC | GGTGTACTGACGACCAGCTGCGGTAAT. | (Seq. ID No. 60) |
| G | ACC | GGTGTACTGACGACCAGCTGCGGTAATA. | (Seq. ID No. 61) |
|   | ACC | GGTGTACTGACGACCAGCTGCGGTAATAC. | (Seq. ID No. 62) |

Therefore, in one embodiment, the oligonucleotide has 1, 2, 3, 4, 5 or 6 mismatches in complementarity to the Flaviviridae nucleotide sequence.

Other aspects of the present invention provide a method to treat a Flaviviridae infection by administering a therapeutically effective amount of a 2'-branched nucleoside, for example, a 2'-branched pyrimidine nucleoside, for example β-D-2'-CH$_3$-riboC, or its pharmaceutically acceptable prodrug and/or salt, to a human in need of therapy, in combination and/or alternation with one or more drugs that directly or indirectly induce a mutation in a Flaviviridae at a location other than a mutation of a nucleotide that results in a change from serine to a threonine in the highly conserved consensus sequence, XRXSGXXXT (SEQ ID NO: 63), of domain B of the RNA polymerase region, and/or one or more drugs that is associated with such mutation. As before, the codons ACA, ACG or ACU, which also encode Threonine, can be substituted for the codon ACC (in bold) in Table 3, for example to detect the presence of a Threonine in domain B of the RNA polymerase region of HCV.

Another aspect of the present invention provides a method to treat and/or to substantially cure a Flaviviridae infection to detect the presence of a Threonine at residue 282 of the RNA polymerase region of HCV.

In another embodiment, the invention provides an oligonucleotide primer for amplifying a Flaviviridae nucleic acid sequence. In one embodiment, the oligonucleotide is at least 14 nucleotides in length and hybridizes under sequence-specific, stringent hybridization conditions to a nucleotide sequence that contains the mutation.

Oligonucleotide sequences used as the hybridizing region of a primer can also be used as the hybridizing region of a probe. Suitability of a primer sequence for use as a probe depends on the hybridization characteristics of the primer. Similarly, an oligonucleotide used as a probe can be used as a primer.

It will be apparent to those of skill in the art that, provided with these embodiments, that specific primers and probes can be prepared by, for example, the addition of nucleotides to either the 5'- or 3'-ends, which nucleotides are complementary to the target sequence or are not complementary to the target sequence. So long as primer compositions serve as a point of initiation for extension on the target sequences, and so long as the primers and probes comprise at least 14 consecutive nucleotides contained within those exemplified embodiments, such compositions are within the scope of the invention.

The probe(s) herein can be selected by the following non-limiting criteria, which are not considered exclusive or determinative: (1) the probes are selected from the region of the Flaviviridae genome that contains the mutation; (2) the probes lack homology with any sequences of viral genomes that would be expected to compromise the test; and (3) the probes lack secondary structure formation in the amplified nucleic acid that, for example, can interfere with nucleic acid extension by an amplification enzyme such as E. coli DNA polymerase, such as the portion of the DNA polymerase referred to as the Klenow fragment. Prevention of secondary structure formation can be accomplished by employing up to about 15% by weight, preferably 5-10% by weight, dimethyl sulfoxide (DMSO) in the amplification medium and/or increasing the amplification temperatures to 300-40° C.

Further, the probe can have an approximate 50% content of guanine and cytidine, and may not contain multiple consecutive adenine and thymine residues at the 3'-end of the primer which can result in less stable hybrids.

The probes of the invention can be about 10 to 30 nucleotides long, preferably at least 14, 15, 20, 25, or 30 nucleotides in length. The nucleotides as used in the present invention can be ribonucleotides, deoxyribonucleotides and modified nucleotides such as inosine or nucleotides containing modified groups that do not essentially alter their hybridization characteristics. Probe sequences are represented throughout the specification as single stranded DNA oligonucleotides from the 5'- to the 3'-end. Any of the probes can be used as such, or in their complementary form, or in their RNA form (wherein T is replaced by U).

The probes according to the invention can be prepared by cloning of recombinant plasmids containing inserts including the corresponding nucleotide sequences, optionally by cleaving the latter from the cloned plasmids through the use of adequate nucleases and recovering them, e.g. by fractionation according to molecular weight. The probes according to the present invention can also be synthesized chemically, for instance, by the conventional phosphotriester or phosphodiester methods or automated embodiments thereof. In one such automated embodiment diethylphosphoramidites are used as starting materials and can be synthesized as described by Beaucage et al., Tetrahedron Letters (1981), 22:1859-1862. One method for synthesizing oligonucleotides on a modified solid support is described in U.S. Pat. No. 4,458,066. It is also possible to use a primer which has been isolated from a biological source (such as a restriction endonuclease digest).

The oligonucleotides used as primers or probes can also comprise nucleotide analogues such as phosphorothiates (Matsukura et al., 1967), alkylphosphorothiates (Miller et al., 1979), peptide nucleic acids (Nielsen et al., 1991; Nielsen et al., 1993), morpholino nucleic acids, locked nucleic acids, pseudocyclic oligonucleobases, 2'-O-4'-C-ethylene bridged nucleic acids or can contain intercalating agents (Asseline et al., 1984).

For designing probes with desired characteristics, the following useful guidelines known to the person skilled in the art can be applied. Because the extent and specificity of hybridization reactions are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

The stability of the probe to target nucleic acid hybrid should be chosen to be compatible with the assay conditions. This can be accomplished by avoiding long AT-rich sequences, by terminating the hybrids with GC base pairs, and by designing the probe with an appropriate $T_m$. The beginning and end of the probe should be chosen so that the length and % GC result in a $T_m$ of about 2-10° C. higher than the temperature at which the final assay will be performed. The base composition of the probe is significant because G-C base pairs exhibit greater thermal stability due to additional hydrogen bonding as compared to A-T base pairs. Thus, hybridization involving complementary nucleic acids of higher G-C content will be stable at higher temperatures. Conditions such as ionic strength and incubation temperature under which the probe will be used should also be taken into account when designing the probe. It is known that hybridization can increase as the ionic strength of the reaction mixture increases, and that the thermal stability of the hybrids can increase with increasing ionic strength. On the other hand, chemical reagents, such as formamide, urea, DIVISO and alcohols, which disrupt hydrogen bonds, can increase the stringency of hybridization. Destabilization of hydrogen bonds by such reagents can greatly reduce the $T_m$. In general, optimal hybridization for synthetic oligonucleotide probes of about 10-50 bases in length occurs approximately 5° C. below the melting temperature for a given duplex. Incubation at temperatures below the optimum can allow mismatched base sequences to hybridize and can therefore result in reduced specificity. It is desirable to have probes that hybridize only under conditions of high stringency, in which only highly complementary nucleic acid hybrids will form and/or hybrids without a sufficient degree of complementarity will not form. Accordingly, the stringency of the assay conditions determines the degree of complementarity needed between two nucleic acid strands that form the hybrid. The degree of stringency is chosen, for example, to maximize the difference in stability between the hybrid formed with the target and the non-target nucleic acid. In the present case, single base pair changes need to be detected, which requires conditions of very high stringency.

The length of the target nucleic acid sequence and the length of the probe sequence should also be considered. In some cases, there can be several sequences from a particular region, varying in location and length, which will yield probes with the desired hybridization characteristics. In other cases, one sequence can be significantly better than another which differs merely by a single base.

While it is possible for nucleic acids that are not perfectly complementary to hybridize, the longest stretch of perfectly complementary base sequences normally will determine hybrid stability. While oligonucleotide probes of different lengths and base compositions can be used, preferably oligonucleotide probes of this invention are between about 14 and 30 bases in length and optionally further have a sufficient sequence length that is perfectly complementary to the target nucleic acid sequence.

Regions in the target DNA or RNA that are known to form strong internal structures inhibitory to hybridization are less preferred. In one embodiment, probes with extensive self-complementarity are avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. Intramolecular and intermolecular hybrids may be formed within the molecules of a single probe if there is sufficient self-complementarity. Such structures can be avoided through careful probe design. By designing a probe so that a substantial portion of the sequence of interest is single stranded, the rate and extent of hybridization can be greatly increased. Computer programs are available to search for this type of interaction. However, in certain instances, it may not be possible to avoid this type of interaction.

Specific primers and sequence specific oligonucleotide probes can be used in a polymerase chain reaction that enables amplification and detection of the viral genomic sequences.

One aspect of the invention relates to specific oligonucleotide primers. The invention provides compositions comprising an oligonucleotide primer for amplifying an Flaviviridae nucleic acid wherein said primer is suitable for amplifying a nucleic acid subsequence from a Flaviviridae mutation. For example, the primer can be capable of detecting a G to C nucleotide change at nucleotide 1214 of the RNA polymerase region of BVDV. In another example, the primer can be capable of detecting a G to C nucleotide change at nucleotide 8443 of HCV genome.

Amplification and Detection of a Flaviviridae Mutation

Another aspect of the invention relates to methods for amplifying and detecting the presence of a Flaviviridae mutation.

DNA or RNA can be extracted from a bodily sample, such as blood or tissue material, such as liver, by a variety of techniques known in the art. An unpure sample, for example samples taken from plasma, serum or blood, can be treated with an amount of a reagent effective to open the cells, fluids, tissues, viral capsids or animal cell membranes of the sample, and to expose and/or separate the strand(s) of the nucleic acid(s), before amplification. This lysing and nucleic acid denaturing step to expose and separate the strands will allow amplification to occur much more readily.

In one embodiment, the invention provides a process to detect a mutation wherein a sample suspected of containing Flaviviridae nucleic acid sequence(s) is amplified; the amplified sequence is contacted with an oligonucleotide probe having a sequence complementary to the nucleotide sequence of the mutation; and the sequence is detected by hybridizing the probe to the sequence. In one embodiment, amplification is achieved by the use of the polymerase chain reaction method. In another embodiment, the mutation is a nucleotide change from G to C at position 1214 of the RNA polymerase region of the BVDV genome. In yet another embodiment, the mutation is a nucleotide change from G to C at position 8443 of the HCY genome.

Amplification

The amplification method used can be the polymerase chain reaction (PCR; Saiki et al., 1988), ligase chain reaction (LCR; Landgren et al., 1988; Wu &Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992), amplification by means of Q9 replicase (Lizardi et al., 1988; Lomeli et al., 1989), or any other suitable method to amplify nucleic acid molecules known in the art.

Polymerase Chain Reaction

The PCR process for amplification is generally well known in the art (See, for example, U.S. Pat. Nos. 4,683,202 and 4,683,194). The amplification process can involve an enzymatic chain reaction for preparing, in exponential quantities relative to the number of reaction steps involved, a specific nucleic acid sequence, given that the ends of the required sequence are known in sufficient detail that oligonucleotide primers can be synthesized that will hybridize to them, and that a small amount of the sequence is available to initiate the chain reaction. One primer is complementary to the negative (−) strand and the other is complementary to the positive (+) strand. Annealing the primers to denatured nucleic acid followed by extension with an enzyme such as the large fragment of DNA Polymerase I (Klenow) and nucleotides results in newly synthesized (+) and (−) strands containing the target sequence. Because these newly synthesized sequences are also templates for the primers, repeated cycles of denaturing, primer annealing and extension results in exponential accumulation of the region defined by the primer. The product of the chain reaction will be a discrete nucleic acid duplex with termini corresponding to the ends of the specific primers employed.

Any specific nucleic acid sequence can be produced by the present process. It is only necessary that a sufficient number of bases at both ends of the sequence be known in sufficient detail so that two oligonucleotide primers can be prepared which will hybridize to different strands of the desired sequence and at relative positions along the sequence such that an extension product synthesized from one primer, when it is separated from its template (compliment), can serve as a template for extension of the other primer into a nucleic acid of defined length. The greater the knowledge about the bases at both ends of the sequence, the greater can be the specificity of the primers for the target nuclei acid sequence, and thus the greater the efficiency of the process. It will be understood that the word primer as used hereinafter can refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code can be used for each strand. One primer from this collection can be substantially conserved with the end of the desired sequence to be amplified.

A specific nucleic acid sequence is produced by using the diagnostic marker nucleic acid containing that sequence as a template. If the target nucleic acid sequence of the sample contains two strands, it is necessary to separate the strands of the nucleic acid before they can be used as the template, either as a separate step or simultaneously with the synthesis of the primer extension products. This strand separation can be accomplished using any suitable denaturing techniques, including physical, chemical or enzymatic means, wherein the word "denaturing", as used herein, includes all such means. One physical method of separating the strands of the nucleic acid involves heating the nucleic acid unit until it is denatured. Typical heat denaturation can involve temperatures ranging from about 80-150° C. for times ranging from about 1 to 10 minutes. Strand separation can also be induced by an enzyme from the class of enzymes known as helicases or the enzyme RecA, which has helicase activity, and in the presence of riboATP is known to denature DNA. Reaction conditions suitable for separating the strands of nucleic acids with helicases are described by Kuhn Hoffmann-Berling, CSH-Quantitative Biology, 43:63 (1978), and techniques for using RecA are reviewed in C. Radding, Ann. Rev. Genetics, 16:405-37 (1982).

If the original nucleic acid containing the sequence to be amplified is single stranded, its compliment is synthesized by adding one or two oligonucleotide primers to it. If an appropriate single primer is added, a primer extension product is synthesized in the presence of the primer, an agent for polymerization, and the four nucleoside triphosphates described below. The product will be partially complementary to the single-stranded nucleic acid and will hybridize with the nucleic acid strand to form a duplex of unequal length strands that can then be separated into single strands as described above to produce two single separated complementary strands. Alternatively, two appropriate primers can be added to the single-stranded nucleic acid and the reaction carried out.

If the original nucleic acid constitutes the sequence to be amplified, the primer extension product(s) produced will be completely or substantially completely complementary to the strands of the original nucleic acid and will hybridize with them to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis is performed under conditions allowing hybridization of primers to templates to occur. Generally it occurs in a buffered aqueous solution, to obtain, for example, a pH range of 7-9. A molar excess (for genomic nucleic acid, usually about $10^8$: 1 primer: template) of the two oligonucleotide primers can be added to the buffer containing the separated template strands. It is understood, however, that the amount of complementary strand cannot be known if the process is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP and TTP are also added to the synthesis mixture, either separately or together with the primers, in adequate amounts and the resulting solution is heated to about 90-100° C. for from about 1 to 10 minutes, for example from about 1 to 4 minutes. After this heating period the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization can also be added together with the other reagents if it is heat stable. This synthesis reaction can occur from room temperature to a temperature above which the agent for polymerization no longer functions. Thus, for example, if DNA polymerase is used as the agent, the temperature is generally no greater than about 40° C. Most conveniently the reaction occurs at room temperature.

The agent for polymerization can be any compound or system that can function to accomplish the synthesis of primer extension products, including enzymes. Suitable enzymes for this purpose include, for example, *E. coli* DNA polymerase I, Klenow fragment of *E. coli* DNA polymerase I, T$_4$ DNA polymerase, other available DNA polymerases, polymerase muteins, reverse transcriptase(s), and other enzymes, including heat-stable enzymes (i.e., those enzymes that perform primer extension after being subjected to temperatures sufficiently elevated to cause denaturation), which can facilitate combination of the nucleosides in the proper manner to form the primer extension products that are complementary to each nucleic acid strand. Generally, the synthesis will be initiated at the 3'-end of each primer and proceed in the 5' direction along the template strand until synthesis terminates, producing molecules of different lengths. Alternatively, agents for polymerization that initiate synthesis at the 5'-end and proceed toward the 3'-end, using the same process as described above, can be used.

The newly synthesized strand and its complementary nucleic acid strand will form a double-stranded molecule under the hybridizing conditions described above if the target sequence is present, and this hybrid is used in the succeeding steps of the process.

In the next step, the sample treated under hybridizing conditions is subjected to denaturing conditions using any of the procedures described above to provide single-stranded molecules if the target sequence is present.

New nucleic acid is synthesized on the single-stranded molecules. Additional agents for polymerization, nucleosides and primers can be added if necessary for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target nucleic acid sequence to the extent necessary for detection. As will be described in further detail below, the amount of the specific nucleic acid sequence produced will accumulate in an exponential fashion.

When it is desired to produce more than one specific nucleic acid sequence from the first nucleic acid or mixture of nucleic acids, an appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process.

The present invention can be performed in a step-wise fashion where after each step new reagents are added, or simultaneously or in a single-step manner, where all reagents are added at the initial step, or partially step-wise and partially simultaneous, where fresh reagent is added after a given number of steps. If a method of denaturation, for example heat, is employed, which can inactivate the agent for polymerization, as in the case of a heat-labile enzyme, then it is necessary to replenish the agent after every strand separation step. The simultaneous method can be utilized when an enzymatic means is used for the strand separation step. In the simultaneous procedure, the reaction mixture can contain, in addition to the nucleic acid strand(s) with the desired sequence, the strand-separating enzyme (e.g., helicase), an appropriate energy source for the strand-separating enzyme (e.g. rATP), the four nucleoside triphosphates, the oligonucleotide primers in molar excess, and the agent for polymerization (e.g., Klenow fragment of *E. coli* DNA polymerase I).

If heat is used for denaturation in a simultaneous process, a heat-stable agent such as a thermostable polymerase can be employed that will operate at an elevated temperature, for example from about 50-105° C. depending on the agent, at which temperature the nucleic acid will consist of single and double strands in equilibrium. For smaller lengths of nucleic acid, lower temperatures of about 40-50° C. can be employed. The upper temperature range will depend on the temperature at which the enzyme will degrade or the temperature above which an insufficient level of primer hybridization will occur. Such a heat-stable enzyme is described, e.g., by A. S. Kaledin et al., Biokhimiya, 45, 644-651 (1980). For this constant temperature reaction to succeed, the primers have their 3' ends within 6-8 base pairs of each other. Each step of the process will occur sequentially notwithstanding the initial presence of all the reagents. Additional materials can be added as necessary. After the appropriate length of time has passed to produce the desired amount of the specific nucleic acid sequence, the reaction can be halted by inactivating the enzymes in any known manner or by separating the components of the reaction.

The amplification can also be carried out using a temperature-cycling reaction wherein the temperature is increased incrementally to allow for extension, annealing and denaturation using a heat-stable enzyme.

The process of the present invention can be conducted continuously. In one embodiment of an automated process, the reaction can be cycled through a denaturing region, a reagent addition region, and a reaction region. In another embodiment, the enzyme used for the synthesis of primer extension products can be immobilized in a column. Other reaction components can be continuously circulated by a pump through the column and a heating coil in series, thus the nucleic acids produced can be repeatedly denatured without inactivating the enzyme.

Flaviviridae genotyping using PCR techniques is commonly known in the art. Further, after PCR has been performed on samples suspected of containing a Flaviviridae, the Flaviviridae genome can be sequenced.

Detection of Hybridization of the Probe and Target Sequence

Suitable assay formats for detecting hybrids formed between probes and target nucleic acid sequences in a sample are known in the art (Sambrook et al., 1985). Detection of hybridization can be accomplished whether or not the nucleic acid has been amplified.

One method of detection is through the use of a labeled probe capable of hybridizing with the unamplified or amplified nucleic acid sequence and determining if the probe has hybridized. Such probe necessarily contains the nucleotide that is suspected of being mutated, such as 1214 of the RNA polymerase of BVDV or nucleotide 8443 of the HCV genome.

Oligonucleotides can be labeled by incorporating a label detectable by spectroscopic, photochemical, biochemical, immunochemical, or chemical means. Useful labels include $^{32}P$, fluorescent dyes, electron-dense reagents, enzymes (as commonly used in ELISAs), biotin, or haptens and proteins for which antisera or monoclonal antibodies are available.

The nucleic acid can be detected by analyzing it by Northern or Southern blots with or without radioactive probes. In one embodiment, a small sample of DNA from, e.g., peripheral blood suspected of containing Flaviviridae, is analyzed via a Southern blot technique using oligonucleotide probes to detect the specific nucleic acid viral marker. In another embodiment, a small sample of DNA from, e.g., peripheral blood suspected of containing Flaviviridae, is first amplified and then analyzed via a Southern blot technique using oligonucleotide probes to detect the specific nucleic acid viral marker.

Another method involves the oligomer restriction technique (such as described in U.S. Pat. No. 4,683,194). In this procedure, an amplified nucleic acid is denatured and hybridized in solution to a labeled oligonucleotide probe which hybridizes specifically to the target sequence (i.e., spans the particular conserved region contained by the primers) and spans at least one restriction site of interest. The duplex formed between target and probe will reconstitute the restriction site, and when cleaved with restriction enzyme, such as, e.g., BglI, PvuII, or HifI, releases a labeled probe fragment which can be resolved from the full-length probe by gel electrophoresis. The resulting gel is then autoradiographed. Analysis of the amplified product by this method can be rapid, i.e., within a few hours.

Another method that can be used to analyze an amplified product is the dot blot method. In a dot-blot method, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

An alternate format is a "reverse" dot-blot format, in which an amplified target DNA is labeled and the probes are immobilized on a solid support, such as a nylon membrane (see Saiki et al., 1989, Proc. Natl. Acad. Sci. USA 86:6230, and PCT Patent Publication No. 89/11548). The target DNA is typically labeled during amplification by the incorporation of one or more labeled primers. One or both of the primers can be labeled. The membrane-probe complex is incubated with the labeled amplified target DNA under suitable hybridization conditions, unhybridized target DNA is removed by washing under suitably stringent conditions, and the filter is then monitored for the presence of bound target DNA.

Alternatively, the reverse dot-blot assay can be carried out using a solid support having a plurality of probe hybridization sites or wells. For example, a microwell plate is particularly useful in large scale clinical applications of the present methods. Probes can be immobilized to a microwell plate either by passive binding or through a protein intermediate, such as bovine serum albumin (BSA), which adheres to microwell plates. Reverse dot-blot methods carried out in a microwell plate are described in U.S. Pat. No. 5,232,829, and Loeffelholz et al, 1992, J. Clin. Microbiol. 30(11):2847-2851. In another embodiment of the invention, a reverse dot-blot assay is carried out using microwell plates, and the primers are labeled with biotin, as described in Levenson and Chang, 1989, in PCR Protocols: A Guide to Methods and Applications, (Innis et al., eds., Academic Press. San Diego) pages 99-112. The probes are conjugated with BSA (see Tung et al., 1991, Bioconjugate Chem. 2:464-465, incorporated herein by reference) and immobilized on a microwell plate. Following amplification using the labeled primers and hybridization with the immobilized probes, the amplified nucleic acid is detected by first binding the biotin to avidin-horseradish peroxidase (A-HRP) or streptavidin-horseradish peroxidase (SAHRP), which is then detected by carrying out a reaction in which the HRP catalyzes a color change of a chromogen.

In an alternative method of immobilizing hybridization duplexes for detection, BSA-conjugated probes are bound to magnetic microparticles. The bound probes are hybridized in solution to labeled amplification product. Following hybridization, probe-target duplexes are removed from the solution magnetically, and the magnetically immobilized hybridization duplexes are then detected.

Another method of detection is referred to as a 5'-nuclease assay in which the labeled detection probes are added during the PCR amplification process. The probes are modified so as to prevent them from acting as primers for DNA synthesis. Any probe which hybridizes to target DNA during each synthesis step, i.e., during primer extension, is degraded by the 5' to 3' exonuclease activity of the DNA polymerase, e.g., Taq DNA polymerase. The degradation product from the probe is then detected. Thus, the presence of probe breakdown product indicates both that hybridization between probe and target DNA occurred and that the amplification reaction occurred. See also for example, U.S. Pat. No. 5,210,015.

The assay formats described above typically utilize labeled oligonucleotides to facilitate detection of the hybrid duplexes. Oligonucleotides can be labeled by any of the previously mentioned techniques, such as incorporating a label detectable by spectroscopic, photochemical, biochemical, immunochemical, or chemical means. Useful labels include$^{32}$ P, fluorescent dyes, electron-dense reagents, enzymes (as commonly used in ELISAS), biotin, or haptens and proteins for which antisera or monoclonal antibodies are available.

An alternative method for detecting the amplification of a Flaviviridae nucleic acid is by monitoring the increase in the total amount of double-stranded DNA in the reaction mixture (as described in Higuchi et al., 1992, Bio/Technology 10:413-417; Higuchi et al., 1993, Bio/Technology 11:1026-1030; and European Patent Publication Nos. 487,218 and 512,334). The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence.

Yet another method useful for detecting Flaviviridae mutations is through reverse hybridization assays. This is especially useful if a multitude of probes are involved. In one embodiment the selected set of probes are immobilized to a solid support in known distinct locations (dots, lines or other figures). In another embodiment the selected set of probes can be immobilized to a membrane strip in a line fashion. Said probes can be immobilized individually or as mixtures to delineated locations on the solid support. In a specific embodiment, a line probe assay can be used to screen for Flaviviridae genotypes containing the mutation of the present invention. The line probe assay involves multiple probes that are immobilized in parallel lines on a membrane, then a reverse hybridization of amplified nucleic acid fragments is performed. The hybrid can then be detected via a biotin-streptavidin coupling with a non-radioactive color developing system. See, for example, WO 97/40193.

Flaviviridae genotyping techniques can also be used to analyze the presence of Flaviviridae mutations. For example, sequence based phylogenetic analysis, differential hybridization, PCR or fragment length polymorphism can be used.

Detection of Flaviviridae Protein/Peptide Markers

In another embodiment, the invention provides a process for detecting viral markers diagnostic for long term 2'-branched nucleoside therapy failure for Flaviviridae infection wherein a sample containing Flaviviridae protein, peptides, or peptide fragments is analyzed for such viral markers. The proteins, peptides, or peptide fragments correlated with therapy failure can be detected by any generally applicable protein detection technology known in the art, including western blot, two dimensional gel electrophoresis, enzyme linked immunosorbent assays (ELISA), enhanced chemiluminescence (ECL), immunohistochemistry, ELISpot assays, peptide sequencing, or antibody based protein array technology. For example, protein expression of Flaviviridae viral markers diagnostic for 2'-branched nucleoside treatment can be analyzed with classical immunohistological methods. In these, the specific recognition is provided by the primary antibody (polyclonal or monoclonal) to the specific viral marker, but the secondary detection system can utilize fluorescent, enzyme, or other conjugated secondary antibodies. As a result, an immunohistological staining of the Flaviviridae infected tissue section for pathological examination is obtained.

Another method for detecting proteins, peptides, or peptide fragments that are diagnostic for long term response of Flaviviridae carriers to 2'-branched nucleoside therapy is the western blot. In brief, a sample containing Flaviviridae protein, peptide, or peptide fragments is separated via means of an electrophoretic gel. The separated proteins are then transferred to a medium such as nitrocellulose. Antibodies having a detectable label such as streptavidin-alkaline phosphatase reactive to specific Flaviviridae amino acid sequences correlated to 2'-branched nucleoside failure are then contacted onto the nitrocellulose medium containing the Flaviviridae amino acid sequences. Reactive antibodies will bind with the corresponding Flaviviridae amino acid sequence, and can be detected using a reagent such as nitoblue tetrazolium and 5-bromo-4-chloro-3-indlyl phosphate (BCIP). See, for example, Jalkanen, M., et al., J. Cell. Biol. 101:976-985 (1985); Jalkanen, M., et al., J. Cell. Biol. 105:3087-3096 (1987).

Alternatively, reactive antibodies present in the sera of Flaviviridae carriers can be used to detect the presence of Flaviviridae viral markers that are diagnostic of 2'-branched nucleoside treatment. Any known antibody assay technique known by those skilled in the art, including enzyme immunoassay (EIA), can be used. For example, in one embodiment a sample from an Flaviviridae carrier containing Flaviviridae specific antibodies is contacted with a solid support array containing specific Flaviviridae peptides correlated with 2'-branched nucleoside therapy success and/or failure. The reactive antibodies are then detected using rabbit anti-human IgG antibodies labeled with streptavidin-alkaline phosphatase and a reagent containing exposed to nitoblue tetrazolium and 5-bromo-4-chloro-3-indlyl phosphate.

Another method for detecting proteins, peptides, or peptide fragments that are diagnostic for long term response of Flaviviridae carriers to 2'-branched nucleoside therapy is by sequencing the protein, peptide, or peptide fragment using techniques known to one of ordinary skill in the art (see, for example, Matsudaira, P., J Biol Chem 262: 10035-10038, (1987); Salinovich, O. and Montelano, R., Anal. Biochem. 156: 341, (1986); Tarr, G. E.: Manual Edman Sequencing System. In: Shively, J. E., (ed.) Methods of Protein Microcharacterization. The Humana Press Inc., Clifton, N.J., 1986, pp. 155-194; and Fernandez, J., Andrews, L. and Mische, S., Anal. Biochem. 218: 112-117, (1994)). For example, one could use the Edman technique to determine the amino acid sequence of the peptide. In brief, the Edman chemistry removes amino acid residues from the N-terminus of a protein/peptide, one at a time in sequence. Each cycle of Edman chemistry, needed for the removal of each amino acid residue, consists of three steps: a coupling with phenyl isothiocyanate (PITC) under mildly alkaline conditions to form a phenylthiocarbamyl (PTC)-peptide; cleavage to release the first residue as its anilinothiazolinone (ATZ)- amino acid derivative; conversion of the ATZ derivative to a more stable phenylthiohydantoin (PTH)-amino acid derivative. The PTH-amino acid residue, removed in each cycle of Edman degradation, is identified by small or micro bore RP-HPLC. A full description of the process and possible pitfalls is given by Tarr, G. E.: Manual Edman Sequencing System. In: Shively, J. E., (ed.) Methods of Protein Microcharacterization. The Humana Press Inc., Clifton, N.J., 1986, pp. 155-194. Alternatively, if a sample yields no N-terminal sequence, the N-terminal residue is blocked, degraded during preparative procedures, or for steric reasons unavailable to the Edman chemistry reagents, then the sample can be subjected to controlled specific proteolysis, where the peptides are fractionated and then analyzed. This fractionation approach is described by Fernandez, J., Andrews, L. and Mische, S.: An improved procedure for enzymatic digestion of polyvinylidene difluoride-bound proteins for internal sequence analysis. Anal. Biochem. 218: 112-117, 1994.

Arrays

Another aspect of the present invention provides the use of DNA, RNA or peptide arrays to detect Flaviviridae nucleic acid viral markers. Such arrays include DNA macroarrays, DNA microarrays, and DNA microchips. DNA arrays, for example, have been described in U.S. Pat. Nos. 5,837,832, 5,807,522, 6,007,987, 6,110,426, WO 99/05324, 99/05591, WO 00/58516, WO 95/11995, WO 95/35505A1, WO 99/42813, JP10503841T$_2$, GR3030430T3, ES2134481T$_3$, EP804731B1, DE69509925C0, CA2192095AA, AU2862995A1, AU709276B2, AT180570, EP 1066506, and AU 2780499. Such arrays can be incorporated into computerized methods for analyzing hybridization results when the arrays are contacted with prepared sample nucleotides, for example, as described in PCT Publication WO 99/05574, and U.S. Pat. Nos. 5,754,524; 6,228,575; 5,593,839; and 5,856,101. Methods for screening for disease markers are also known to the art, for example, as described in U.S. Pat. Nos. 6,228,586; 6,160,104; 6,083,698; 6,268,398;

U.S. Pat. Nos. 6,228,578; and 6,265,174. Further descriptions of DNA array methods can, for example be found in: Shoemaker D. D. et al., Nature 409(6822):922-927 (2001); Kane M. D., et al., Nucleic Acids Res 28(22):4552-7 (2000); Taton T A, et al., Science. 289(5485): 1757-60 (2000); Jorg Reichert et al., Anal. Chem., 72(24):6025-6029 (2000); Reinke V, Mol Cell 6(3):605-16 (2000); Marx J. Science 289:1670-1672 (2000); Lockhart D. J. et al., Nature 405 (6788):827-836 (2000); Cortese J. D., The Scientist 14[17]: 25 (2000); Cortese J. D., The Scientist 14[11]:26 (2000); Fritz J. et al., Science. 288(5464):316-8 (2000); Mark Schena (Ed.), Microarray Biochip Technology, Eaton Publishing Company, Distributed by TeleChem/arrayit.com; Scherf U., et al., Nat Genet. 24(3):236-44 (2000); Ross D. T. et al., Nat Genet. 24(3):227-35 (2000); Walt D. R., Science 287: 451-452 (2000); Afshari C. A. et al., Cancer Res 59(19):4759-60 (1999); Gwynne P. and Page G., Science, 1999 August 6. (special advertising supplement; has a list of microarray-related companies); Baldwin D. et al., Curr Opin Plant Biol 2(2):96-103 (1999); Pollack J. R. et al., Nat Genet 23(1):41-6 (1999); Khan J. et al., Electrophoresis 20(2): 223-9 (1999); Gerhold D. et al., Trends Biochem Sei 24(5): 168-73 (1999); Ekins R. and Chu F. W., Trends in Biotechnology 17:217-218 (1999); Nuwaysir, E. F. et al., Molecular Carcinogenesis 24:153-159 (1999); Sinclair, B. The Scientist, 13(11):18-20 (1999); The Chipping Forecast, Nature Genetics (January 1999 Supplement); Schena, M. and Davis, R. W. Genes, Genomes and Chips. In DNA Microarrays: A Practical Approach (ed. M. Schena), Oxford University Press, Oxford, U K, 1999; Marton M. J. et al., Nat Med. 4(11):1293-301 (1998); Wang D. G. et al., Science 280(5366): 1077-82 (1998); Schena, M. and R. W. Davis. Parallel Analysis with Biological Chips, in PCR Methods Manual (eds. M. Innis, D. Gelfand, J. Sninsky), Academic Press, San Diego, 1998; Lemieux, B. et al., Molecular Breeding 4:277-289 (1998); Schena, M. et al., Trends in Biotechnology 16:301-306 (1998); Service, R. F., Science 282(5388):396-399 (1998); Service, R. F., Science 282 (5388):399-401 (1998); Kricka, L., Nature Biotechnology 16:513 (1998); Housman, D., Nature Biotechnology 16(6): 492-493 (1998); Ramsay, G., Nature Biotechnology 16(1): 40-44 (1998); Marshall, A. et al., Nature Biotechnology 16(1):27-31 (1998); Kononen J. et al., Nat. Med. 4(7):844-847 (19998); Blanchard, A. P. (1998) Synthetic DNA Arrays; in Genetic Engineering, Vol. 20, pp. 111-123, edited by J. K. Setlow, Plenum Press, New York; Proudnikov D. et al., Anal Biochem 259(1):34-41 (1998); Chen J. J. et al., Genomics 51(3):313-24 (1998); Wallace R. W., Molecular Medicine Today 3:384-389 (1998); Covacci, A. et al., Drug Development Research 41:180-192 (1997); Forozan, F. et al., Trends in Genetics 13:405-409 (1997); Blanchard, A. P. & L. Hood, Nature Biotechnology 14:1649 (1996); Blanchard, A. P. et al., Biosensors & Bioelectronics 11:687-690 (1996); DeRisi J. et al., Nat Genet 14(4):457-60 (1996); Shalon D. et al., Genome Res 6(7):639-45 (1996); Schena M. et al., Proc Natl Acad Sci USA 93(20): 10614-9 (1996); and Schena M. et al., Science 270(5235):467-70 (1995).

Probes on an array can be of varying lengths, including, but not limited to, as short as about 10-30 nucleotides long or as long as an entire Flaviviridae gene or Flaviviridae clone, which can be up to several kilobases. In addition, sequences of the various lengths as those described in Tables 2 and 3 (Seq ID Nos. 1-62) can be used as probes. The array can be designed such that all probes on the array can hybridize to their corresponding genes at about the same hybridization stringency. Probes for arrays should be unique at the hybridization stringencies used. A unique probe is only able to hybridize with one type of nucleic acid per target. A probe is not unique if at the hybridization stringency used, it hybridizes with nucleic acids derived from two different genes, i.e. related genes, or non-homologous sequences. The homology of the sequence of the probe to the gene and the hybridization stringency used help determine whether a probe is unique when testing a selected sample. Probes also may not hybridize with different nucleic acids derived from the same gene, i.e., splice variants. Since the splice variants of interest are known, several different probe sequences can be chosen from the target gene sequence of interest for an array, such that each probe can only hybridize to nucleic acid derived from one of the splice variants. In one embodiment, arrays containing Seq ID Nos. 1-62 are used at hybridization conditions allowing for selective hybridization. At conditions of selective hybridization, probes hybridize with nucleic acid from only one identified sequence. At conditions of selective hybridization, probes hybridize with nucleic acid from only one identified sequence. In another embodiment, arrays containing any Flaviviridae sequence of interest are used at hybridization conditions allowing for selective hybridization. At conditions of selective hybridization, probes hybridize with nucleic acid from only one identified sequence.

In one embodiment, the use of the microarray first requires amplification of genes of interest, such as by reverse transcription of mRNA or total RNA followed by polymerase chain reaction using methods known in the art. As the nucleic acid is copied, it is tagged with a label that can be used in the detection and quantitation methods known in the art. The nucleic acid can be labeled with radioactive or non-radioactive labels, but preferably contain fluorescent labels. The labeled nucleic acid is introduced to the microarray containing the sequence probes of interest and allowed to react for a period of time. Thereafter, the substrate is washed free of extraneous materials, leaving the nucleic acids on the target bound to the fixed probe molecules allowing for detection and quantitation by methods known in the art such as by autoradiograph, liquid scintillation counting, and/or fluorescence. As improvements are made in hybridization and detection techniques, they can be readily applied by one of ordinary skill in the art. As is well known in the art, if the probe molecules and target molecules hybridize by forming a strong non-covalent bond between the two molecules, it can be reasonably assumed that the probe and target nucleic acid are essentially completely complementary if the annealing and washing steps are carried out under conditions of high stringency. The detectable label provides a means for determining whether hybridization has occurred. By obtaining an image of the array with a detection and quantitation method known in the art such as autoradiography, liquid scintillation counting, or fluorescence it can be determined if and to what extent Flaviviridae gene sequences are present, by comparing intensities at specific locations on the array. High quantitation signals indicate that a particular sequence is present in a prepared sample, and an absent quantitation signal shows that a particular sequence is not present. The presence of various gene sequences under different conditions can be directly compared, such as prior to 2'-branched nucleoside treatment and during 2'-branched nucleoside treatment. Similarly, it can be determined what sequences are present in response to certain stimuli such as a 2'-branched nucleoside.

In one embodiment, the Flaviviridae sequence profile of a patient can be tracked over time using DNA array technologies. In an alternative embodiment, a patient with Flaviviridae receiving 2'-branched nucleoside as a modality, or other anti-Flaviviridae modality, can be monitored, over time, for changes in the aforementioned Flaviviridae genomic sequences in response to the treatment.

Arrays containing Seq ID Nos. 1-62, or any other identified Flaviviridae sequence of interest, can be made by any array synthesis method known in the art, such as spotting technology or solid phase synthesis via photolithography. Arrays can also be printed on solid substrates, e.g., glass microscope slides. Before printing, slides are prepared to provide a substrate for binding, as known in the art. Arrays can be printed using any printing techniques and machines known in the art. Printing involves placing the probes on the substrate, attaching the probes to the substrate, and blocking the substrate to prevent non-specific hybridization, as known in the art. Preferably the arrays of this invention are synthesized by solid phase synthesis using a combination of photolithography and combinatorial chemistry. Some of the key elements of probe selection and array design are common to the production of all arrays. Strategies to optimize probe hybridization, for example, are invariably included in the process of probe selection. Hybridization under particular pH, salt, and temperature conditions can be optimized by taking into account melting temperatures and by using empirical rules that correlate with desired hybridization behaviors (as described in Keller, G. H., and M. M. Manak (1987) DNA Probes, Stockton Press, New York, N.Y., pp. 169-170, hereby incorporated by reference). Computer models can be used for predicting the intensity and concentration-dependence of probe hybridization.

Moderate to high stringency conditions for hybridization are known in the art. An example of high stringency conditions for a blot are hybridizing at 68° C. in 5×SSC/5× Denhardt's solution/0.1% SDS, and washing in 0.2×SSC/ 0.1% SDS at room temperature. An example of conditions of moderate stringency are hybridizing at 68° C. in 5×SSC/5× Denhardt's solution/0.1% SDS and washing at 42° C. in 3×SSC. The parameters of temperature and salt concentration can be varied to achieve the desired level of sequence identity between a probe and a target nucleic acid. See, for example, Ausubel et al. (1995) Current Protocols in Molecular Biology, John Wiley & Sons, NY, N.Y., for further guidance on hybridization conditions. The melting temperature is described by the following formula (Beltz, G. A. et al., [1983] Methods of Enzymology, R. Wu, L. Grossman and K. Moldave [Eds.] Academic Press, New York 100:266-285). Tm=81.5° C.+16.6 Log[Na+]+0.41(+G+C)−0.61(% formamide)−600/length of duplex in base pairs.

Nucleic acids useful in this invention can be created by Polymerase Chain Reaction (PCR) amplification. PCR products can be confirmed by agarose gel electrophoresis. PCR is a repetitive, enzymatic, primed synthesis of a nucleic acid sequence. This procedure is well known and commonly used by those skilled in this art (see, for example, Mullis, U.S. Pat. Nos. 4,683,195, 4,683,202, and 4,800,159; Saiki et al., Science 230:1350-1354 (1985)). PCR is used to enzymatically amplify a DNA fragment of interest that is flanked by two oligonucleotide primers that hybridize to opposite strands of the target sequence. The primers are oriented with the 3'-ends pointing towards each other. Repeated cycles of heat denaturation of the template, annealing of the primers to their complementary sequences, and extension of the annealed primers with a DNA polymerase result in the amplification of the segment defined by the 5'-ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes that can be used are known to those skilled in the art.

Alternatively, probes made of peptide nucleic acids (PNAs) can be used as substitutes for probes made of oligonucleotides for the same uses as described above. The substitution of PNAs for oligonucleotides is well known in the art: The synthesis of peptide nucleic acids via preformed monomers has been described, for example, in PCT patent applications WO 92/20702 and WO 92/20703. Recent advances have also been reported on the synthesis, structure, biological properties, and uses of PNAs. See, for example, PCT Patent application WO 93/12129, U.S. Pat. No. 6,617, 422 to Neilsen P. E. et al., U.S. Pat. No. 5,539,083 to Cook et al., U.S. Patent application US20030059789A1, U.S. Pat. No. 6,475,721 to Kleiber et al., Egholm et al., Nature: 365, 566-568 (1993), Nielsen et al., Science 254:1497-1500 (1991); and Egholm et al., J. Am. Chem. Soc., 114:1895-1897 (1992).

Kits

A suitable test kit for use in an assay to determine the resistance status of a Flaviviridae sample to 2'-Branched nucleoside which makes use of a methodology according to one aspect of the invention, comprises (1) an oligonucleotide being complementary to a region of the wild-type DNA sequence (or its corresponding RNA) or to a region of the mutant DNA sequence as described herein; (2) materials required for polymerization of the nucleic acid from the 3'-end of the oligonucleotide; and (3) a means for determining the presence of an oligonucleotide primer extended product.

Polymerization materials include appropriate enzymes, buffers, washing solutions, labels and substrates for the label, if necessary. If PCR is used to amplify nucleic acid then additional materials such as appropriate oligonucleotide primers that will amplify a region of the wild-type DNA sequence (or its corresponding RNA) or a region of the mutant DNA sequence as described herein (or its corresponding RNA) and dNTP's (deoxynucleoside triphosphates) should be included. Instructions for conducting the assay can also be included.

A suitable test kit for use in an assay to determine the sensitivity of a Flaviviridae sample to interferon which makes use of a methodology according to another aspect of the invention comprises an oligonucleotide being complementary to a region of the wild-type DNA sequence (or its corresponding RNA) or to the pertinent region of the mutant DNA sequence, along with materials required to permit hybridization. Such materials include appropriate buffers, washing solutions, labels, and substrates for the labels, if necessary. In one embodiment, the oligonucleotide is labeled. If PCR is used to amplify nucleic acid prior to hybridisation then additional materials such as appropriate oligonucleotide primers that will amplify a region of the wild-type DNA sequence (or its corresponding RNA) or a region of the mutant DNA sequence, appropriate enzymes and dNTP's (deoxynucleotide triphosphates) should be included. Instructions for conducting the assay can also be included.

In another embodiment, the invention provides a kit for the detection of a marker of resistance to long term 2'-branched nucleoside treatment of a Flaviviridae infection. The kit can contain a compartment which contains an oligonucleotide probe which binds substantially to a nucleic acid subsequence of the Flaviviridae that contains the diagnostic marker. Alternatively, the kit contains peptide nucleic acid (PNA) or other antisense mimic probe in substitution for the oligonucleotide. The kit can also contain reagents to detect the hybridization of the probe to the Flaviviridae nucleic acid viral marker. The present invention also includes kits that can contain a primer for the PCR amplification of Flaviviridae nucleic acids. A kit can also contain a means for detecting amplified Flaviviridae nucleic acids, such as an oligonucleotide or peptide nucleic acid probe. In some cases, the probe is fixed to an appropriate support membrane. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

In addition, the kit can have a container which includes a positive control containing one or more nucleic acids with a sequence of the Flaviviridae viral genome correlated with therapy failure and/or a container including a negative control without such nucleic acids. Moreover, the kit can have a container for a restriction enzyme capable of cleaving a nucleic acid containing the target sequence at a site contained in a sequence in the probe.

The invention also provides a kit for the detection and/or genetic analysis of one or more viral markers of Flaviviridae that are correlated with therapy failure that can be present in a biological sample comprising the following components: (i) when appropriate, a means for releasing, isolating or concentrating the nucleic acids present in the sample; (ii) when appropriate, at least one suitable primer pair; (iii) at least two probes as defined above, possibly fixed to a solid support; (iv) a hybridization buffer, or components necessary for producing said buffer; (v) a wash solution, or components necessary for producing said solution; (vi) when appropriate, a means for detecting the hybrids resulting from the preceding hybridization; (vii) when appropriate, a means for attaching said probe to a known location on solid support; and/or (viii) instructions for carrying out the present method.

Furthermore, the invention also provides for a kit that contains peptide or peptide fragments corresponding to viral markers correlated with 2'-branched nucleoside therapy failure that can be used in an immunoassay to detect the presence of reactive antibodies in a sample. The peptide can be in a stabilized solution or lypholized. Such kit can contain an appropriate solution for hydrolyzing a lyophilized peptide. The kit can also contain an appropriate solid medium for blotting the aforementioned peptide on. The kit can also contain an appropriate reagent for detecting the presence of reactive antibodies to the peptide, such as an anti-human IgG antibody labeled with streptavidin-alkaline phosphatase. Furthermore, the kit can contain a detection agent such as nitroblue tetrazolium and 5-bromo-4-chloro-3-indlyl phosphate (BCIP).

Alternatively, the kit can contain antibodies reactive to specific peptide sequences associated with 2'-branched nucleoside therapy.

IV. Treatment of Flaviviridae Infections

Combination or Alternation Treatment with anti-Flaviviridae Agents Drug-resistant variants of Flaviviridae can emerge after prolonged treatment with an antiviral agent. Drug resistance most typically occurs by mutation of a gene that encodes for an enzyme used in viral replication. The efficacy of a drug against Flaviviridae infection can be prolonged, augmented, or restored by administering the compound in combination or alternation with a second, and perhaps third, antiviral compound that induces a different mutation from that caused by the principle drug. Combination therapy induces multiple simultaneous stresses on the virus. The pharmacokinetics, biodistribution, or other parameters of the drug can be altered by such combination or alternation therapy.

The present invention provides methods to achieve optimal treatment of a Flaviviridae infection through administration of a 2'-branched nucleoside, or a pharmaceutically acceptable prodrug and/or salt thereof, to a human in need of therapy in combination and/or alternation with one or more drugs that directly or indirectly induce a mutation in the viral genome at a location other than a mutation of a nucleotide that results in a change from serine to a different amino acid in the highly conserved consensus sequence, XRX<u>S</u>GXXXT (SEQ ID NO: 63), of domain B of the RNA polymerase region, and/or one or more drugs that is associated with such mutation.

Interferon Treatment of Mutant Flaviviridae Infections

Another aspect of the present invention provides a method to treat and/or to substantially cure a Flaviviridae infection in a host infected with a Flaviviridae that contains a Serine to Threonine mutation at the conserved serine amino acid residue of Domain B of the RNA polymerase region of a Flaviviridae (FIG. 11) by administering a therapeutically effective amount of interferon. In one embodiment, a method is provided to treat and/or to substantially cure a BVDV infection that contains a serine to threonine mutation at amino acid position 405 of the RNA polymerase region by administering a therapeutically effective amount of interferon. In another embodiment, a method is provided to treat and/or to substantially cure a HCV infection that contains a serine to threonine mutation at amino acid position 282 of the RNA polymerase region. of HCV by administering a therapeutically effective amount of interferon. In a specific embodiment, interferon alpha-2b is administered to treat and/or to substantially cure the Flaviviridae infection.

In a further embodiment, a method is provided to treat and/or to substantially cure a Flaviviridae infection in a host suspected of being infected with BVDV comprising: (i) obtaining a viral sample from the host; (ii) identifying whether the Flaviviridae in the sample contains a Threonine at amino acid residue 405 of the RNA polymerase; and (iii) administering an effective amount of interferon to the host infected with a Flaviviridae that contains a Serine to Threonine mutation at amino acid 405 of the RNA polymerase region.

In another embodiment, a method is provided to treat and/or to substantially cure a Flaviviridae infection in a host suspected of being infected with HCV comprising: (i) obtaining a viral sample from the host; (ii) identifying whether the Flaviviridae in the sample contains a Threonine at amino acid residue 282 of the RNA polymerase; and (iii) administering an effective amount of interferon to the host infected with a Flaviviridae that contains a Serine to Threonine mutation at amino acid 282 of the RNA polymerase region.

Interferons include: Intron-A (interferon alpha-2b) by Schering, PEG-INTRON™ (pegylated interferon alpha-2b) by Schering, Roferon-A (interferon alfa-2a) by Roche, PEGASYS® (pegylated interferon alfa-2a) by Roche, INFERGEN® (interferon alfacon-1) by InterMune, OMNIFERON™ (natural interferon) by Viragen, ALBUFERON® (interferon alpha) by Human Genome Sciences, REBIF® (interferon beta-1a) by Ares-Serono, Omega Interferon by BioMedicine, Oral Interferon Alpha by Amarillo Biosciences, and Interferon gamma-1b by InterMune.

Identification of the Serine to Threonine mutation at amino acid position 405 of the RNA polymerase region of BVDV, or amino acid position 282 of the RNA polymerase region of HCV, can be accomplished by detecting the presence of a mutation in the Flaviviridae genome that would allow for an amino acid change from Serine to Threonine. In one embodiment, the presence of cytidine at nucleotide 1214 of the RNA polymerase region of BVDV (where nucleotide 1214 of the RNA polymerase region corresponds to nucleotide 11,136 of the BVDV genome) can be used to detect the amino acid change. In other embodiments, the following double mutations can be detected: 1214 (G to C) and 1215 (C to A); 1214 (G to C) and 1215 (C to G); or 1214 (G to C) and 1215 (C to U), which result in an amino acid change from serine to threonine at position 405 of the RNA polymerase region of BVDV. In another embodiment, the presence of cytidine at nucleotide 8443 of the HCV genome can be used to detect the amino acid change. In other embodiments, the following double mutations can be detected: 8443 (G to C) and 8444 (C to A); 8443 (G to C) and 8444 (C to G); or 8443 (G to C) and 8444 (C to U), which result in an amino acid change from serine to threonine at position 282 of the RNA polymerase region of HCV. The mutations can be detected using any of the detection techniques described above, such as labeled probes, reverse hybridization assays, southern blots or any other detection technique known to one skilled in the art.

V. Preparation of Pharmaceutical Compositions

Any host, including a human, exhibiting an infection caused by a Flaviviridae virus can be treated by administering to the patient an effective amount of a 2'-branched nucleoside or a pharmaceutically acceptable prodrug and/or salt thereof, such as β-D-2'-$CH_3$-riboC or its 3' valine ester prodrug, in the presence of a pharmaceutically acceptable carrier or dilutent, for any of the indications or modes of administration as described in detail herein in combination or alternation with a drug that induces a mutation in the viral genome at a location other than a mutation of a nucleotide that results in a change from serine to a different amino acid in the highly conserved consensus sequence, XRX<u>S</u>GXXXT (SEQ ID NO: 63), of domain B of the RNA polymerase region. The 2'-branched nucleoside, such as β-D-2'-$CH_3$-riboC, or a pharmaceutically acceptable prodrug and/or salt thereof can be administered alone or in combination or alternation with other antiviral agents as described herein. The active materials can be administered by any appropriate route, for example, orally, parenterally, intravenously, intradermally, subcutaneously, or topically, in liquid or solid form.

A preferred dose of a compound will be in the range from about 1 to 50 mg/kg, preferably 1 to 20 mg/kg, of body weight per day, and more generally 0.1 to about 100 mg per kilogram body weight of the recipient per day. The effective dosage range of the pharmaceutically acceptable salts and prodrugs can be calculated based on the weight of the parent nucleoside to be delivered. If the prodrug and/or salt exhibits activity in itself, the effective dosage can be estimated using the weight of the prodrug and/or salt, or by other means known to those skilled in the art.

A compound can be conveniently administered in unit any suitable dosage form, including but not limited to one containing 7 to 3000 mg, preferably 70 to 1400 mg, of active ingredient per unit dosage form. For example, an oral dosage of 50-1000 mg of the active ingredient is usually convenient.

Ideally the active ingredient should be administered to achieve peak plasma concentrations of the active compound of from about 0.2 to 70 kM, preferably about 1.0 to 10 μM. This can be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compounds, sucrose as a sweetening agent and certain preservatives, dyes and colorings and flavors.

The compound, or a pharmaceutically acceptable prodrug and/or salt thereof, can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems.

Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811, which is incorporated herein by reference in its entirety. For example, liposome formulations can be prepared by dissolving appropriate lipid(s), such as stearoyl phosphatidyl ethanolamine, stearoyl phosphatidyl choline, arachadoyl phosphatidyl choline, and/or cholesterol, in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is swirled by hand to free lipid material from the sides of the container and to disperse lipid aggregates, thereby forming the liposomal suspension.

The active compound(s) are included in the pharmaceutically acceptable carrier or diluent in an amount sufficient to deliver to a patient a therapeutically effective amount of compound to inhibit viral replication in vivo, especially Flaviviridae replication, without causing serious toxic effects in the treated patient. By "inhibitory amount" is meant an amount of active ingredient sufficient to exert an inhibitory effect as measured by, for example, an assay such as the ones described herein.

Controlled Release Formulations

The field of biodegradable polymers has developed rapidly since the synthesis and biodegradability of polylactic acid was reported by Kulkami et al., in 1966 ("Polylactic acid for surgical implants," *Arch. Surg.*, 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers). See also U.S. Pat. No. 5,626,863 to Hubbell, et al which describes photopolymerizable biodegradable hydrogels as tissue contacting materials and controlled release carriers (hydrogels of polymerized and crosslinked macromers comprising hydrophilic oligomers having biodegradable monomelic or oligomeric extensions, which are end capped monomers or oligomers capable of polymerization and crosslinking); and WO 97/05185 to Focal, Inc. directed to multiblock biodegradable hydrogels for use as controlled release agents for drug delivery and tissue treatment agents.

Degradable materials of biological origin, such as crosslinked gelatin, are well known. Hyaluronic acid has been crosslinked and used as a degradable swelling polymer for biomedical applications (U.S. Pat. No. 4,957,744 to Della Valle et. al.; (1991) "Surface modification of polymeric biomaterials for reduced thrombogenicity," *Polym. Mater. Sci. Eng.*, 62:731-735]).

Many dispersion systems are currently in use, or being explored for use, as carriers of substances, and particularly of biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses yet anther method for drug delivery by forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

A number of patents disclose drug delivery systems that can be used to administer a 2'-branched nucleoside, or pharmaceutically acceptable prodrug and/or salt thereof, in combination and/or alternation with a drug that induces a mutation in the viral genome at a location other than a mutation of a nucleotide that results in a change from serine to a different amino acid in the highly conserved consensus sequence, XRXSGXXXT (SEQ ID NO: 63), of domain B of the RNA polymerase region. U.S. Pat. No. 5,749,847 discloses a method for the delivery of nucleotides into organisms by electrophoration. U.S. Pat. No. 5,718,921 discloses the use of microspheres comprising a polymer and drug dispersed therein as a delivery system. U.S. Pat. No. 5,629,009 discloses a delivery system for the controlled release of bioactive factors. U.S. Pat. No. 5,578,325 discloses the use of nanoparticles and microparticles of non-linear hydrophilic hydrophobic multiblock copolymers for drug delivery. U.S. Pat. No. 5,545,409 discloses a delivery system for the controlled release of bioactive factors. U.S. Pat. No. 5,494,682 discloses the use of ionically cross-linked polymeric microcapsules as a drug delivery system.

U.S. Pat. No. 5,728,402 to Andrx Pharmaceuticals, Inc. describes a controlled release formulation that includes an internal phase that comprises the active drug, its salt or prodrug, in admixture with a hydrogel forming agent, and an external phase which comprises a coating that resists dissolution in the stomach. U.S. Pat. Nos. 5,736,159 and 5,558,879 to Andrx Pharmaceuticals, Inc. disclose controlled release formulations for drugs with little water solubility in which a passageway is formed in situ. U.S. Pat. No. 5,567,441 to Andrx Pharmaceuticals, Inc. discloses a once-a-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation which can be made using a blend having an internal drug containing phase and an external phase which comprises a polyethylene glycol polymer which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 to Elan Corporation, plc discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 to Elan Corporation plc describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

The following examples illustrate various embodiments of the invention and are not intended to be limiting in any respect.

EXAMPLES

Example 1

Isolation of β-D-2'-$CH_3$-riboC-resistant BVDV

Persistent BVDV infection was established in MDBK cell line (ATCC, Manassas, Va., Catalog #: CCL-22) by in vitro infection of naive cells with a noncytophatic (ncp) BVDV (strain I-N-dIns; Dr. R. Donis, U. of Nebraska, Lincoln, Nebr.). The multiplicity of infection (MOI) was 0.01. Cells were passaged twice per week (splitting ratio 1:15) until the stable high-level of infection ($10^6$-$10^7$ focus forming units (FFU) per mL) was achieved, as was determined by a focus assay. Next, the persistently infected cells were grown in 6-well culture plates with 8 µM or without β-D-2'-$CH_3$-riboC (Idenix Pharmaceuticals). Cell cultures were passaged every three to four days by splitting with a ratio of 1:15 to 1:20. After eight passages, cell cultures grown in the presence of β-D-2'-$CH_3$-riboC were expanded to T-75 culture flask, freeze/thawed twice, and used as a virus stock of β-D-2'-$CH_3$-riboC-resistant BVDV for further characterization. The virus titers in cell cultures were monitored at the end of each passage by the virus focus assay.

To conduct the virus focus assay, MDBK cells were seeded onto 6-well plates containing $2 \times 10^5$ cells per well and grown at 37° C./5% $CO_2$ for at least 5 hours before use. The test samples (culture supernatants combined with cell monolayers) were frozen/thawed twice, serially diluted by 10-fold in medium, and used to inoculate test cells in 6-well plates at 0.2 mL per well. The inoculum was removed after 1 hour of adsorption, and the cells were overlaid with 3 mL of 0.5% agarose in complete growth medium (1×DMEM (Cellgro), supplemented with 8% horse serum, penicillin, streptomycin, L-glutamine, sodium pyruvate, and 25 mM HEPES). After 3 days of incubation at 37° C./5% $CO_2$, the plates were fixed for 1 hour with 3 mL of 7.4% formaldehyde in PBS, and washed with PBS. The cell monolayers were permeabilized with 1 mL of PBS-0.25% Triton X-100 per well for 10 minutes, and incubated with 0.5 mL of goat anti-BVDV antiserum (VMDR, Inc.; diluted 1:1000 in PBS-0.25% Triton X-100) for 1 hour. The antiserum was then removed, and cell monolayers were washed with PBS (twice for 15 min) and incubated with 0.5 mL of peroxidase-conjugated donkey anti-goat antibody (diluted 1:1000 in PBS-0.25% Triton X-100) for another 1 hour. After the antibody was removed, the cell monolayers were washed with PBS (twice for 15 min), and incubated with 0.5 mL of diaminobenzidine (DAB) peroxidase substrate solution (Vector Laboratories) at room temperature until virus foci become visible (approximately 15 minutes). All incubations were carried out with rocking. The staining was stopped by washing with water and the plates were allowed to air dry. Virus titers were calculated in FFU/mL, using the following equation: $T_{ffu/mL}=N \times 5 \times D$; where T is a virus titer in FFU/mL; N is a number of foci per well; and D is a dilution factor for the corresponding virus sample. (For example, if 12 foci were found in a well corresponding to 10-5 dilution of virus sample, than $T=12 \times 5 \times 10^5=6 \times 10^6$ FFU/mL).

Figure 1:
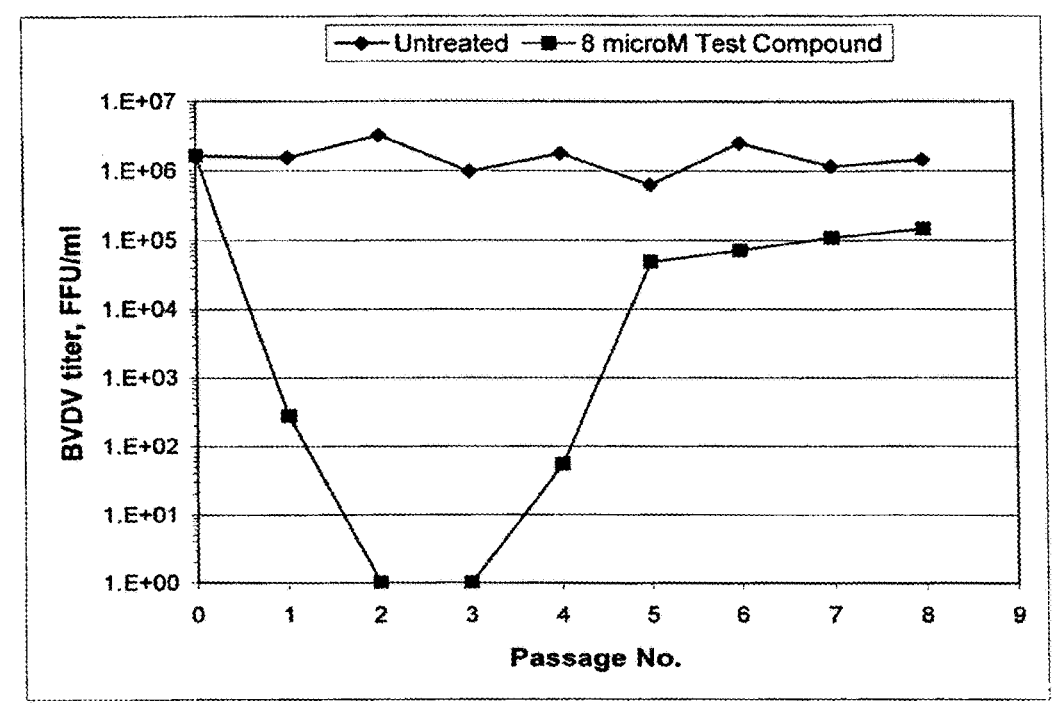
Figure 2:
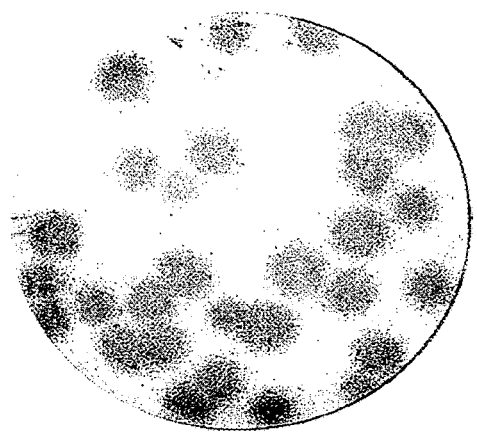
FIG. 2 illustrates the phenotype of focus formation by (A) the wild type (wt) BVDV (strain I-N-dIns), and by (B) the β-D-2'-CH₃-riboC-resistant BVDV (I-N-dIns β-D-2'-CH₃-riboC-R).
Figure 2:
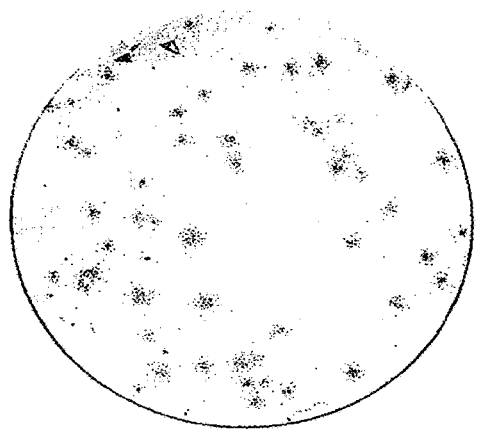

Typically, virus titers reached $10^6$-$10^7$ FFU/mL after 2-3 passages, and did not change significantly after further passaging over at least 2 months. When such a persistently infected cell line was treated with 8 μM β-D-2'-$CH_3$-riboC, the virus titer declined rapidly and the virus was no longer detectable after two passages (FIG. 1). However, after additional passaging in the presence of the inhibitor, virus reappeared in culture (typically, at passage 3 to 5), and virus titer reached plateau at $10^5$ FFU/mL, about ten-fold lower than that of untreated culture (FIG. 1). This 10-fold difference in virus titers was observed even after 28 days of treatment. This experiment was repeated three times and similar results were obtained. The phenotype of the reappeared virus was remarkably different from the initial wild type virus: it yielded much smaller foci, typically, 3 to 10 times smaller in diameter then those of the wild type virus (FIG. 2). This phenotype did not change after prolonged passaging in culture in the presence of the inhibitor for at least 72 days, but, it quickly reverted to the wild type phenotype (large foci) after the discontinuation of the treatment.

Taken together, these data demonstrate that the wild type virus disappeared from cell culture after treatment, and the β-D-2'-$CH_3$-riboC-resistant virus variant demonstrated lesser replication fitness in tissue culture.

Example 2

Virus Growth Kinetics

The growth kinetics of both wild type and the β-D-2'-$CH_3$-riboC-resistant BVDV were compared. MDBK cells were seeded onto 6-well plates ($2 \times 10^1$ cells per well) and grown at 37° C./5% $CO_2$ overnight. Cells were infected with BVDV I-N-dIns or the β-D-2'-$CH_3$-riboC-resistant mutant, I-N-dIns β-D-2'-$CH_3$-riboC-R, at a multiplicity of infection of 0.1. After a 1-hour adsorption, the inoculum was removed, and cells were washed with PBS and then overlaid with 2 mL of fresh growth medium. For BVDV I-N-dIns β-D-2'-$CH_3$-riboC-R, duplicate wells were prepared in the presence or absence of 8 μM β-D-2'-$CH_3$-riboC. Cell cultures were incubated at 37° C./5% $CO_2$. At 0 (the end of the adsorption period), 6, 12, 24, 36, 48, 60, 72 hours post-infection, the cultures were frozen/thawed twice, and virus titers were quantified by the focus assay as described above.

Figure 3:
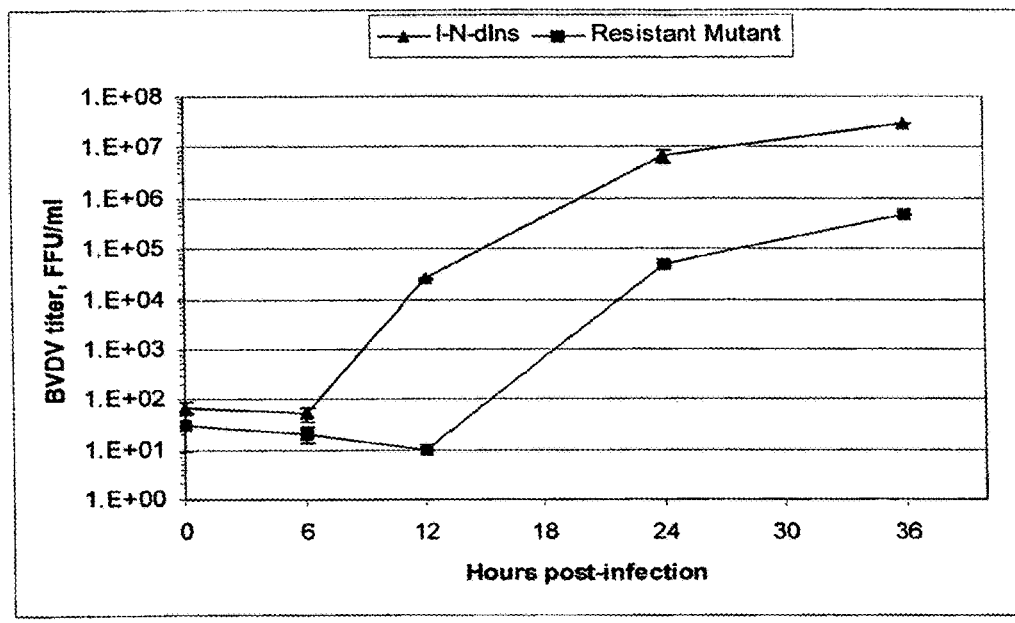
FIG. 3 demonstrates the growth kinetics of wild-type BVDV I-N-dIns and its β-D-2'-CH₃-riboC-resistant mutant, I-N-dIns β-D-2'-CH₃-riboC-R (Resistant Mutant).

At 12 hours post-infection, the wild type virus progeny reached a significant level of over $10^4$ FFU/mL, consistent with the BVDV complete life cycle being 8-14 hours. In contrast, the progeny of the resistant virus variant was still undetectable at that point (FIG. 3). The replication of the resistant virus was first detected at 24 hours post-infection. At 36 hours post-infection, the replication of the resistant virus was still about 100-fold less efficient than that of the wild type virus. These data clearly demonstrate that the β-D-2'-$CH_3$-riboC-resistant BVDV replicates significantly slower than the wild type virus, especially at the early stages of the infection. These data are also consistent with the results presented in FIGS. 1 and 2.

Example 3

Evaluation of the Resistance to β-D-2'-$CH_3$-riboC

The selected BVDV variant (I-N-dIns β-D-2'-$CH_3$-riboC-R) is more resistant to β-D-2'-$CH_3$-riboC than the wild type BVDV since it can stably replicate to a reasonably high levels in MDBK cells in the presence of the compound for a long period of time (at least 72 days) without changes in the phenotype nor in the virus titer levels. To quantitate this resistance, a virus yield reduction assay was performed, using both the wild type and the variant virus.

To conduct the virus yield reduction assay, MDBK cells were seeded onto 24-well plates ($1 \times 10^5$ cells per well) and grown at 37° C./5% $CO_2$ overnight. Cells were infected with BVDV at a multiplicity of infection of 0.1. After 1-hour adsorption, the inoculum was removed, and cells were washed with PBS and then overlaid with 1 mL of fresh growth medium, containing serial 2-fold dilutions of the test compound (0-32 μM for β-D-2'-$CH_3$-riboC and 0-800 IU/mL for Intron®A). After incubation at 37° C./5% $CO_2$ for 48 hours, the plates were frozen/thawed at −70° C. twice to lyse the cell cultures. The virus titer in the cell culture was quantified by focus assay as described above. The 50%, 90%, and 4-log effective concentrations (Mean values±Standard Deviation) for the test compound were based on duplicate wells. The $EC_{50}$, $EC_{90}$ and $EC_4$-log values were derived by curve fitting using XLFit software. The $EC_{50}$, $EC_{90}$, and $EC_4$ log are concentrations of test compound, which will reduce viral titer by 50%, 90%, and 99.99%, respectively.

Figure 4:
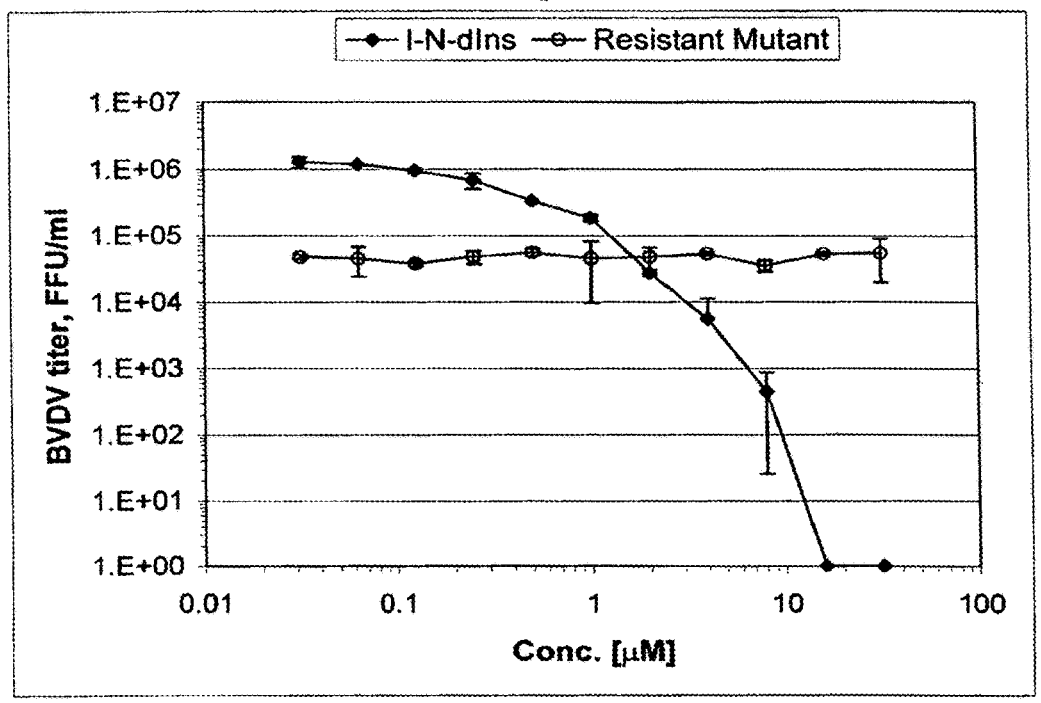
FIG. 4 shows the effect of β-D-2'-CH₃-riboC on the virus yield in de novo-infected MDBK cells (wherein I-N-dIns is wt BVDV, and the resistant mutant is I-N-dIns β-D-2'-CH₃-riboC-R (β-D-2'-CH₃-riboC-resistant BVDV)).

The generation of the infectious wild type BVDV particles was very efficiently inhibited by β-D-2'-$CH_3$-riboC, with an $EC_{50}$ and $EC_{90}$ values of 0.59±0.12 μM and 1.49±0.28 μM, respectively (FIG. 4 and Table 4). At β-D-2'-$CH_3$-riboC concentration of 7.14±1.26 μM the wild type virus yield was reduced by 4 logs, and at 16 μM virus titers dropped below the detection limit (<10 FFU/mL). In contrast, no effect on the resistant virus yield was observed at the highest β-D-2'-$CH_3$-riboC concentration tested (32 μM). Thus, the I-N-dIns β-D-2'-$CH_3$-riboC-R virus was at least 54-fold more resistant to the inhibitor than the wild type virus, based on the $EC_{50}$ values obtained by the virus yield reduction assay (>32 μM versus 0.59±0.12 μM).

TABLE 4

Results of BVDV Yield Reduction Assay

| Compound | BVDV strain | Biotype[1] | $EC_{50}$ (μM) | $EC_{90}$ (μM) | $EC_{4\,log}$ (μM) |
|---|---|---|---|---|---|
| β-D-2'-$CH_3$-riboC | I-N-dIns | ncp | 0.59 ± 0.12 | 1.49 ± 0.28 | 7.14 ± 1.26 |
| | I-N-dIns β-D-2'-$CH_3$-riboC-R | ncp | >32 | >32 | >32 |
| | I-NADL | cp | 0.68 ± 0.08 | 1.73 ± 0.11 | 8.22 ± 0.05 |
| | I-NADL S3674T | cp | >32 | >32 | >32 |

TABLE 4-continued

Results of BVDV Yield Reduction Assay

| Compound | BVDV strain | Bio-type[1] | EC$_{50}$ (μM) | EC$_{90}$ (μM) | EC$_{4\,log}$ (μM) |
|---|---|---|---|---|---|
| IFN | I-N-dIns | ncp | 2.64 ± 1.40 | 119 ± 34.1 | >800 |
| | I-N-dIns β-D-2'-CH$_3$-riboC-R | ncp | 0.19 ± 0.04 | 3.15 ± 0.72 | >800 |

[1]cp = cytopathic; ncp = noncytopathic

Nucleic Acid Sequence Analysis: Identification of the Genetic Mutation(s) Responsible for the β-D-2'-CH$_3$-riboC-Resistant Phenotype.

Based on the nature of the inhibitor, i.e. the nucleoside analog, the viral polymerase was considered as a plausible molecular target. Thus, we begun with the sequencing of the NS5B region for both wild type and the β-D-2'-CH$_3$-riboC-resistant BVDV. The viral RNA was extracted from the tissue culture lysates after 8 passages of treatment with or without β-D-2'-CH$_3$-riboC (FIG. 1), the entire NS5B region was subjected to the RT-PCR and sequencing. Viral RNA was extracted from cell cultures using QIAamp® Viral RNA Mini Kit (QIAGEN) according to the manufacture's protocol. The whole NS5B region was transcribed and amplified using QIAGEN® OneStep RT-PCR Kit. PCR products were purified using QIAquick® PCR Purification Kit (QIAGEN) and sequenced using the ABI PRISM® Sequencing protocol on an automated ABI DNA Sequencer (Perkin-Elmer) at the Tufts Core Facility, Boston, Mass.

Each region was sequenced in both directions using at least two independent RT-PCR products. No mutations were found in the wild type virus when compared to the previously published sequence of the BVDV (strain I-N-dIns) full-length genome (Vassilev, V. B. and R. O. Donis. (2000) Virus Res. 69 (2): 95-107). Bovine viral diarrhea virus (BVDV) induced apoptosis correlates with increased intracellular viral RNA accumulation. Only one nucleotide substitution was found in the I-N-dIns β-D-2'-CH$_3$-riboC-R virus: 1214G to C, changing amino acid residue Ser to Thr at position 405. Interestingly, this amino acid position is located to the putative functional NS5B domain B (FIG. 5), identified by mutational analysis (Lai V. C., Kao C. C., Ferrari E., Park J., Uss A. S., Wright-Minogue J., Hong Z., and J. Y. Lau. "Mutational analysis of bovine viral diarrhea virus RNA-dependent RNA polymerase" *J Virol.*, 1999, 73, 10129-36). This domain is also found in the NS5B region of HCV genome, as well as in genomes of other flaviviruses. Moreover, the amino acid position Ser$_{405}$ is highly conserved among all pesti- and flavivirus genomes.

Example 5

Hypersensitivity to Intron A

Figure 6:
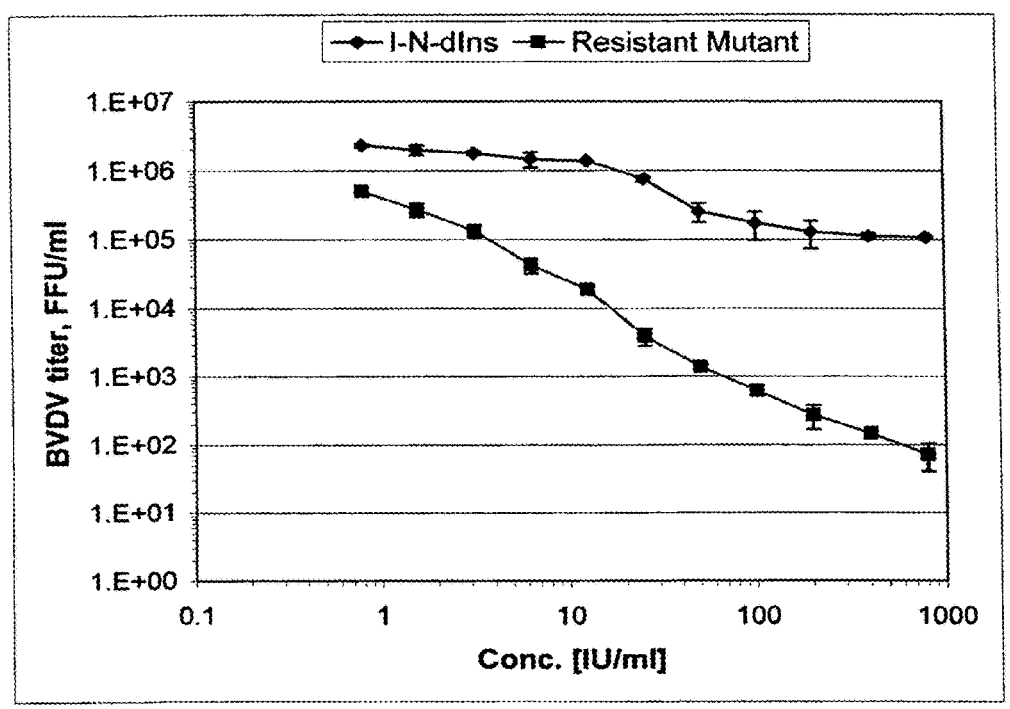
FIG. 6 illustrates the effect of interferon alpha-2b on the virus yields in de novo-infected MDBK cells (I-N-dIns: wt BVDV; I-N-dIns β-D-2'-CH₃-riboC-R: β-D-2'-CH₃-riboC-resistant BVDV (resistant mutant)).

Comparison of the wild type I-N-dIns virus and I-N-dIns β-D-2'-CH$_3$-riboC-R variant was conducted for their sensitivity to the Intron A in de novo-infected MDBK cells using the virus yield reduction assay, as described above. Again, we found a remarkable difference between the two viruses. The wild type virus was moderately inhibited by the Intron A with an EC$_{90}$ value of 119±34.1 μM and an approximate 1.5 log reduction in virus yield at the highest drug concentration tested (FIG. 6). In contrast, the I-N-dIns β-D-2'-CH$_3$-riboC-R variant virus was found to be much more sensitive to Intron A, with an EC$_{90}$ value of 3.15±0.72 μM and the maximum reduction in the viral yield of nearly 4 log (FIG. 6). Based on comparison of the EC$_{90}$ values, the β-D-2'-CH$_3$-riboC-resistant virus was approximately 40 times more sensitive to the Intron A than the wild type BVDV.

Example 6

Combination Treatment with β-D-2'-CH$_3$-riboC and Intron A

Figure 7:
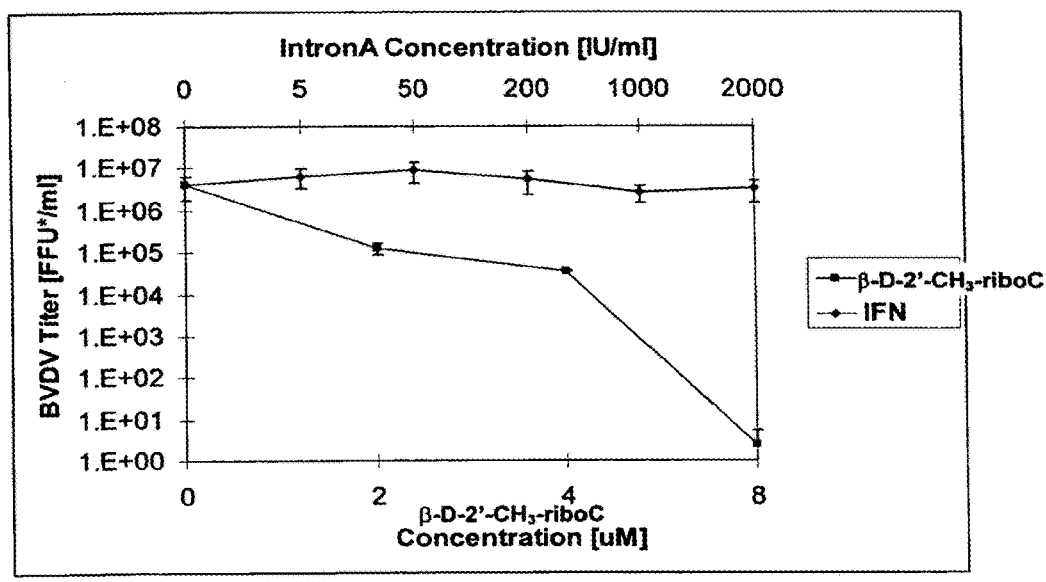
FIG. 7 illustrates the effect of β-D-2'-CH₃-riboC and interferon alpha-2b on BVDV (strain I-N-dIns) titers in persistently infected MDBK cells FIG. 8 demonstrates the effect of β-D-2'-CH₃-riboC in combination with interferon alpha-2b on wild-type BVDV (strain I-N-dIns) titers in persistently infected MDBK cells.
Figure 8:
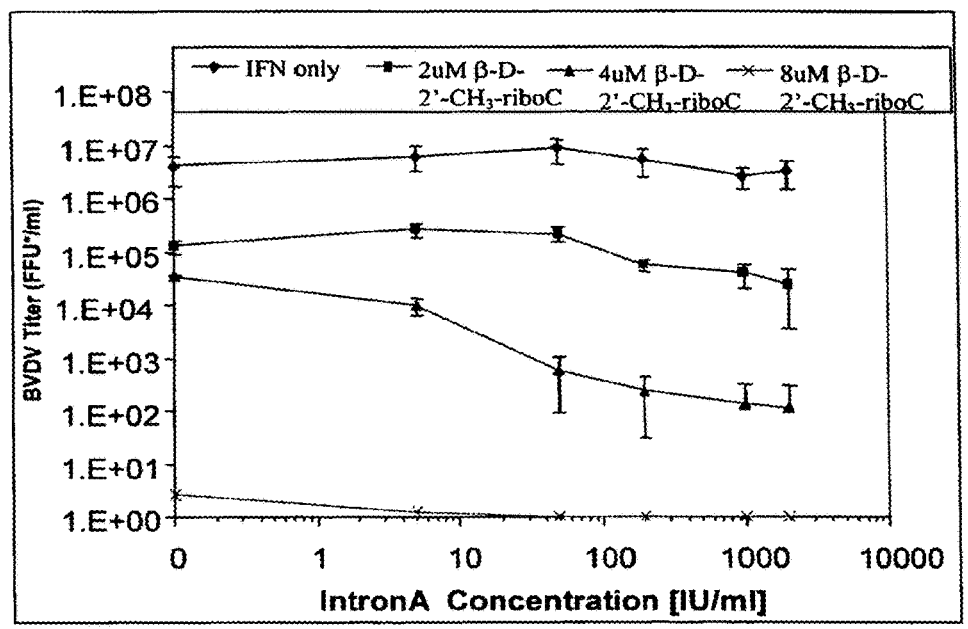

The effect of Intron A, alone or in combination with β-D-2'-CH$_3$-riboC, on the wild type BVDV was further studied in the persistently infected MDBK cells. In one experimental setting, the virus titers were determined after 7 days (two passages) of single or double treatment with several inhibitor concentrations. The results of this experiment, presented in Tables 5A and 5B, and also in FIGS. 7 and 8, can be summarized as follows. β-D-2'-CH$_3$-riboC alone strongly inhibited BVDV (strain I-N-dins) propagation in a dose-dependent manner under described experimental conditions. Treatment with 8 μM β-D-2'-CH$_3$-riboC reduced virus titer 6.2 logs (FIG. 7). Interferon alpha-2b alone had minimal antiviral effect (0.1 log-reduction in virus titers). Single treatment with 2 μM β-D-2'-CH$_3$-riboC or 2000 IU/mL interferon alpha-2b reduced viral titers 1.61 logs and 0.1 log, respectively. The effect of a combination treatment with the same concentrations was 2.22 logs, which was 0.51 log higher than the calculated additive effect (1.71 log). Single treatment with 4 μM β-D-2'-CH$_3$-riboC or 2000 IU/mL interferon alpha-2b reduced viral titers 2.06 logs and 0.1 log, respectively (Table 5B, FIG. 8). The effect of a combination treatment with same concentrations was 4.56 logs, which was 2.4 logs higher than the calculated additive effect (2.16 log). Thus, β-D-2'-CH$_3$-riboC and interferon alpha-2b acted synergistically to inhibit BVDV, especially when β-D-2'-CH$_3$-riboC was used at a concentration of 4 μM.

TABLE 5A

Effect of β-D-2'-CH$_3$-riboC and interferon alpha-2b on BVDV (strain I-N-dIns) titers in persistently infected MDBK cells. Numbers represent BVDV titer values in FFU/mL.

| | 0 μM β-D-2'-CH$_3$-riboC | 2 μM β-D-2'-CH$_3$-riboC | 4 μM β-D-2'-CH$_3$-riboC | 8 μM β-D-2'-CH$_3$-riboC |
|---|---|---|---|---|
| 0 IU/mL Interferon alpha-2b | 4.03 × 10$^6$ ± 2.34 × 10$^6$ | 1.25 × 10$^5$ ± 3.54 × 10$^4$ | 3.58 × 10$^4$ ± 1.06 × 10$^3$ | 2.50 × 10$^0$ ± 2.89 × 10$^0$ |
| 5 IU/mL Interferon alpha-2b | 6.44 × 10$^6$ ± 3.15 × 10$^6$ | 2.63 × 10$^5$ ± 7.42 × 10$^4$ | 1.00 × 10$^4$ ± 3.54 × 10$^3$ | 1.25 × 10$^0$ ± 2.50 × 10$^0$ |
| 50 IU/mL Interferon alpha-2b | 8.85 × 10$^6$ ± 4.53 × 10$^6$ | 2.13 × 10$^5$ ± 6.72 × 10$^4$ | 5.75 × 10$^2$ ± 4.84 × 10$^2$ | 0.00 × 10$^0$ ± 0.00 × 10$^0$ |

TABLE 5A-continued

Effect of β-D-2'-CH$_3$-riboC and interferon alpha-2b on BVDV (strain I-N-dIns)
titers in persistently infected MDBK cells. Numbers represent BVDV titer values in FFU/mL.

| | 0 μM<br>β-D-2'-CH$_3$-<br>riboC | 2 μM<br>β-D-2'-CH$_3$-<br>riboC | 4 μM<br>β-D-2'-CH$_3$-<br>riboC | 8 μM<br>β-D-2'-CH$_3$-<br>riboC |
|---|---|---|---|---|
| 200 IU/mL Interferon alpha-2b | $5.38 \times 10^6 \pm 3.03 \times 10^6$ | $5.75 \times 10^4 \pm 1.32 \times 10^4$ | $2.38 \times 10^2 \pm 2.06 \times 10^2$ | $0.00 \times 10^0 \pm 0.00 \times 10^0$ |
| 1000 IU/mL Interferon alpha-2b | $2.60 \times 10^6 \pm 1.14 \times 10^6$ | $3.93 \times 10^4 \pm 1.80 \times 10^5$ | $1.34 \times 10^2 \pm 2.35 \times 10^2$ | $0.00 \times 10^0 \pm 0.00 \times 10^0$ |
| 2000 IU/mL Interferon alpha-2b | $3.23 \times 10^6 \pm 1.77 \times 10^6$ | $2.44 \times 10^4 \pm 2.07 \times 10^4$ | $1.12 \times 10^2 \pm 1.93 \times 10^2$ | $0.00 \times 10^0 \pm 0.00 \times 10^0$ |

TABLE 5B

Effect of β-D-2'-CH$_3$-riboC and interferon alpha-2b
on BVDV (strain I-N-dIns) titers in persistently infected
MDBK cells. Numbers represent log values of the BVDV titers.

| | 0 μM<br>β-D-2'-CH$_3$-<br>riboC | 2 μM<br>β-D-2'-CH$_3$-<br>riboC | 4 μM<br>β-D-2'-CH$_3$-<br>riboC | 8 μM<br>β-D-2'-CH$_3$-<br>riboC |
|---|---|---|---|---|
| 0 IU/mL Interferon alpha-2b | 6.61 | 5.10 | 4.55 | 0.40 |
| 5 IU/mL Interferon alpha-2b | 6.81 | 5.42 | 4.00 | 0.10 |
| 50 IU/mL Interferon alpha-2b | 6.95 | 5.33 | 2.76 | 0.00 |
| 200 IU/mL Interferon alpha-2b | 6.73 | 4.76 | 2.38 | 0.00 |
| 1000 IU/mL Interferon alpha-2B | 6.41 | 4.59 | 2.13 | 0.00 |
| 2000 IU/mL Interferon alpha-2B | 6.51 | 4.39 | 2.05 | 0.00 |

Figure 9:
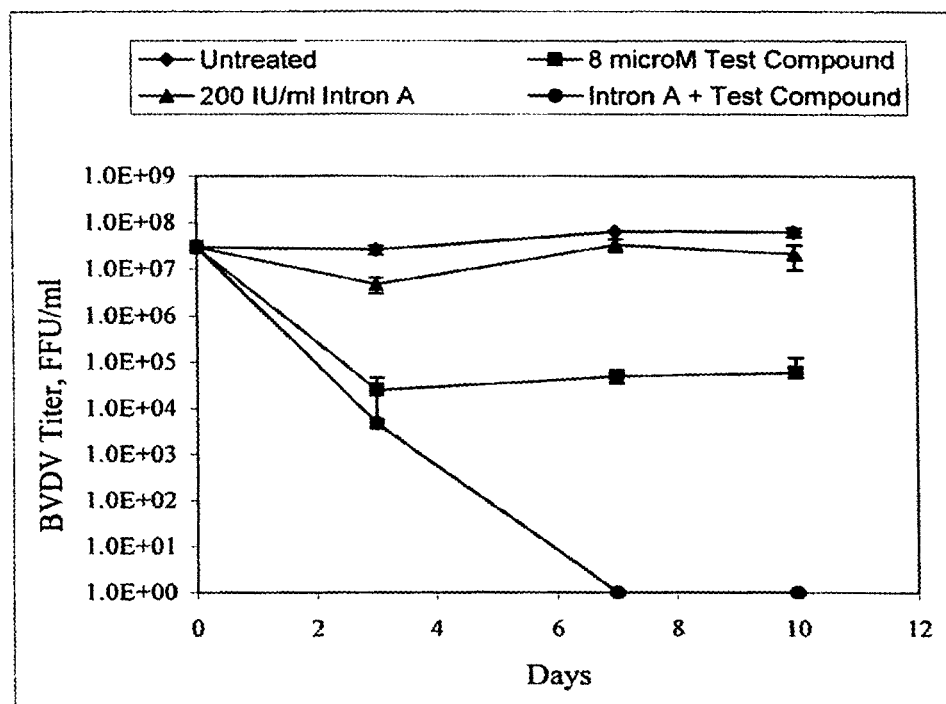
FIG. 9 shows the effect of β-D-2'-CH₃-riboC and interferon alpha-2b (Intron A) on BVDV (strain NY-1) titers in persistently infected MDBK cells.
Figure 10:
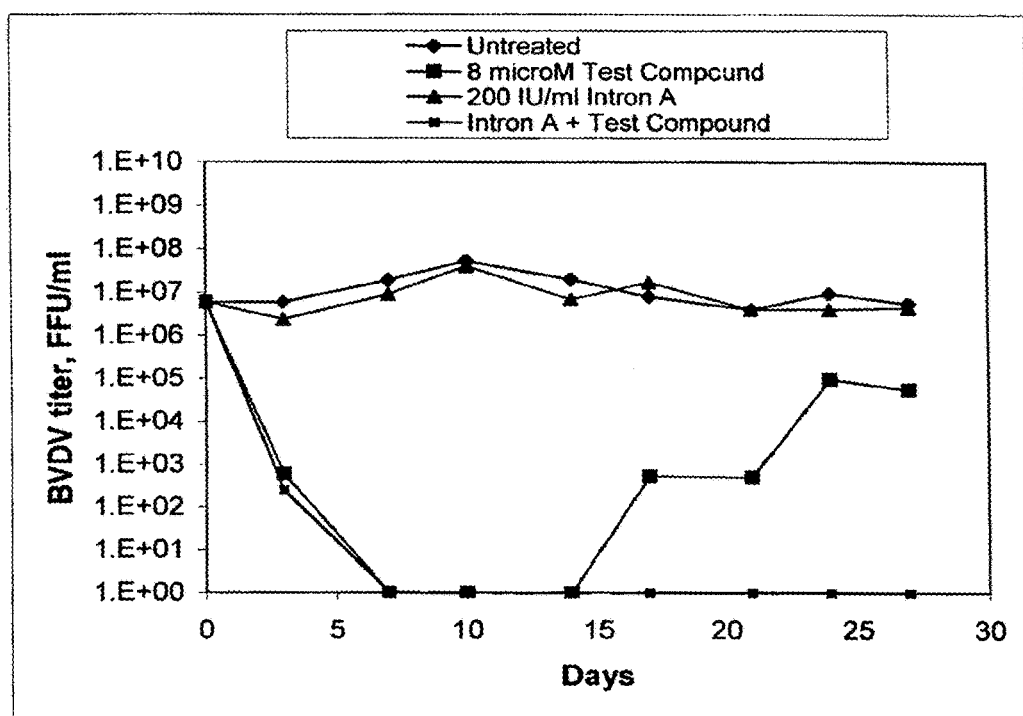
FIG. 10 illustrates the effect of β-D-2'-CH$_3$-riboC and interferon alpha-2b (Intron A) on wild-type BVDV (strain I-N-dIns) titers in persistently infected MDBK cells.

In another experimental setting, treatment time was extended to 10 days and the viral titers (strain NY-1) were monitored after each passage (every three to four days). Again, similar synergistic inhibitory effect of β-D-2'-CH$_3$-riboC and interferon alpha-2b was observed (FIG. 9). Notably, when cell cultures were treated with 8 μM of β-D-2'-CH$_3$-riboC in combination with 200 IU/mL of Intron A, the virus became undetectable after 7 days of treatment and did not reappear after further passaging for at least 27 days. These data are in agreement with our previously described finding, which is that β-D-2'-CH$_3$-riboC-resistant BVDV variant, arising after treatment of the persistently infected cells, is sensitive to the Intron A. Taken together, these data further suggest that the resistant virus populations, emerging after treatment of the persistent virus infection with β-D-2'-CH$_3$-riboC, can be eliminated by subsequent treatment with the Intron A.

This invention has been described with reference to specific embodiments. Variations and modifications of the invention, will be obvious to those skilled in the art from the foregoing detailed description of the invention.

We claim:

1. A method of treating a hepatitis C virus infection in a host, comprising:
   (a) administering an effective amount of a 2'-C-branched nucleoside, or a phosphate thereof, or a pharmaceutically acceptable salt thereof;
   (b) identifying viral resistance to the 2'-C-branched nucleoside in the host by detecting an amino acid 282 Ser to Thr mutation in the RNA polymerase region of the hepatitis C virus; and
   (c) administering to the host infected with the virus resistant to the 2'-C-branched nucleoside, an effective amount of one or more drugs that directly or indirectly induce a mutation in a hepatitis C virus at a location other than nucleotide 8443 (G to C) of the hepatitis C virus genome or amino acid 282 Ser to Thr of the RNA polymerase region of hepatitis C virus.

2. A method of treating a hepatitis C virus infection in a host, comprising:
   (a) administering an effective amount of a compound of formula III:

$$R^1-O-\underset{OR^2\ R^7}{\overset{X\overset{R^6}{\diagdown}Base}{\diamond}}\quad (III)$$

or a pharmaceutically acceptable salt, a stereoisomeric, tautomeric or polymorphic form thereof, wherein:
   Base is uracil;
   $R^1$ is mono-, di- or triphosphate, or a stabilized phosphate;
   $R^2$ is hydrogen;
   $R^6$ is alkyl, $CH_3$, $CF_3$, azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, or —N(acyl)$_2$;
   $R^7$ is fluorine; and
   X is O, S, $SO_2$, or $CH_2$;
   (b) identifying viral resistance to the compound of formula III in the host by detecting an amino acid 282 Ser to Thr mutation in the RNA polymerase region of the hepatitis C virus; and
   (c) administering to the host infected with the virus resistant to the compound of formula III, an effective amount of one or more drugs that directly or indirectly induce a mutation in a hepatitis C virus at a location other than nucleotide 8443 (G to C) of the hepatitis C virus genome or amino acid 282 Ser to Thr of the RNA polymerase region of hepatitis C virus.

3. The method of claim 1, wherein the host is human.

4. The method of claim 2, wherein the compound of formula III is in a pharmaceutically acceptable carrier or diluents.

5. The method of claim 4, wherein the drug in step (c) is interferon.

6. The method of claim 1, wherein identifying viral resistance in step (b) comprises assaying the blood of the host to test for seroconversion from wild type to mutant hepatitis C virus.

7. The method of claim 1, wherein identifying viral resistance in step (b) comprises phenotypic analysis of viral plaque growth from a viral culture sample from the host.

8. The method of claim 7, wherein the phenotypic analysis of step (b) comprises
   (i) obtaining a viral culture sample from the host;
   (ii) culturing the sample and comparing the plaque growth between the sample and wild type virus; and
   (iii) determining whether the plaque growth of the sample is smaller than the plaque growth of the wild type virus.

9. The method of claim 1, wherein identifying viral resistance in step (b) comprises determination of the replication fitness of the virus.

10. The method of claim 9, wherein the determination of the replication fitness of the virus in step (b) comprises:
    (i) obtaining a viral culture sample from the host;
    (ii) determining the replication fitness of the sample virus; and
    (iii) determining whether the replicon fitness of the sample virus is less than the replicon fitness of the wild type virus.

11. The method of claim 1, wherein identifying viral resistance in step (b) comprises detecting the presence of cytidine at nucleotide 8443 of the RNA polymerase region of the hepatitis C virus.

12. The method of claim 1, wherein identifying viral resistance in step (b) comprises:
    (i) contacting a sample containing a hepatitis C virus nucleic acid sequence with a detectable oligonucleotide probe having a sequence complementary to a codon that encodes a serine in the highly conserved consensus sequence, XRX<u>S</u>GXXXT (SEQ ID NO: 63), of domain B of the RNA polymerase region of the hepatitis C virus;
    (ii) allowing the probe to hybridize to the sequence; and
    (iii) detecting the hybridization of the probe to the sequence.

* * * * *

SEQUENCE LISTING

```
<160> NUMBER OF SEQ ID NOS: 77

<210> SEQ ID NO 1
<211> LENGTH: 61
<212> TYPE: DNA
<213> ORGANISM: Pestivirus sp.

<400> SEQUENCE: 1
aagtatatat aagaaatggg cagagaggga ccggccagcc agacacaagt gctggcaaca      60
g                                                                     61

<210> SEQ ID NO 2
<211> LENGTH: 32
<212> TYPE: DNA
<213> ORGANISM: Pestivirus sp.

<400> SEQUENCE: 2
aagtatatat aagaaatggg cagagaggga cc                                   32

<210> SEQ ID NO 3
```

```
<211> LENGTH: 32
<212> TYPE: DNA
<213> ORGANISM: Pestivirus sp.

<400> SEQUENCE: 3
agtatatata agaaatgggc agagagggac cg                                    32

<210> SEQ ID NO 4
<211> LENGTH: 32
<212> TYPE: DNA
<213> ORGANISM: Pestivirus sp.

<400> SEQUENCE: 4
gtatatataa gaaatgggca gagagggacc gg                                    32

<210> SEQ ID NO 5
<211> LENGTH: 32
<212> TYPE: DNA
<213> ORGANISM: Pestivirus sp.

<400> SEQUENCE: 5
tatatataag aaatgggcag agagggaccg gc                                    32

<210> SEQ ID NO 6
<211> LENGTH: 32
<212> TYPE: DNA
<213> ORGANISM: Pestivirus sp.

<400> SEQUENCE: 6
atatataaga aatgggcaga gagggaccgg cc                                    32

<210> SEQ ID NO 7
<211> LENGTH: 32
<212> TYPE: DNA
<213> ORGANISM: Pestivirus sp.

<400> SEQUENCE: 7
tatataagaa atgggcagag agggaccggc ca                                    32

<210> SEQ ID NO 8
<211> LENGTH: 32
<212> TYPE: DNA
<213> ORGANISM: Pestivirus sp.

<400> SEQUENCE: 8
atataagaaa tgggcagaga gggaccggcc ag                                    32

<210> SEQ ID NO 9
<211> LENGTH: 32
<212> TYPE: DNA
<213> ORGANISM: Pestivirus sp.

<400> SEQUENCE: 9
atataagaaa tgggcagaga gggaccggcc ag                                    32

<210> SEQ ID NO 10
<211> LENGTH: 32
<212> TYPE: DNA
<213> ORGANISM: Pestivirus sp.

<400> SEQUENCE: 10
ataagaaatg ggcagagagg gaccggccag cc                                    32
```

```
<210> SEQ ID NO 11
<211> LENGTH: 32
<212> TYPE: DNA
<213> ORGANISM: Pestivirus sp.

<400> SEQUENCE: 11
taagaaatgg gcagagaggg accggccagc ca                           32

<210> SEQ ID NO 12
<211> LENGTH: 32
<212> TYPE: DNA
<213> ORGANISM: Pestivirus sp.

<400> SEQUENCE: 12
aagaaatggg cagagaggga ccggccagcc ag                           32

<210> SEQ ID NO 13
<211> LENGTH: 32
<212> TYPE: DNA
<213> ORGANISM: Pestivirus sp.

<400> SEQUENCE: 13
agaaatgggc agagagggac cggccagcca ga                           32

<210> SEQ ID NO 14
<211> LENGTH: 32
<212> TYPE: DNA
<213> ORGANISM: Pestivirus sp.

<400> SEQUENCE: 14
gaaatgggca gagagggacc ggccagccag ac                           32

<210> SEQ ID NO 15
<211> LENGTH: 32
<212> TYPE: DNA
<213> ORGANISM: Pestivirus sp.

<400> SEQUENCE: 15
aaatgggcag agagggaccg gccagccaga ca                           32

<210> SEQ ID NO 16
<211> LENGTH: 32
<212> TYPE: DNA
<213> ORGANISM: Pestivirus sp.

<400> SEQUENCE: 16
aatgggcaga gagggaccgg ccagccagac ac                           32

<210> SEQ ID NO 17
<211> LENGTH: 32
<212> TYPE: DNA
<213> ORGANISM: Pestivirus sp.

<400> SEQUENCE: 17
atgggcagag agggaccggc cagccagaca ca                           32

<210> SEQ ID NO 18
<211> LENGTH: 32
<212> TYPE: DNA
<213> ORGANISM: Pestivirus sp.

<400> SEQUENCE: 18
tgggcagaga gggaccggcc agccagacac aa                           32
```

<210> SEQ ID NO 19
<211> LENGTH: 32
<212> TYPE: DNA
<213> ORGANISM: Pestivirus sp.

<400> SEQUENCE: 19
gggcagagag ggaccggcca gccagacaca ag                    32

<210> SEQ ID NO 20
<211> LENGTH: 32
<212> TYPE: DNA
<213> ORGANISM: Pestivirus sp.

<400> SEQUENCE: 20
ggcagagagg gaccggccag ccagacacaa gt                    32

<210> SEQ ID NO 21
<211> LENGTH: 32
<212> TYPE: DNA
<213> ORGANISM: Pestivirus sp.

<400> SEQUENCE: 21
gcagagaggg accggccagc cagacacaag tg                    32

<210> SEQ ID NO 22
<211> LENGTH: 32
<212> TYPE: DNA
<213> ORGANISM: Pestivirus sp.

<400> SEQUENCE: 22
cagagaggga ccggccagcc agacacaagt gc                    32

<210> SEQ ID NO 23
<211> LENGTH: 32
<212> TYPE: DNA
<213> ORGANISM: Pestivirus sp.

<400> SEQUENCE: 23
agagagggac cggccagcca gacacaagtg ct                    32

<210> SEQ ID NO 24
<211> LENGTH: 32
<212> TYPE: DNA
<213> ORGANISM: Pestivirus sp.

<400> SEQUENCE: 24
gagagggacc ggccagccag acacaagtgc tg                    32

<210> SEQ ID NO 25
<211> LENGTH: 32
<212> TYPE: DNA
<213> ORGANISM: Pestivirus sp.

<400> SEQUENCE: 25
agagggaccg gccagccaga cacaagtgct gg                    32

<210> SEQ ID NO 26
<211> LENGTH: 32
<212> TYPE: DNA
<213> ORGANISM: Pestivirus sp.

<400> SEQUENCE: 26
gagggaccgg ccagccagac acaagtgctg gc                    32

<210> SEQ ID NO 27
<211> LENGTH: 32
<212> TYPE: DNA
<213> ORGANISM: Pestivirus sp.

<400> SEQUENCE: 27
agggaccggc cagccagaca caagtgctgg ca                                    32

<210> SEQ ID NO 28
<211> LENGTH: 32
<212> TYPE: DNA
<213> ORGANISM: Pestivirus sp.

<400> SEQUENCE: 28
gggaccggcc agccagacac aagtgctggc aa                                    32

<210> SEQ ID NO 29
<211> LENGTH: 32
<212> TYPE: DNA
<213> ORGANISM: Pestivirus sp.

<400> SEQUENCE: 29
ggaccggcca gccagacaca agtgctggca ac                                    32

<210> SEQ ID NO 30
<211> LENGTH: 32
<212> TYPE: DNA
<213> ORGANISM: Pestivirus sp.

<400> SEQUENCE: 30
gaccggccag ccagacacaa gtgctggcaa ca                                    32

<210> SEQ ID NO 31
<211> LENGTH: 29
<212> TYPE: DNA
<213> ORGANISM: Pestivirus sp.

<400> SEQUENCE: 31
ggccagccag acacaagtgc tggcaacag                                        29

<210> SEQ ID NO 32
<211> LENGTH: 61
<212> TYPE: DNA
<213> ORGANISM: Hepatitis C virus

<400> SEQUENCE: 32
agaactgcgg ctatcgccgg tgccgcgcga ccggtgtact gacgaccagc tgcggtaata     60
c                                                                      61

<210> SEQ ID NO 33
<211> LENGTH: 32
<212> TYPE: DNA
<213> ORGANISM: Hepatitis C virus

<400> SEQUENCE: 33
agaactgcgg ctatcgccgg tgccgcgcga cc                                    32

<210> SEQ ID NO 34
<211> LENGTH: 32
<212> TYPE: DNA
<213> ORGANISM: Hepatitis C virus

<400> SEQUENCE: 34
gaactgcggc tatcgccggt gccgcgcgac cg                32

<210> SEQ ID NO 35
<211> LENGTH: 32
<212> TYPE: DNA
<213> ORGANISM: Hepatitis C virus

<400> SEQUENCE: 35
aactgcggct atcgccggtg ccgcgcgacc gg                32

<210> SEQ ID NO 36
<211> LENGTH: 32
<212> TYPE: DNA
<213> ORGANISM: Hepatitis C virus

<400> SEQUENCE: 36
actgcggcta tcgccggtgc cgcgcgaccg gt                32

<210> SEQ ID NO 37
<211> LENGTH: 32
<212> TYPE: DNA
<213> ORGANISM: Hepatitis C virus

<400> SEQUENCE: 37
ctgcggctat cgccggtgcc gcgcgaccgg tg                32

<210> SEQ ID NO 38
<211> LENGTH: 32
<212> TYPE: DNA
<213> ORGANISM: Hepatitis C virus

<400> SEQUENCE: 38
tgcggctatc gccggtgccg cgcgaccggt gt                32

<210> SEQ ID NO 39
<211> LENGTH: 32
<212> TYPE: DNA
<213> ORGANISM: Hepatitis C virus

<400> SEQUENCE: 39
gcggctatcg ccggtgccgc gcgaccggtg ta                32

<210> SEQ ID NO 40
<211> LENGTH: 32
<212> TYPE: DNA
<213> ORGANISM: Hepatitis C virus

<400> SEQUENCE: 40
cggctatcgc cggtgccgcg cgaccggtgt ac                32

<210> SEQ ID NO 41
<211> LENGTH: 32
<212> TYPE: DNA
<213> ORGANISM: Hepatitis C virus

<400> SEQUENCE: 41
ggctatcgcc ggtgccgcgc gaccggtgta ct                32

<210> SEQ ID NO 42
<211> LENGTH: 32
<212> TYPE: DNA
<213> ORGANISM: Hepatitis C virus -continued

```
<400> SEQUENCE: 42
gctatcgccg gtgccgcgcg accggtgtac tg                                    32

<210> SEQ ID NO 43
<211> LENGTH: 32
<212> TYPE: DNA
<213> ORGANISM: Hepatitis C virus

<400> SEQUENCE: 43
ctatcgccgg tgccgcgcga ccggtgtact ga                                    32

<210> SEQ ID NO 44
<211> LENGTH: 32
<212> TYPE: DNA
<213> ORGANISM: Hepatitis C virus

<400> SEQUENCE: 44
tatcgccggt gccgcgcgac cggtgtactg ac                                    32

<210> SEQ ID NO 45
<211> LENGTH: 32
<212> TYPE: DNA
<213> ORGANISM: Hepatitis C virus

<400> SEQUENCE: 45
atcgccggtg ccgcgcgacc ggtgtactga cg                                    32

<210> SEQ ID NO 46
<211> LENGTH: 32
<212> TYPE: DNA
<213> ORGANISM: Hepatitis C virus

<400> SEQUENCE: 46
tcgccggtgc cgcgcgaccg gtgtactgac ga                                    32

<210> SEQ ID NO 47
<211> LENGTH: 32
<212> TYPE: DNA
<213> ORGANISM: Hepatitis C virus

<400> SEQUENCE: 47
cgccggtgcc gcgcgaccgg tgtactgacg ac                                    32

<210> SEQ ID NO 48
<211> LENGTH: 32
<212> TYPE: DNA
<213> ORGANISM: Hepatitis C virus

<400> SEQUENCE: 48
gccggtgccg cgcgaccggt gtactgacga cc                                    32

<210> SEQ ID NO 49
<211> LENGTH: 32
<212> TYPE: DNA
<213> ORGANISM: Hepatitis C virus

<400> SEQUENCE: 49
ccggtgccgc gcgaccggtg tactgacgac ca                                    32

<210> SEQ ID NO 50
<211> LENGTH: 32
<212> TYPE: DNA
```

<213> ORGANISM: Hepatitis C virus

<400> SEQUENCE: 50
cggtgccgcg cgaccggtgt actgacgacc ag        32

<210> SEQ ID NO 51
<211> LENGTH: 32
<212> TYPE: DNA
<213> ORGANISM: Hepatitis C virus

<400> SEQUENCE: 51
ggtgccgcgc gaccggtgta ctgacgacca gc        32

<210> SEQ ID NO 52
<211> LENGTH: 32
<212> TYPE: DNA
<213> ORGANISM: Hepatitis C virus

<400> SEQUENCE: 52
gtgccgcgcg accggtgtac tgacgaccag ct        32

<210> SEQ ID NO 53
<211> LENGTH: 32
<212> TYPE: DNA
<213> ORGANISM: Hepatitis C virus

<400> SEQUENCE: 53
tgccgcgcga ccggtgtact gacgaccagc tg        32

<210> SEQ ID NO 54
<211> LENGTH: 32
<212> TYPE: DNA
<213> ORGANISM: Hepatitis C virus

<400> SEQUENCE: 54
gccgcgcgac cggtgtactg acgaccagct gc        32

<210> SEQ ID NO 55
<211> LENGTH: 32
<212> TYPE: DNA
<213> ORGANISM: Hepatitis C virus

<400> SEQUENCE: 55
ccgcgcgacc ggtgtactga cgaccagctg cg        32

<210> SEQ ID NO 56
<211> LENGTH: 32
<212> TYPE: DNA
<213> ORGANISM: Hepatitis C virus

<400> SEQUENCE: 56
cgcgcgaccg gtgtactgac gaccagctgc gg        32

<210> SEQ ID NO 57
<211> LENGTH: 32
<212> TYPE: DNA
<213> ORGANISM: Hepatitis C virus

<400> SEQUENCE: 57
gcgcgaccgg tgtactgacg accagctgcg gt        32

<210> SEQ ID NO 58
<211> LENGTH: 32

<212> TYPE: DNA
<213> ORGANISM: Hepatitis C virus

<400> SEQUENCE: 58
cgcgaccggt gtactgacga ccagctgcgg ta 32

<210> SEQ ID NO 59
<211> LENGTH: 32
<212> TYPE: DNA
<213> ORGANISM: Hepatitis C virus

<400> SEQUENCE: 59
gcgaccggtg tactgacgac cagctgcggt aa 32

<210> SEQ ID NO 60
<211> LENGTH: 32
<212> TYPE: DNA
<213> ORGANISM: Hepatitis C virus

<400> SEQUENCE: 60
cgaccggtgt actgacgacc agctgcggta at 32

<210> SEQ ID NO 61
<211> LENGTH: 32
<212> TYPE: DNA
<213> ORGANISM: Hepatitis C virus

<400> SEQUENCE: 61
gaccggtgta ctgacgacca gctgcggtaa ta 32

<210> SEQ ID NO 62
<211> LENGTH: 32
<212> TYPE: DNA
<213> ORGANISM: Hepatitis C virus

<400> SEQUENCE: 62
accggtgtac tgacgaccag ctgcggtaat ac 32

<210> SEQ ID NO 63
<211> LENGTH: 9
<212> TYPE: PRT
<213> ORGANISM: Artificial
<220> FEATURE:
<223> OTHER INFORMATION: HIGHLY CONSERVED CONSENSUS SEQUENCE OF DOMAIN B OF THE RNA POLYMERASE REGION OF FLAVIVIRIDAE
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 63

Xaa Arg Xaa Ser Gly Xaa Xaa Xaa Thr
1 5

<210> SEQ ID NO 64
<211> LENGTH: 14
<212> TYPE: PRT
<213> ORGANISM: Pestivirus sp.

<400> SEQUENCE: 64

Lys Arg Pro Arg Val Ile Gln Tyr Pro Glu Ala Lys Thr Arg
1               5                   10

<210> SEQ ID NO 65
<211> LENGTH: 6
<212> TYPE: PRT
<213> ORGANISM: Pestivirus sp.

<400> SEQUENCE: 65

Asp Thr Lys Ala Trp Asp
1               5

<210> SEQ ID NO 66
<211> LENGTH: 10
<212> TYPE: PRT
<213> ORGANISM: Pestivirus sp.

<400> SEQUENCE: 66

Ser Gly Gln Pro Asp Thr Ser Ala Gly Asn
1               5                   10

<210> SEQ ID NO 67
<211> LENGTH: 3
<212> TYPE: PRT
<213> ORGANISM: Pestivirus sp.

<400> SEQUENCE: 67

Gly Asp Asp
1

<210> SEQ ID NO 68
<211> LENGTH: 4
<212> TYPE: PRT
<213> ORGANISM: Pestivirus sp.

<400> SEQUENCE: 68

Glu Ala Gly Lys
1

<210> SEQ ID NO 69
<211> LENGTH: 4
<212> TYPE: PRT
<213> ORGANISM: Pestivirus sp.

<400> SEQUENCE: 69

Cys Ser Arg Asp
1

<210> SEQ ID NO 70
<211> LENGTH: 13
<212> TYPE: PRT
<213> ORGANISM: Hepatitis C virus

<400> SEQUENCE: 70

Cys Arg Ala Ser Gly Val Leu Thr Thr Ser Cys Gly Asn
1               5                   10

<210> SEQ ID NO 71
<211> LENGTH: 13
<212> TYPE: PRT
<213> ORGANISM: Hepatitis C virus

<400> SEQUENCE: 71

Cys Arg Ala Ser Gly Val Leu Thr Thr Ser Cys Gly Asn
1               5                   10

<210> SEQ ID NO 72
<211> LENGTH: 13
<212> TYPE: PRT
<213> ORGANISM: Pestivirus sp.

<400> SEQUENCE: 72

Gln Arg Gly Ser Gly Gln Pro Asp Thr Ser Ala Gly Asn
1               5                   10

<210> SEQ ID NO 73
<211> LENGTH: 13
<212> TYPE: PRT
<213> ORGANISM: Pestivirus sp.

<400> SEQUENCE: 73

Gln Arg Gly Ser Gly Gln Pro Asp Thr Ser Ala Gly Asn
1               5                   10

<210> SEQ ID NO 74
<211> LENGTH: 13
<212> TYPE: PRT
<213> ORGANISM: Hepatitis G virus

<400> SEQUENCE: 74

Cys Arg Ser Ser Gly Val Leu Thr Thr Ser Ala Ser Asn
1               5                   10

<210> SEQ ID NO 75
<211> LENGTH: 13
<212> TYPE: PRT
<213> ORGANISM: GBV-A-like virus

<400> SEQUENCE: 75

Cys Arg Ser Ser Gly Val Tyr Thr Thr Ser Ser Ser Asn
1               5                   10

<210> SEQ ID NO 76
<211> LENGTH: 13
<212> TYPE: PRT
<213> ORGANISM: Flavivirus sp.

<400> SEQUENCE: 76

Gln Arg Gly Ser Gly Gln Val Val Thr Tyr Ala Leu Asn
1               5                   10

<210> SEQ ID NO 77
<211> LENGTH: 13
<212> TYPE: PRT
<213> ORGANISM: Flavivirus sp.

<400> SEQUENCE: 77

Gln Arg Gly Ser Gly Gln Val Gly Thr Tyr Gly Leu Asn
1               5                   10